(12) United States Patent
Ancliff et al.

(10) Patent No.: US 7,157,457 B2
(45) Date of Patent: Jan. 2, 2007

(54) COMPOUNDS USEFUL IN THE TREATMENT OF INFLAMMATORY DISEASES

(75) Inventors: Rachael Anne Ancliff, Stevenage (GB); Caroline Mary Cook, Stevenage (GB); Colin David Eldred, Stevenage (GB); Paul Martin Gore, Stevenage (GB); Lee Andrew Harrison, Stevenage (GB); Simon Teanby Hodgson, Stevenage (GB); Duncan Bruce Judd, Stevenage (GB); Suzanne Elaine Keeling, Stevenage (GB); Xiao Qing Lewell, Stevenage (GB); Graeme Michael Robertson, Stevenage (GB); Stephen Swanson, Stevenage (GB)

(73) Assignee: Glaxo Group Limited, Greenford (GB)

( * ) Notice: Subject to any disclaimer, the term of this patent is extended or adjusted under 35 U.S.C. 154(b) by 363 days.

(21) Appl. No.: 10/381,871

(22) PCT Filed: Sep. 28, 2001

(86) PCT No.: PCT/GB01/04350

§ 371 (c)(1),
(2), (4) Date: Jul. 21, 2003

(87) PCT Pub. No.: WO02/26723

PCT Pub. Date: Apr. 4, 2002

(65) Prior Publication Data

US 2004/0058907 A1   Mar. 25, 2004

(30) Foreign Application Priority Data

Sep. 29, 2000 (GB) .................................. 0023973.1
Mar. 27, 2001 (GB) .................................. 0107643.9

(51) Int. Cl.
 *A61K 31/5375* (2006.01)
 *C07D 265/30* (2006.01)
(52) U.S. Cl. .................................. 514/237.8; 544/165
(58) Field of Classification Search ................ 544/165; 514/237.8
 See application file for complete search history.

(56) References Cited

U.S. PATENT DOCUMENTS 5,753,654 A * 5/1998 Kikuchi et al. .......... 514/230.5

FOREIGN PATENT DOCUMENTS

| EP | 0760362 | 3/1997 |
| WO | 0031032 | 6/2000 |
| WO | 0035449 | 6/2000 |
| WO | 0035876 | 6/2000 |

OTHER PUBLICATIONS

Patent Abstracts of Japan, vol. 016, No. 544, Nov. 13, 1992 & JP04208267, Jul. 29, 1992.
Harada, et. al., "Development of potent serotonin-3 (5-HT3) receptor antagonists. I. Structure-activity relationships of 2-alkoxy-4-amino-5-clorobenzamide derivatives", *Chemical and Pharmaceutical Bulletin, Pharmaceutical Society of Japan*, vol. 43, No. 8, 1995, 1364-1378.
Kato, et. al., "Novel benzamides as selective and potent gastrokinetic agents III. Synthesis and structure-activity relationships of 4-amino-5-chloro-2-methoxy-and 2-ethoxy-n-(4-substituted 2-morpholinyl) methyl-benzamides", *Chemical and Pharmaceutical Bulletin, Pharmaceutical Society of Japan*, vol. 40, No. 3, Mar. 1992, 652-660.
Kato, et. al., "Novel benzamides as selective and potent gastrokinetic agents 2. Synthesis and structure-activity relationships of 4-amino-5-chloro-2-ethoxy-n-4-(4-fluorobenzyl)-2-morpholinyl methylbenzamide citrate (as-4370) and related compounds", *Journal of Medicinal Chemistry, American Chemical Society*, vol. 34, No. 2, Feb. 1991, 616-624.
Kato, et. al., "Novel benzamides as selective and potent gastrokinetic agents 1. Synthesis and structure-activity relationships of n-(2-morpholinyl) alkylbenzamides", *Journal of Medicinal Chemistry, American Chemical Society*, vol. 33, No. 5, May 1990, 1406-1413.

* cited by examiner

*Primary Examiner*—Kamal A. Saeed
*Assistant Examiner*—Rebecca Anderson
(74) *Attorney, Agent, or Firm*—Alice P. Bradney

(57) ABSTRACT

There are provided according to the invention, novel compounds of formula (I)

wherein $R^1$, $R^2$, $R^3$, $R^4$, $R^5$, $R^6$, X, a, b and Z are as defined in the specification, processes for preparing them, formulations containing them and their use in therapy for the treatment of inflammatory diseases.

6 Claims, No Drawings

COMPOUNDS USEFUL IN THE TREATMENT OF INFLAMMATORY DISEASES

This application is filed pursuant to 35 USC 371 as a United States National Phase Application of International Patent Application Serial No. PCT/GB01/04350 filed 28 Sep. 2001, which claims priority from GB 0023973.1 filed on 29 Sep. 2000, and GB 0107643.9 filed on 27 Mar. 2001 in the United Kingdom.

This invention relates to novel chemical compounds, processes for their preparation, pharmaceutical formulations containing them and their use in therapy. Inflammation is a primary response to tissue injury or microbial invasion and is characterised by leukocyte adhesion to the endothelium, diapedesis and activation within the tissue. Leukocyte activation can result in the generation of toxic oxygen species (such as superoxide anion), and the release of granule products (such as peroxidases and proteases). Circulating leukocytes include neutrophils, eosinophils, basophils, monocytes and lymphocytes. Different forms of inflammation involve different types of infiltrating leukocytes, the particular profile being regulated by the profile of adhesion molecule, cytokine and chemotactic factor expression within the tissue.

The primary function of leukocytes is to defend the host from invading organisms, such as bacteria and parasites. Once a tissue is injured or infected, a series of events occurs which causes the local recruitment of leukocytes from the circulation into the affected tissue. Leukocyte recruitment is controlled to allow for the orderly destruction and phagocytosis of foreign or dead cells, followed by tissue repair and resolution of the inflammatory infiltrate. However in chronic inflammatory states, recruitment is often inappropriate, resolution is not adequately controlled and the inflammatory reaction causes tissue destruction. There is increasing evidence that the bronchial inflammation which is characteristic of asthma represents a specialised form of cell-mediated immunity, in which cytokine products, such as IL-4 and IL-5 released by Th2 T lymphocytes, orchestrate the accumulation and activation of granulocytes, in particular eosinophils and to a lesser extent basophils. Through the release of cytotoxic basic proteins, pro-inflammatory mediators and oxygen radicals, eosinophils generate mucosal damage and initiate mechanisms that underlie bronchial hyperreactivity. Therefore, blocking the recruitment and activation of Th2 cells and eosinophils is likely to have anti-inflammatory properties in asthma. In addition, eosinophils have been implicated in other disease types such as rhinitis, eczema, irritable bowel syndrome and parasitic infections.

Chemokines are a large family of small proteins which are involved in trafficking and recruitment of leukocytes (for review see Luster, New Eng. J. Med., 338, 436–445 (1998)). They are released by a wide variety of cells and act to attract and activate various cell types, including eosinophils, basophils, neutrophils, macrophages, T and B lymphocytes. There are two major families of chemokines, CXC-($\alpha$) and CC-($\beta$) chemokines, classified according to the spacing of two conserved cysteine residues near to the amino terminus of the chemokine proteins. Chemokines bind to specific cell surface receptors belonging to the family of G-protein-coupled seven transmembrane-domain proteins (for review see Luster, 1998). Activation of chemokine receptors results in, amongst other responses, an increase in intracellular calcium, changes in cell shape, increased expression of cellular adhesion molecules, degranulation and promotion of cell migration (chemotaxis).

To date, 9 members of CC chemokine receptors have been identified (CCR-1 to 9). Of particular importance to the current invention is the CC-chemokine receptor-3 (CCR-3), which is predominantly expressed on eosinophils, and also on basophils, mast cells and Th2 cells (Luster, 1998). Chemokines that act at CCR-3, such as RANTES, MCP-3 and MCP-4, are known to recruit and activate eosinophils. Of particular interest are eotaxin and eotaxin-2, which specifically bind to CCR-3. The localization and function of CCR-3 chemokines indicate that they play a central role in the development of allergic diseases such as asthma. Thus, CCR-3 is specifically expressed on all the major cell types involved in inflammatory allergic responses. Chemokines that act at CCR-3 are generated in response to inflammatory stimuli and act to recruit these cell types to sites of inflammation, where they cause their activation (e.g. Griffiths et al., J. Exp. Med., 179, 881–887 (1994), Lloyd et al., J. Exp. Med., 191, 265–273 (2000)). In addition, anti-CCR-3 monoclonal antibodies completely inhibit eotaxin interaction with eosinophils (Heath, H. et al., (1997) J. Clin. Invest. 99 (2), 178–184), while an antibody for the CCR-3 specific chemokine, eotaxin, reduced both bronchial hyperreactivity and lung eosinophilia in an animal model of asthma (Gonzalo et al., J. Exp. Med., 188, 157–167 (1998). Thus, many lines of evidence indicate that antagonists at the CCR-3 receptor are very likely to be of therapeutic use for the treatment of a range of inflammatory conditions.

A number of patent applications relating to CCR-3 antagonists have published before the filing date of this application. For example, EP 0 903 349, FR 2785902, WO 00/29377, WO 00/31032 and WO 00/31033 (all in the name of F. Hoffmann-La-Roche AG) disclose pyrrolidine, piperidine and piperazine based compounds which are all distinct from the compounds of the present invention.

WO 99/55324, WO 00/04003, WO 00/27800, WO 00/27835, WO 00/27843, WO 00/41685 and WO 00/53172 (all in the name of SmithKline Beecham Corporation) describe a variety of compounds as CCR-3 antagonists which are unrelated to the compounds of the present invention.

WO 00/34278 (Toray Industries Inc.) describe fused triazolo derived compounds as chemokine inhibitors.

WO 00/35449, WO 00/35451, WO 00/35452, WO 00/35453, WO 00/35454, WO 00/35876 and WO 00/35877 (Du Pont Pharmaceuticals Company) describe N-ureidoalkyl and heterocyclic piperidine compounds as CCR-3 antagonists.

WO 00/51607 and WO 00/51608 (Merck & Co. Inc.) describe a series of pyrrolidine modulators of chemokine receptor activity.

WO 00/53600 (Banyu Pharmaceutical Co. Ltd.) describes piperidine derivatives as inhibitors at the CCR-3 receptor.

WO 01/14333 (AstraZeneca UK Ltd.) describe substituted piperidine compounds as modulators of chemokine receptor activity.

EP 0 760 362 (Nisshin Flour Milling Co. Ltd.) describes morpholinoalkylurea derivatives which are disclosed as being useful in the treatment of digestive tract diseases.

JP 04208267A (Mitsui Seiyaku Kogyo KK) also describes morpholinoalkylurea derivatives which are disclosed as being useful as antiemetics, for activating peristalsis and ameliorating gastrointestinal function.

EP 243959A (Dainippon Pharm KK) describes O-substituted N-morpholinyl-alkyl-benzamide derivatives useful as gastrointestinal motility enhancing agents.

JO 1117-882A (Dainippon Pharm KK) describes heterocyclic morpholinyl alkylenyl carboxamide derivatives useful as anti-emetics.

WO 00/71518 (Sepracor Inc) describes morpholinoalkylamide derivatives useful in the treatment of pain, drug addiction and tinnitus.

WO 97/48695 and WO 97/48397 (Klinge Pharma Gmbh) describe pyridyl alkane, alkene and/or alkyne acid amide compounds useful as cytostatic, immunomodulatory or immuno-suppressive agents.

Kato et al., (1992) Chem. Pharm. Bull. 40(3), 652–660, Kato et al., (1991) J. Med. Chem. 34(2), 616–624 and Kato et al., (1990) J. Med. Chem. 33(5), 1406–1413 describe a series of morpholine benzamides which are disclosed as being selective and potent gastrokinetic agents.

We have now found a novel group of CCR-3 antagonist compounds which block migration/chemotaxis of eosinophils, consequently effecting anti-inflammatory properties. These compounds are therefore of potential therapeutic benefit, especially in providing protection from eosinophil, basophil and Th2-cell-induced tissue damage in diseases where such cell types are implicated, particularly allergic diseases, including but not limited to bronchial asthma, allergic rhinitis and atopic dermatitis.

In addition to a key role in inflammatory disorders, chemokines and their receptors also play a role in infectious disease. Mammalian cytomegaloviruses, herpes viruses and pox viruses express chemokine receptor homologues, which can be activated by human CC chemokines such as RANTES and MCP-3 (for review see Wells and Schwartz, Curr. Opin. Biotech., 8, 741–748, 1997). In addition, human chemokine receptors, such as CXCR-4, CCR-5 and CCR-3, can act as co-receptors for the infection of mammalian cells by microbes such as human immunodeficiency viruses (HIV). CCR-3 serves as a co-receptor for certain clinical strains of HIV-1 and facilitates viral entry (e.g Choe, H. et al, Cell, 1996, 85, 1135–1148). A key ligand for CCR-3, eotaxin, blocked the process of HIV entry. Thus, chemokine receptor antagonists, including CCR-3 antagonists, may be useful in blocking infection of CCR-3 expressing cells by HIV or in preventing the manipulation of immune cellular responses by viruses such as cytomegaloviruses.

Thus, according to one aspect of the invention, we provide compounds of formula (I):

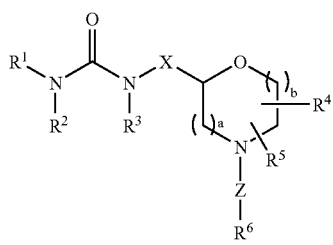

(I)

wherein:

R$^1$ represents C$_{1-6}$ alkyl, C$_{2-4}$ alkenyl, C$_{2-6}$ alkynyl, aryl-Y$^1$—, heteroaryl-Y$^1$—, aryl-(O)$_t$-aryl-Y$^1$—, aryl-(O)$_t$-heteroaryl-Y$^1$—, heteroaryl-(O)$_t$-aryl-Y$^1$—, heteroaryl-(O)$_t$-heteroaryl-Y$^1$—, aryl-SO$_2$—Y$^1$—, C$_{1-6}$ alkyl-G-Y$^1$—, heteroaryl-G-aryl-Y$^1$—, J$^1$-SO$_2$—Y$^1$—, R$^{17}$O(CO)—C$_{2-6}$ alkenyl-Y$^1$—, R$^{17}$NHCO—Y$^1$—, R$^{17}$NHSO$_2$—Y$^1$—, C$_{2-6}$ alkynyl-Y$^1$—, C$_{2-6}$ alkenyl-Y$^1$—, aryl-O—Y$^1$—, heteroaryl-O—Y$^1$—, C$_{1-6}$ alkyl-SO$_2$—Y$^1$—, M-Y$^1$—, J$^1$-Y$^1$—, J$^1$-CO—Y$^1$—, aryl-CO—Y$^1$— or C$_{3-8}$ cycloalkyl-Y$^1$— or C$_{3-8}$ cycloalkenyl-Y$^1$—, which C$_{2-6}$ alkynyl and C$_{2-6}$ alkynyl-Y$^1$ may be optionally substituted with a —OR$^{17}$ group, which C$_{2-6}$ alkenyl may be optionally substituted by one or more —COOR$^{17}$ groups and which cycloalkyl or cycloalkenyl may be optionally substituted by one or more hydroxyl or C$_{1-6}$ alkyl groups;

R$^2$ represents hydrogen or C$_{1-6}$ alkyl optionally substituted by a hydroxy group;

R$^3$ represents hydrogen or C$_{1-6}$ alkyl;

or R$^1$ and R$^2$ may together with the nitrogen atom to which they are attached form a group of formula J$^2$ wherein said nitrogen atom substitutes for either X$^1$ or X$^2$;

t represents 0 or 1.

X represents ethylene or a group of formula CR$^e$R$^f$ wherein R$^e$ and R$^f$ independently represent hydrogen or C$_{1-4}$ alkyl or R$^e$ and R$^f$ may together with the carbon atom to which they are attached form a C$_{3-8}$ cycloalkyl group;

R$^4$ and R$^5$ independently represent hydrogen or C$_{1-4}$ alkyl;

Z represents a bond, CO, SO$_2$, CR$^{10}$R$^7$(CH$_2$)$_n$, (CH$_2$)$_n$CR$^{10}$R$^7$, CHR$^7$(CH$_2$)$_n$O, CHR$^7$(CH$_2$)$_n$S, CHR$^7$(CH$_2$)$_n$OCO, CHR$^7$(CH$_2$)$_n$CO, COCHR$^7$(CH$_2$)$_n$ or SO$_2$CHR$^7$(CH$_2$)$_n$;

R$^6$ represents C$_{1-6}$ alkyl, C$_{2-6}$ alkenyl, aryl, heteroaryl, aryl-C$_{2-6}$ alkenyl-, —CN or a group of formula —Y$^2$-J$^3$;

R$^7$ represents hydrogen, C$_{1-4}$ alkyl, CONR$^8$R$^9$ or COOC$_{1-6}$ alkyl;

a and b represent 1 or 2, such that a+b represents 2 or 3;

G represents —SO$_2$—, —SO$_2$NR$^{18}$—, —NR$^{18}$SO$_2$—, —NR$^{18}$CO—, CO or —CONR$^{18}$—;

n represents an integer from 0 to 4;

M represents a C$_{3-8}$ cycloalkyl or C$_{3-8}$ cycloalkenyl group fused to a monocyclic aryl or monocyclic heteroaryl group;

J$^1$, J$^2$ and J$^3$ independently represent a moiety of formula (K):

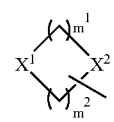

(K)

wherein X$^1$ represents oxygen, NR$^{11}$ or sulphur, X$^2$ represents CH$_2$, oxygen, NR$^{12}$ or sulphur, m$^1$ represents an integer from 1 to 3 and m$^2$ represents an integer from 1 to 3, provided that m$^1$+m$^2$ is in the range from 3 to 5, also provided that when both X$^1$ and X$^2$ represent oxygen, NR$^{11}$, NR$^{12}$ or sulphur, m$^1$ and m$^2$ must both not equal less than 2, wherein K is optionally substituted by one or more (eg. 1 or 2) —Y$^3$-aryl, —Y$^3$-heteroaryl, —Y$^3$—CO-aryl, —COC$_{3-8}$ cycloalkyl, —Y$^3$—CO-heteroaryl, —C$_{1-6}$ alkyl, —Y$^3$—COOC$_{1-6}$ alkyl, —Y$^3$—COC$_{1-6}$ alkyl, —Y$^3$—W, —Y$^3$—CO—W, —Y$^3$—NR$^{15}$R$^{16}$, —Y$^3$—CONR$^{15}$R$^{16}$, hydroxy, oxo, —Y$^3$—SO$_2$NR$^{15}$R$^{16}$, —Y$^3$—SO$_2$C$_{1-6}$ alkyl, —Y$^3$—SO$_2$aryl, —Y$^3$—SO$_2$heteroaryl, —Y$^3$—NR$^{13}$C$_{1-6}$ alkyl, —Y$^3$—NR$^{13}$SO$_2$C$_{1-6}$ alkyl, —Y$^3$—NR$^{13}$CONR$^{15}$R$^{16}$, —Y$^3$—NR$^{13}$COOR$^{14}$ or —Y$^3$—OCONR$^{15}$R$^{16}$ groups, and is optionally fused to a monocyclic aryl or heteroaryl ring;

R$^8$, R$^9$, R$^{10}$, R$^{11}$, R$^{12}$, R$^{13}$ and R$^{14}$ independently represent hydrogen or C$_{1-6}$ alkyl;

$R^{15}$ and $R^{16}$ independently represent hydrogen or $C_{1-6}$ alkyl or $R^{15}$ and $R^{16}$ together with the nitrogen atom to which they are attached may form a morpholine, piperidine or pyrrolidine ring;

$R^{17}$ and $R^{18}$ independently represent hydrogen or $C_{1-6}$ alkyl;

W represents a saturated or unsaturated, non-aromatic 5–7 membered ring containing between 1 and 3 heteroatoms selected from nitrogen, oxygen or sulphur, optionally substituted with one or more $C_{1-6}$ alkyl, halogen or hydroxy groups;

$Y^1$, $Y^2$ and $Y^3$ independently represent a bond or a group of formula —$(CH_2)_pCR^cR^d(CH_2)_q$— wherein $R^c$ and $R^d$ independently represent hydrogen or $C_{1-4}$ alkyl or $R^c$ and $R^d$ may together with the carbon atom to which they are attached form a $C_{3-8}$ cycloalkyl group, and p and q independently represent an integer from 0 to 5 wherein p+q is an integer from 0 to 5;

and salts and solvates thereof.

Specific groups of compounds of formula (I) which may be mentioned are those as defined above with the proviso that the compound of formula (I) is not a compound of formula (I)$^a$:

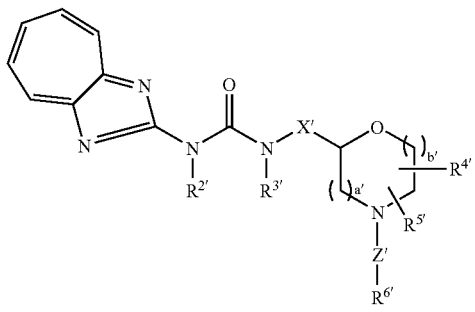

(I)$^a$ wherein $R^{2'}$ represents hydrogen or lower alkyl (specifically $C_{1-4}$ alkyl); $R^{3'}$ represents hydrogen; X' represents methylene or ethylene; a' and b' both represent 1; $R^{4'}$ and $R^{5'}$ both represent hydrogen; and wherein the moiety -Z'-$R^{6'}$ represents halobenzyl (compounds of formula (I)$^a$ are described in JP 04208267A); and/or the proviso that the compound of formula (I) is not a compound of formula (I)$^b$:

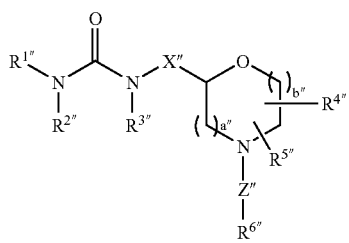

(I)$^b$ wherein $R^{1''}$ represents a hydrogen atom, a $C_{1-6}$ alkyl group, a $C_{3-6}$ cycloalkyl group, a $C_{3-6}$ cycloalkyl$C_{1-4}$ alkyl group, an aryl group or an aryl$C_{1-4}$ alkyl group (particularly wherein aryl represents phenyl or naphthyl) in which the aryl moiety of the aryl group or aryl$C_{1-4}$ alkyl group may be optionally substituted with a halogen atom, a $C_{1-6}$ alkyl group, a $C_{1-6}$ alkoxy group, a $C_{1-6}$ alkoxycarbonyl group or an amino group; $R^{2''}$ represents hydrogen; $R^{3''}$ represents hydrogen or $C_{1-6}$ alkyl; X" represents methylene; a" and b" both represent 1; $R^{4''}$ and $R^{5''}$ both represent hydrogen; and wherein the moiety -Z"-$R^{6''}$ represents a $C_{1-6}$ alkyl group, an aryl$C_{1-4}$ alkyl group (particularly wherein aryl represents phenyl or naphthyl), a heteroaryl$C_{1-4}$ alkyl group (particularly wherein heteroaryl represents 2-pyridyl, 3-pyridyl, 4-pyridyl or 1H-indol-3-yl), an aryloxy$C_{2-5}$ alkyl group or a pyrrolidinylcarbonyl$C_{1-4}$ alkyl group in which the aryl moiety of the said groups may be optionally substituted with a halogen atom, a $C_{1-6}$ alkyl group, a $C_{1-6}$ alkoxy group, a $C_{1-6}$ alkoxycarbonyl group or an amino group (compounds of formula (I)$^b$ are described in EP0760362A1).

A preferred set of compounds include compounds of formula (I) wherein $R^1$ represents $C_{1-6}$ alkyl, $C_{2-6}$ alkenyl, $C_{2-6}$ alkynyl, aryl-$Y^1$—, heteroaryl-$Y^1$—, aryl-(O)$_r$-aryl-$Y^1$—, aryl-(O)$_r$-heteroaryl-$Y^1$—, heteroaryl-(O)$_r$-aryl-$Y^1$—, heteroaryl-(O)$_r$-heteroaryl-$Y^1$—, aryl-$SO_2$—$Y^1$—, $C_{1-6}$ alkyl-G-$Y^1$—, $J^1$-$SO_2$—$Y^1$—, $R^{17}O(CO)$—$C_{2-6}$ alkenyl-$Y^1$—, $C_{2-6}$ alkynyl-$Y^1$—, $C_{2-6}$ alkenyl-$Y^1$—, aryl-O—$Y^1$—, heteroaryl-O—$Y^1$—, $C_{1-6}$ alkyl-$SO_2$—$Y^1$—, M-$Y^1$—, $J^1$-$Y^1$—, $J^1$-CO—$Y^1$—, aryl-CO—$Y^1$— or $C_{3-8}$ cycloalkyl-$Y^1$— or $C_{3-8}$ cycloalkenyl-$Y^1$—, which $C_{2-6}$ alkynyl and $C_{2-6}$ alkynyl-$Y^1$ may be optionally substituted with a —$OR^{17}$ group and which cycloalkyl or cycloalkenyl may be optionally substituted by one or more hydroxyl or $C_{1-6}$ alkyl groups;

$R^2$ represents hydrogen or $C_{1-6}$ alkyl; and $J^1$, $J^2$ and $J^3$ independently represent a moiety of formula (K):

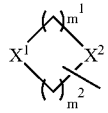

(K)

wherein $X^1$ represents oxygen, $NR^{11}$ or sulphur, $X^2$ represents $CH_2$, oxygen, $NR^{12}$ or sulphur, $m^1$ represents an integer from 1 to 3 and $m^2$ represents an integer from 1 to 3, provided that $m^1+m^2$ is in the range from 3 to 5, also provided that when both $X^1$ and $X^2$ represent oxygen, $NR^{11}$, $NR^{12}$ or sulphur, $m^1$ and $m^2$ must both not equal less than 2, wherein K is optionally substituted by one or more (eg. 1 or 2) —$Y^3$-aryl, —$Y^3$-heteroaryl, —$Y^3$—CO-aryl, —$Y^3$—CO-heteroaryl, —$C_{1-6}$ alkyl, —$Y^3$—$COOC_{1-6}$ alkyl, —$Y^3$—$COC_{1-6}$ alkyl, —$Y^3$—W, —$Y^3$—CO—W, —$Y^3$—$NR^{15}R^{16}$, —$Y^3$—$CONR^{15}R^{16}$, hydroxy, oxo, —$Y^3$—$SO_2NR^{15}R^{16}$, —$Y^3$—$SO_2C_{1-6}$ alkyl, —$Y^3$—$SO_2$aryl, —$Y^3$—$SO_2$heteroaryl, —$Y^3$—$NR^{13}C_{1-6}$ alkyl, —$Y^3$—$NR^{13}SO_2C_{1-6}$ alkyl, —$Y^3$—$NR^{13}CONR^{15}R^{16}$, —$Y^3$—$NR^{13}COOR^{14}$ or —$Y^3$—$OCONR^{15}R^{16}$ groups, and is optionally fused to a monocyclic aryl or heteroaryl ring;

A preferred subset of compounds include compounds of formula (I) wherein $R^1$ represents $C_{1-6}$ alkyl, $C_{2-6}$ alkenyl, $C_{2-6}$ alkynyl, aryl-$Y^1$—, heteroaryl-$Y^1$—, aryl-(O)$_r$-aryl-$Y^1$—, aryl-(O)$_r$-heteroaryl-$Y^1$—, heteroaryl-(O)$_r$-aryl-$Y^1$—, heteroaryl-(O)$_r$-heteroaryl-$Y^1$—, $C_{2-6}$ alkenyl-$Y^1$—, aryl-O—$Y^1$—, heteroaryl-O—$Y^1$—, $C_{1-6}$ alkyl-$SO_2$—$Y^1$—, M-$Y^1$—, —$Y^1$-$J^1$, —$Y^1$—CO-$J^1$ or $C_{3-8}$ cycloalkyl-$Y^1$— or $C_{3-8}$ cycloalkenyl-$Y^1$—, which cycloalkyl or cycloalkenyl may be optionally substituted by one or more hydroxyl or $C_{1-6}$ alkyl groups;

R² represents hydrogen or $C_{1-6}$ alkyl;

Z represents a bond, CO, $CR^{10}R^7(CH_2)_n$, $CHR^7(CH_2)_nO$, $CHR^7(CH_2)_nS$, $CHR^7(CH_2)_nOCO$, $CHR^7(CH_2)_nCO$; and $J^1$, $J^2$ and $J^3$ independently represent a moiety of formula (K):

wherein $X^1$ represents oxygen, nitrogen, $NR^{11}$ or sulphur, $X^2$ represents $CH_2$, oxygen, nitrogen, $NR^{12}$ or sulphur, $m^1$ represents an integer from 1 to 3, $m^2$ represents an integer from 1 to 3, provided that $m^1+m^2$ is in the range from 3 to 5, also provided that when $X^2$ represents oxygen, nitrogen, $NR^{12}$ or sulphur, $m^1$ and $m^2$ must both not equal less than 2, wherein K is optionally substituted by one or more (eg. 1 or 2) —$Y^3$-aryl, —$Y^3$-heteroaryl, —$Y^3$—CO-aryl, —$Y^3$—CO-heteroaryl, —$C_{1-6}$ alkyl, —$Y^3$—$COOC_{1-6}$ alkyl, —$Y^3$—$COC_{1-6}$alkyl, —$Y^3$—W, —$Y^3$—CO—W, —$Y^3$—$NR^{15}R^{16}$, —$Y^3$—$CONR^{15}R^{16}$, hydroxy, oxo, —$Y^3$—$SO_2NR^{15}R^{16}$, —$Y^3$—$SO_2C_{1-6}$ alkyl, —$Y^3$—$SO_2$aryl, —$Y^3$—$SO_2$heteroaryl, —$Y^3$—$NR^{13}C_{1-6}$ alkyl, —$Y_3$—$NR^{13}SO_2C_{1-6}$ alkyl, —$Y^3$—$NR^{13}CONR^{15}R^{16}$, —$Y^3$—$NR^{13}COOR^{14}$ or —$Y^3$—$OCONR^{15}R^{16}$ groups, and is optionally fused to a monocyclic aryl or heteroaryl ring;

References to 'aryl' include references to monocyclic carbocyclic aromatic rings (eg. phenyl) and bicyclic carbocyclic aromatic rings (e.g. naphthyl) and references to 'heteroaryl' include references to mono- and bicyclic heterocyclic aromatic rings containing 1–3 hetero atoms selected from nitrogen, oxygen and sulphur. References to 'heteroaryl' may also be extended to include references to mono- and bicyclic heterocyclic aromatic rings containing 4 hetero atoms selected from nitrogen, oxygen and sulphur. Examples of monocyclic heterocyclic aromatic rings include e.g. pyridinyl, pyrimidinyl, thiophenyl, furanyl, pyrrolyl, oxazolyl, isoxazolyl, oxadiazolyl, thiazolyl, thiadiazolyl. Further examples of monocyclic heterocyclic aromatic rings include pyrazinyl, tetrazolyl or imidazolyl. Examples of bicyclic heterocyclic aromatic rings include eg. quinolinyl or indolyl. Further examples of bicyclic heterocyclic aromatic rings include benzimidazolyl. Yet further examples of bicyclic heterocyclic aromatic rings include dihydrobenzofuranyl and pyrrolopyridinyl. Carbocyclic and heterocyclic aromatic rings may be optionally substituted, e.g. by one or more $C_{1-6}$ alkyl, $C_{2-6}$ alkenyl, halogen, $C_{1-6}$ alkoxy, cyano, hydroxy, nitro, amino, W, —$N(CH_3)_2$, —$NHCOC_{1-6}$ alkyl, —$OCF_3$, —$CF_3$, —$COOC_{1-6}$ alkyl, —$OCHF_2$, —$SCF_3$, —$CONR^{19}R^{20}$, —$SO_2NR^{19}R^{20}$ (wherein $R^{19}$ and $R^{20}$ independently represent hydrogen, $C_{1-6}$ alkyl or $C_{3-8}$ cycloalkyl), —$NHSO_2CH_3$, —$SO_2CH_3$ or —$SCH_3$ groups. A further substituent of carbocyclic and heterocyclic aromatic rings may be —COOH. Yet further substituents of carbocyclic and heterocyclic aromatic rings may be —$CH_2N(CH_3)_2$ or one or more —SH groups, wherein it will be appreciated that said group may tautomerise to form an ═S group.

Examples of group M include tetrahydronaphthalenyl.

Examples of group W include piperidinyl, pyrrolidinyl, morpholinyl and piperazinyl which may be optionally substituted with one or more $C_{1-6}$ alkyl, halogen, or hydroxy groups.

Examples of group $J^1$ include N—($COOCH_2CH_3$)-piperidin-4-yl, N—($CH_3$)-piperidin-4-yl, N—($COCH_3$)-piperidin-4-yl, pyrrolidin-1-yl, tetrahydropyran-4-yl or N-morpholinyl. Further examples of group $J^1$ include N-(cyclopropylcarbonyl)-piperidin-4-yl, N-(methylsulphonyl)-piperidin-4-yl, thiopyranyl and tetrahydrothienyl.

Examples of group $J^2$ include (4-phenyl)-piperidin-1-yl, (4-$COOCH_2CH_3$)-piperazin-1-yl, (2-(3-hydroxy-pyrrolidin-1-yl-methyl))-piperidin-1-yl, N-morpholinyl, (4—$N(CH_3)_2$)-piperidin-1-yl, (4-(3-fluorophenyl))-piperazin-1-yl, (4-(4-fluorophenyl))-piperazin-1-yl, (4-pyrimidinyl)-piperazin-1-yl, (4-$CH_3$)-piperazin-1-yl, (4-$CONH_2$)-piperidin-1-yl, (3,3-dimethyl)-piperidin-1-yl, (4-$COCH_3$)-piperazin-1-yl, (4-(1-pyrrolidinyl-carbonylmethyl))-piperazin-1-yl, (4-hydroxy)-piperidin-1-yl, (4-methyl)-piperidin-1-yl, (4-(2-furanyl-carbonyl))-piperazin-1-yl, (4-benzyl)-piperazin-1-yl or (3-$CH_3SO_2CH_2$—)-morpholin-1-yl. Further examples of group $J^2$ include thiomorpholinyl, pyrrolidinyl and benzazepinyl.

Examples of group $J^3$ include indolinyl, which may be optionally substituted.

References to alkyl include references to both straight chain and branched chain aliphatic isomers of the corresponding alkyl. It will be appreciated that references to alkylene and alkoxy shall be interpreted similarly.

References to $C_{3-8}$ cycloalkyl include references to all alicyclic (including branched) isomers of the corresponding alkyl.

Preferably, $R^1$ represents $C_{1-6}$ alkyl (particularly propyl), $C_{2-6}$ alkenyl (particularly wherein said $C_{2-6}$ alkenyl is substituted by one or more —$COOR^{17}$ groups, eg. —HC═CH—COOH), $C_{2-6}$ alkynyl, aryl-$Y^1$—, heteroaryl-$Y^1$— (particularly wherein heteroaryl represents thiazolyl, indolyl, furanyl, dihydrobenzofuran, oxoimidazolyl, isoxazolyl, thienyl, thioxodihydroimidazolyl, tetrazolyl, pyrazinyl, pyrrolopyridinyl), aryl-(O)$_r$-aryl-$Y^1$—, aryl-(O)$_r$-heteroaryl-$Y^1$— (particularly wherein aryl represents phenyl and heteroaryl represents thiadiazolyl, pyrazolyl or isoxazolyl), heteroaryl-(O)$_r$-aryl-$Y^1$—, heteroaryl-(O)$_r$-heteroaryl-$Y^1$—, $C_{2-6}$ alkenyl-$Y^1$—, aryl-O—$Y^1$— (particularly wherein aryl represents phenyl), heteroaryl-O—$Y^1$—, $C_{1-6}$ alkyl-$SO_2$—$Y^1$— (particularly wherein $C_{1-6}$ alkyl represents ethyl, propyl, —$CH(CH_3)_2$ or —$C(CH_3)_3$), M-$Y^1$—, $J^1$-$Y^1$—, $J^1$-CO—$Y^1$—, aryl-$SO_2$—$Y^1$—, $C_{1-6}$ alkyl-G-$Y^1$— (particularly wherein $C_{1-6}$ alkyl represents methyl and G represents —$NR^{18}CO$—, —$CONR^{18}$—, —$NR^{18}SO_2$— or -$SO_2NR^{18}$—), heteroaryl-G-aryl-$Y^1$— (particularly wherein aryl represents phenyl and heteroaryl represents thiazolyl and G represents —$NR^{18}SO_2$—), $J^1$-$SO_2$—$Y^1$— (particularly wherein $J^1$ represents 1-pyrrolidinyl), $R_{17}O$(CO)—$C_{2-6}$ alkenyl-$Y^1$—, $R^{17}NHCO$—$Y^1$— (particularly wherein $R^{17}$ represents hydrogen), $C_{2-6}$ alkynyl-$Y^1$— (particularly —C≡CH or wherein said $C_{2-6}$ alkynyl is substituted with a —$OR^{17}$ group, eg. $HOCH_2$—C≡C—), aryl-CO—$Y^1$— (particularly wherein aryl represents phenyl), $C_{3-8}$ cycloalkyl-$Y^1$— or $C_{3-8}$ cycloalkenyl-$Y^1$—, which cycloalkyl or cycloalkenyl may be optionally substituted by one or more hydroxyl or $C_{1-6}$ alkyl groups and which $C_{2-6}$ alkynyl-$Y^1$— may be optionally substituted with a —$OR^{17}$ group.

More preferred $R^1$ groups include $C_{1-6}$ alkyl, $C_{2-6}$ alkenyl, $C_{2-6}$ alkynyl, aryl-$Y^1$—, heteroaryl-$Y^1$—, aryl-(O)$_r$-aryl-$Y^1$—, aryl-(O)$_r$-heteroaryl-$Y^1$—, heteroaryl-(O)$_r$-aryl-$Y^1$—, heteroaryl-(O)$_r$-heteroaryl-$Y^1$—, $C_{2-6}$ alkenyl-$Y^1$—, aryl-O—$Y^1$—, heteroaryl-O—$Y^1$—, $C_{1-6}$ alkyl-$SO_2$—$Y^1$—, M-$Y^1$—, $J^1$-$Y^1$—, $J^1$—CO—$Y^1$— or $C_{3-8}$ cycloalkyl-$Y^1$— or $C_{3-8}$ cycloalkenyl-$Y^1$—, which cycloalkyl or cycloalkenyl may be optionally substituted by one or more hydroxyl or $C_{1-6}$ alkyl groups.

Yet more preferably, $R^1$ represents aryl-$Y^1$—, heteroaryl-$Y^1$, aryl-(O)$_t$-aryl-$Y^1$—, $C_{3-8}$ cycloalkyl-$Y^1$—, $C_{2-6}$ alkenyl-$Y^1$— or $C_{1-6}$ alkyl-$SO_2$—$Y^1$— especially wherein aryl represents phenyl or naphthyl optionally substituted by one or more $C_{1-6}$ alkyl (especially methyl), halogen (especially chlorine, fluorine and bromine), $CH_3O$—, $CH_3S$—, $F_2CHO$—, $CH_3OC(O)$—, —CN, —$CF_3$, $CF_3$—S—, $CF_3$—O—, or $(CH_3)_2N$—, groups, and wherein heteroaryl represents pyridinyl optionally substituted by one or more halogen atoms (especially chlorine) and wherein cycloalkyl represents cyclohexyl. Further preferred substituents of phenyl include —$NHCOCH_3$ and —$CONH_2$. Yet further preferred substituents of phenyl include —$SO_2NH_2$, —CONHCH$_3$, —OCH(CH$_3$)$_2$, —OC(CH$_3$)$_3$, —COOH, —CON(CH$_3$)$_2$, —SO$_2$CH$_3$, —CONHCH$_2$CH$_3$, —CONHcyclopropyl and —SO$_2$NHcyclopropyl. Also preferably, $R^1$ represents $C_{2-6}$ alkynyl-$Y^1$—. A series of particularly preferred compounds are those wherein $R^1$ represents aryl-$Y^1$— wherein aryl represents phenyl optionally substituted by one or more $C_{1-6}$ alkyl (especially methyl), halogen (especially chlorine, fluorine and bromine), $CH_3O$—, $CH_3S$—, $F_2CHO$—, $CH_3OC(O)$—, —CN or —$CF_3$ groups. Further most preferred substituents of phenyl include —NHCOCH$_3$ and —CONH$_2$. A yet further most preferred substituent of phenyl includes $SO_2NH_2$. Most preferably, $R^1$ will also represent $C_{2-6}$ alkenyl-$Y^1$— (particularly $CH_2$=CH—$Y^1$—), $C_{3-8}$ cycloalkyl-$Y^1$— (particularly cyclohexyl-$Y^1$—) and $C_{1-6}$ alkyl-$SO_2Y^1$— (particularly $CH_3SO_2$—$Y^1$—). Also most preferably, $R^1$ represents $C_{2-6}$ alkynyl-$Y^1$— (particularly HC≡C—$Y^1$).

Especially preferred $R^1$ groups are aryl-$Y^1$— and heteroaryl-$Y^1$—, most especially wherein aryl represents phenyl and heteroaryl represents a 6 membered monocyclic heterocyclic aromatic ring (most particularly tetrazolyl) each of which may be optionally substituted as indicated above.

Preferred substituents of heteroaryl include —CH$_3$, —CONH$_2$, —CH$_2$N(CH$_3$)$_2$, halogen (particularly chlorine), —OCH$_3$, —COOCH$_3$ and —NH$_2$.

Most especially preferred compounds are those wherein $R^1$ represents phenyl-$Y^1$— which phenyl is substituted with a —CONH$_2$ or —CONHCH$_3$ group and tetrazolyl-$Y^1$— which tetrazolyl is substituted with a methyl group.

Preferably, $Y^1$ represents a bond or $C_{1-6}$ alkylene, more preferably a bond, methylene or ethylene, propylene, —C(CH$_3$)$_2$— or —CH(CH$_3$)—, particularly a bond, methylene or ethylene, most preferably a bond or methylene, especially methylene.

Preferably, $Y^2$ represents a bond.

Preferably, $Y^3$ represents a bond.

Preferably, $R^2$ represents hydrogen, methyl or hydroxypropyl, more preferably hydrogen or methyl, especially hydrogen.

Preferably, $R^3$ represents hydrogen or methyl, especially hydrogen.

Also preferably, $R^1$ and $R^2$ together with the nitrogen atom to which they are attached form a group of formula $J^2$ wherein said nitrogen atom substitutes for either $X^1$ or $X^2$.

Preferably, X represents methylene.

Preferably, $R^4$ and $R^5$ independently represent hydrogen or methyl. Most preferably, $R^4$ and $R^5$ represent hydrogen.

Preferably, Z represents a bond, CO, CR$^{10}$R$^7$(CH$_2$)$_n$, CHR$^7$(CH$_2$)$_n$O, CHR$^7$(CH$_2$)$_n$S, CHR$^7$(CH$_2$)$_n$OCO or CHR$^7$(CH$_2$)$_n$CO.

More preferably, Z represents CO, CHR$^7$(CH$_2$)$_n$, CHR$^7$(CH$_2$)$_n$O, CHR$^7$(CH$_2$)$_n$S, CHR$^7$(CH$_2$)$_n$OCO or CHR$^7$(CH$_2$)$_n$ CO, especially CH$_2$CO, (CH$_2$)$_2$, (CH$_2$)$_2$S, (CH$_2$)$_2$O, (CH$_2$)$_2$ OCO, (CH$_2$)$_3$CO, CO, CHR$^7$, particularly CH$_2$, CHCH$_3$ or CH$_2$CO, most particularly CH$_2$ or CH$_2$CO, especially CH$_2$.

Preferably, $R^6$ represents $C_{1-6}$ alkyl, $C_{2-6}$ alkenyl, CN, aryl, heteroaryl or a group of formula —$Y^2$-$J^3$, more preferably $R^6$ represents phenyl (optionally substituted with one or more halogen, phenyl or $C_{2-6}$ alkenyl groups), naphthyl, $C_{1-6}$ alkyl, $C_{2-6}$ alkenyl, CN or a 5 membered aromatic heterocyclic ring containing 1 to 3 heteroatoms selected from O, N or S optionally substituted by halogen or $C_{1-6}$ alkyl. Especially, $R^6$ represents phenyl (optionally substituted with one or more halogen (especially chlorine, fluorine or iodine), phenyl or 3—CH=CH$_2$ groups), naphthyl, indolinyl, methyl, —CH=CH$_2$, —CN or thiophenyl optionally substituted by halogen (especially chlorine). Most preferred $R^6$ represents indolinyl (especially indolin-1-yl) or else represents phenyl substituted by one or more halogen (eg. chlorine or fluorine) groups, particularly dichlorophenyl, 3-chlorophenyl, 5-chlorothiophenyl, 4-fluorophenyl and 3,4-difluorophenyl, most particularly dichlorophenyl, especially 3,4-dichlorophenyl.

Preferably, $R^7$ represents hydrogen, methyl, COOC$_{1-6}$ alkyl or CONR$^8$R$^9$, more preferably hydrogen, COOC$_{1-6}$ alkyl or CONR$^8$R$^9$ most preferably hydrogen, COOEt or CONR$^8$R$^9$, especially hydrogen.

Preferably, $R^8$ and $R^9$ represent hydrogen.

Preferably, $R^{10}$ represents hydrogen.

Preferably, $R^{11}$ and $R^{12}$ independently represent hydrogen or methyl.

Preferably, $R^{13}$ and $R^{14}$ independently represent hydrogen or methyl.

Preferably, $R^{15}$ and $R^{16}$ independently represent hydrogen or methyl or $R^{15}$ and $R^{16}$ together with the nitrogen atom to which they are attached may form a morpholine, piperidine or pyrrolidine ring, especially hydrogen or methyl.

Preferably, $R^{17}$ represents hydrogen.

Preferably, $R^{18}$ represents hydrogen.

Preferably, $R^{19}$ and $R^{20}$ independently represent hydrogen, $C_{1-6}$ alkyl or $C_{3-8}$ cycloalkyl, especially hydrogen, cyclopropyl or methyl. Particularly, $R^{19}$ and $R^{20}$ represent hydrogen.

Preferably, $R^c$ represents hydrogen or methyl, particularly hydrogen.

Preferably, $R^d$ represents hydrogen or methyl, particularly hydrogen.

Preferably, a and b both represent 1.

Preferably, n represents 0, 1 or 2.

Preferably, p+q equals an integer from 0 to 2, more preferably, p and q independently represent 0 or 1 such that p+q equals an integer from 0 to 1.

Preferably, t represents 0.

Preferably, W represents pyrrolidinyl or piperidinyl, especially pyrrolidinyl.

Preferably, $X^1$ represents oxygen, nitrogen or NR$^{11}$.

Preferably, $X^2$ represents CH$_2$, oxygen, nitrogen or NR$^{12}$.

Preferably, $m^1$ and $m^2$ independently represent an integer from 1 to 2, such that $m^1$+$m^2$ is in the range from 3 to 4.

Preferably, $J^1$ represents piperidinyl (particularly piperidin-4-yl) or tetrahydropyranyl (particularly tetrahydropyran-4-yl) optionally substituted by one or two —COOCH$_2$CH$_3$, —COOtBu, —CH$_3$, —COCH$_3$, —SO$_2$N(CH$_3$)$_2$, —SO$_2$CH$_3$, —COPhenyl or 3, 5-dimethylisoxazol-4-ylsulphonyl groups. Also preferably, $J^1$ represents morpholinyl, thiopyranyl or tetrahydrothienyl which may be optionally substituted as above (particularly dioxidotetrahydrothienyl).

Preferred substituents for $J^1$ include —$CH_2$-aryl (particularly wherein aryl represents phenyl optionally substituted with one or more halogen atoms, eg. dichlorophenyl), —COcyclopropyl or —$Y^3$—$SO_2$heteroaryl (particularly wherein heteroaryl represents dimethylisoxazolyl).

Preferably, $J^2$ represents piperidinyl (particularly piperidin-1-yl), morpholinyl (particularly N-morpholinyl) or piperazinyl (particularly piperazin-1-yl) optionally substituted by one or two phenyl, —$COOCH_2CH_3$, —$N(CH_3)_2$, fluorophenyl, —$CH_3$, —$CONH_2$, —$COCH_3$, —$CH_2CO$—(N-pyrrolidinyl), hydroxy, —CO-(2-furan), benzyl or —$CH_2SO_2CH_3$. Preferably, $J^2$ also represents thiomorpholinyl, pyrrolidinyl or benzazepinyl optionally substituted in a similar manner.

Other preferred substituents for $J^2$ include halogen (particularly fluorine), —$COOCH_2CH_3$, —CO-furoyl, —$SO_2CH_3$, -pyridinyl-$CH_3$ or oxo groups.

Preferably, $J^3$ represents indolinyl, particularly indolin-1-yl.

Suitable salts of the compounds of formula (I) include physiologically acceptable salts and salts which may not be physiologically acceptable but may be useful in the preparation of compounds of formula (I) and physiologically acceptable salts thereof. If appropriate, acid addition salts may be derived from inorganic or organic acids, for example hydrochlorides, hydrobromides, sulphates, phosphates, acetates, benzoates, citrates, succinates, lactates, tartrates, fumarates, maleates, 1-hydroxy-2-naphthoates, palmoates, methanesulphonates, formates or trifluoroacetates. Examples of solvates include hydrates.

When compounds of formula (I) contain chiral centres, the invention extends to mixtures of enantiomers (including racemic mixtures) and diastereoisomers as well as to individual enantiomers. Generally it is preferred to use a compound of formula (I) in the form of a single enantiomer.

The compounds of formula (I) and salts and solvates thereof may be prepared by the methodology described hereinafter, constituting a further aspect of this invention.

A process according to the invention for preparing a compound of formula (I) comprises:

(a) reacting a compound of formula (II)

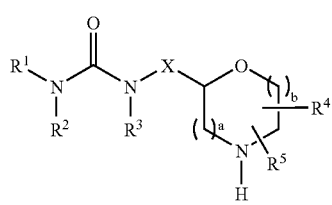

(II)

wherein $R^1$, $R^2$, $R^3$, $R^4$, $R^5$, X, a and b are as defined above, or a protected derivative thereof, with a compound of formula $L^1$-Z-$R^6$, wherein Z and $R^6$ are as defined above and $L^1$ represents a suitable leaving group; or (b) forming a compound of formula (I) wherein $R^2$ represents hydrogen which comprises reacting a compound of formula (III)

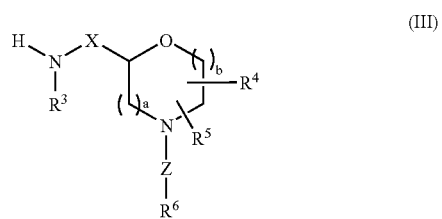

(III)

wherein $R^3$, $R^4$, $R^5$, $R^6$, Z, X, a and b are as defined above, or a protected derivative thereof, with a compound of formula $R^1$—N═C═O, wherein $R^1$ is as defined above; or (c) reacting a compound of formula (IV)

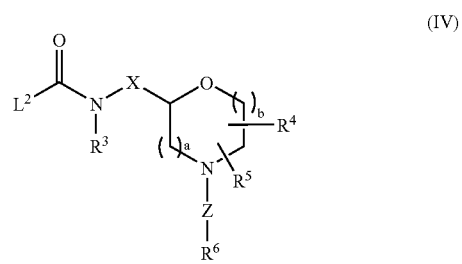

(IV)

wherein $R^3$, $R^4$, $R^5$, $R^6$, Z, X, a and b are as defined above or a protected derivative thereof and $L^2$ represents a suitable leaving group, or a protected derivative thereof, with a compound of formula (V)

(V)

wherein $R^1$ and $R^2$ are as defined above or a protected derivative thereof; or (d) reacting a compound of formula (VI)

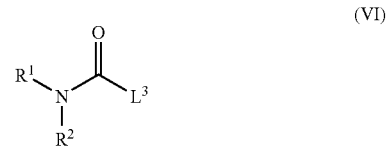

(VI)

wherein $R^1$ and $R^2$ are as defined above and $L^3$ represents a suitable leaving group, or a protected derivative thereof, with a compound of formula (III), or a protected derivative thereof; or (e) deprotecting a compound of formula (I) which is protected; or (f) interconversion of other compounds of formula (I).

We also provide a further process according to the invention for preparing a compound of formula (I) which comprises:

(g) forming a compound of formula (I) wherein $R^1$ and $R^2$ together with the nitrogen atom to which they are attached form a group of formula J² wherein said nitrogen atom substitutes for either X¹ or X² which comprises reacting a compound of formula (IV) or a protected derivative thereof with a compound of formula J²H, provided that the compound of formula J²H has a free —NH group; or (h) forming a compound of formula (I) wherein Z represents CR¹⁰R⁷(CH₂)ₙ, wherein R¹⁰ represents hydrogen, which comprises reacting a compound of formula (II) or a protected derivative thereof with a compound of formula R⁷CO(CH₂)ₙR⁶, followed by reduction of the resultant imine; or (i) forming a compound of formula (I) wherein R¹ represents C₁₋₆ alkyl-G-Y¹—, wherein G represents —NR¹⁸CO—, which comprises reacting a compound of formula (VII)

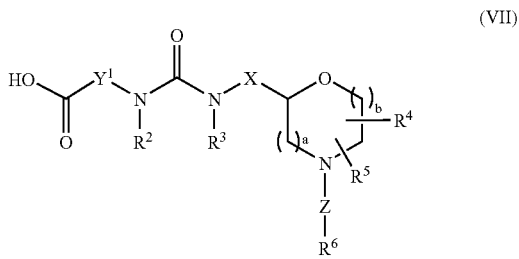

(VII)

or a protected derivative thereof wherein R², R³, R⁴, R⁵, R⁶, Y¹ X, Z, a and b are as defined above, with a compound of formula C₁₋₆ alkyl-NHR¹⁸.

Process (a) may be performed in the presence of an inert solvent eg. N,N-dimethylformamide optionally in the presence of a base such as N,N-diisopropylethylamine at a suitable temperature eg. room temperature. Examples of suitable leaving groups (L¹) include halogen, eg. chlorine.

Process (b) may be performed in the presence of an inert solvent eg dichloromethane at a suitable temperature eg. room temperature.

Processes (c) and (d) may typically be performed in the presence of a suitable base eg. pyridine at a suitable temperature e.g. 110° C., wherein leaving groups L² and L³ may represent 4-nitrophenoxy. Alternatively, when L² and L³ represent 4-nitrophenoxy, suitable conditions may involve the use of N,N-diisopropylethylamine as a suitable base and dichloromethane or N,N-dimethylformamide as a suitable solvent. Alternatively, where L² and L³ are Merrifield resin bound 4-thiophenoxy, processes (c) and (d) may be performed with a suitable additive e.g. N-methylpyrrolidinone in a microwave oven, for example at a power of 600W for 5 min. Other suitable leaving groups include imidazolyl. Wherein L² or L³ represent imidazolyl, suitable conditions comprise the use of 1,1'-carbonyldiimidazole in suitable solvents such as dichloromethane and N,N-dimethylformamide at a suitable temperature, e.g. between 0° C. and 22° C.

In process (e), examples of protecting groups and the means for their removal can be found in T. W. Greene and P. G. M. Wuts 'Protective Groups in Organic Synthesis' (J. Wiley and Sons, 3rd Ed. 1999). Suitable amine protecting groups include sulphonyl (e.g. tosyl), acyl (e.g. benzyloxycarbonyl or t-butoxycarbonyl) and arylalkyl (e.g. benzyl), which may be removed by hydrolysis or hydrogenolysis as appropriate. Other suitable amine protecting groups include trifluoroacetyl (—COCF₃) which may be removed by base catalysed hydrolysis or a solid phase resin bound benzyl group, such as a Merrifield resin bound 2,6-dimethoxybenzyl group (Ellman linker) or a 2,6-dimethoxy-4-[2-(polystyrylmethoxy)ethoxy]benzyl group, which may be removed by acid catalysed hydrolysis, for example with trifluoroacetic acid.

Process (f) may be performed using conventional interconversion procedures such as epimerisation, oxidation, reduction, alkylation, nucleophilic aromatic substitution, ester hydrolysis or amide bond formation. Alternative conditions for process (f) include t-butoxycarbonyl group addition or removal and sulphonylation.

Process (g) may be performed in an identical manner to the conditions described above for processes (c) and (d).

Process (h) may be performed in the presence of a suitable acid, eg. acetic acid and a suitable reducing agent, eg. sodium triacetoxyborohydride in a suitable solvent, eg. dichloromethane at a suitable temperature, eg. room temperature.

Process (i) may be performed in the presence of a suitable coupling reagent, eg. 1,1'-carbonyldiimidazole and a suitable solvent, eg. N,N-dimethylformamide at a suitable temperature, eg. room temperature.

Compounds of formula (II) as the R-isomer, wherein R² and R³ both represent hydrogen, X represents methylene, a and b represent 1 and R⁴ and R⁵ both represent hydrogen may be prepared according to the following process:

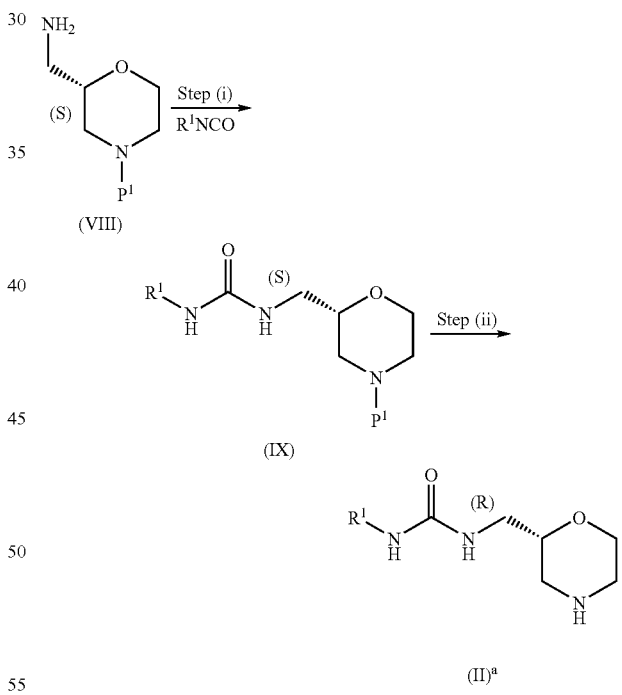

wherein R¹ is as defined above and P¹ is a suitable protecting group, eg. benzyl.

Compounds of formula (VIII) may be prepared as described in EP0995746.

Step (i) typically comprises the use of an inert solvent eg dichloromethane at a suitable temperature eg. room temperature. Step (ii) typically comprises a simple deprotection reaction, eg. which may comprise the use of 10% palladium on activated carbon in the presence of ammonium formate and a suitable solvent, eg. ethanol.

Compounds of formula (II)$^a$ as the S-isomer, wherein R$^1$ is as defined above, may be prepared by an analogous process.

Compounds of formula (IV) may be prepared according to the following process:

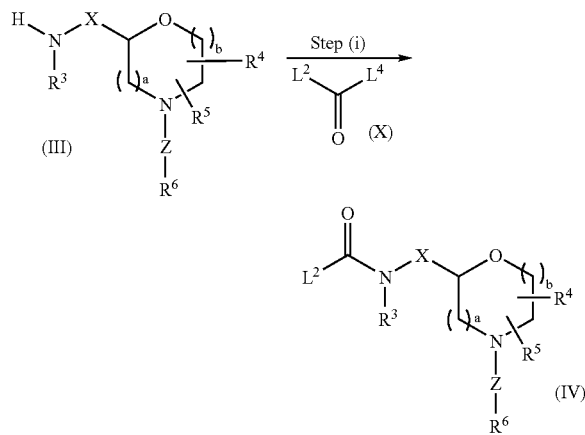

wherein R$^3$, R$^4$, R$^5$, R$^6$, X, a, b and Z are as defined above and L$^2$ represents a suitable leaving group as defined above eg. 4-nitrophenoxy or Merrifield resin bound 4-thiophenoxy and L$^4$ represents a leaving group more labile than L$^2$ eg. chlorine or 4-nitrophenoxy. When L$^2$ represents 4-nitrophenoxy and L$^4$ represents chlorine, step (i) may be carried out in a suitable solvent such as dichloromethane in the presence of a base such as triethylamine at a suitable temperature such as room temperature. When L$^2$ represents Merrifield resin bound 4-thiophenoxy and L$^4$ represents 4-nitrophenoxy, step (i) may be carried out in a suitable solvent such as N,N-dimethylformamide at a suitable temperature such as room temperature. Alternatively L$^2$ and L$^4$ may represent imidazole, wherein step (i) may be carried out with 1,1'-carbonyldiimidazole, in a suitable solvent e.g. a mixture of dichloromethane and N,N'-dimethylformamide at a suitable temperature e.g. between 0° C. and 22° C.

Compounds of formula (III) may be used in protected form, eg. wherein the amine group is protected when R$^3$ represents hydrogen. Suitable protecting groups are among those described above.

Compounds of formula (III) may be prepared according to the following process:

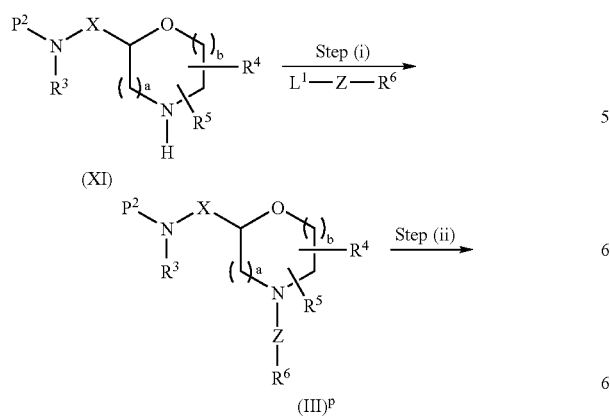

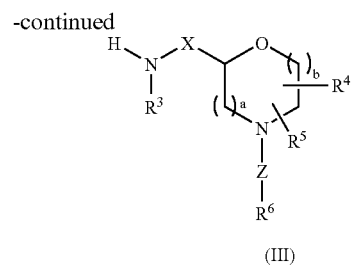

wherein R$^3$, R$^4$, R$^5$, R$^6$, X, a, b and Z are as defined above and L$^1$ represents a suitable leaving group eg. chlorine and P$^2$ represents a suitable protecting group eg. one mentioned above, such as —COCF$_3$. Step (i) comprises the use of a suitable solvent eg. N,N-dimethylformamide in the presence of suitable reagents eg. sodium iodide and potassium carbonate at a suitable temperature eg. room temperature. Step (ii) comprises deprotection under conventional conditions appropriate for the protecting groups. When P$^2$ represents —COCF$_3$, deprotection may be achieved by the use of water and methanol in the presence of potassium carbonate at room temperature. Compounds of formula (III) wherein Z represents CR$^{10}$R$^7$(CH$_2$)$_n$ (wherein R$^{10}$ represents hydrogen), may also be prepared by reductive amination of compounds of formula (XI) in an analogous manner to that described in process (h) above.

Compounds of formula (III) wherein R$^3$ represents hydrogen, X represents methylene, a and b represent 1 and R$^4$ and R$^5$ are both attached to the morpholine ring at the 5-position may be prepared according to the following process:

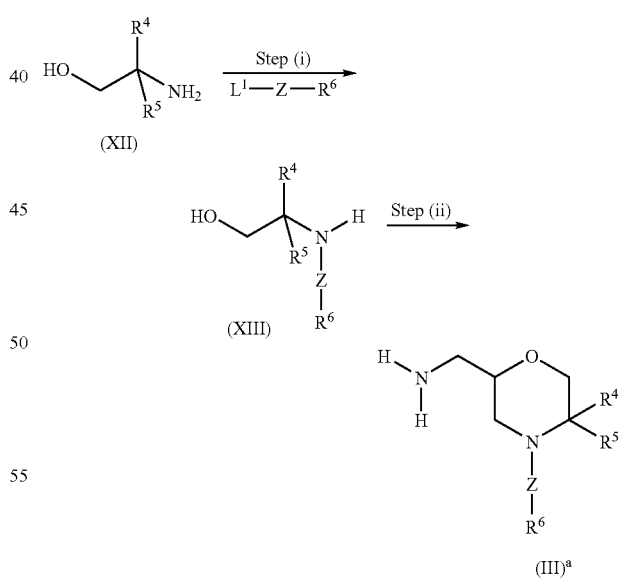

wherein R$^6$ and Z are as defined above and L$^1$ represents a suitable leaving group eg. chlorine. Step (i) comprises heating in the absence of solvent at between 50 and 60° C. Step (ii) comprises heating with 2-(oxiran-2-ylmethyl)-1H-isoindole-1,3(2H)-dione at 80° C. under nitrogen, followed by stirring with concentrated sulphuric acid at 150° C.

Compounds of formula (III) wherein $R^3$ represents H may be prepared according to the following process:

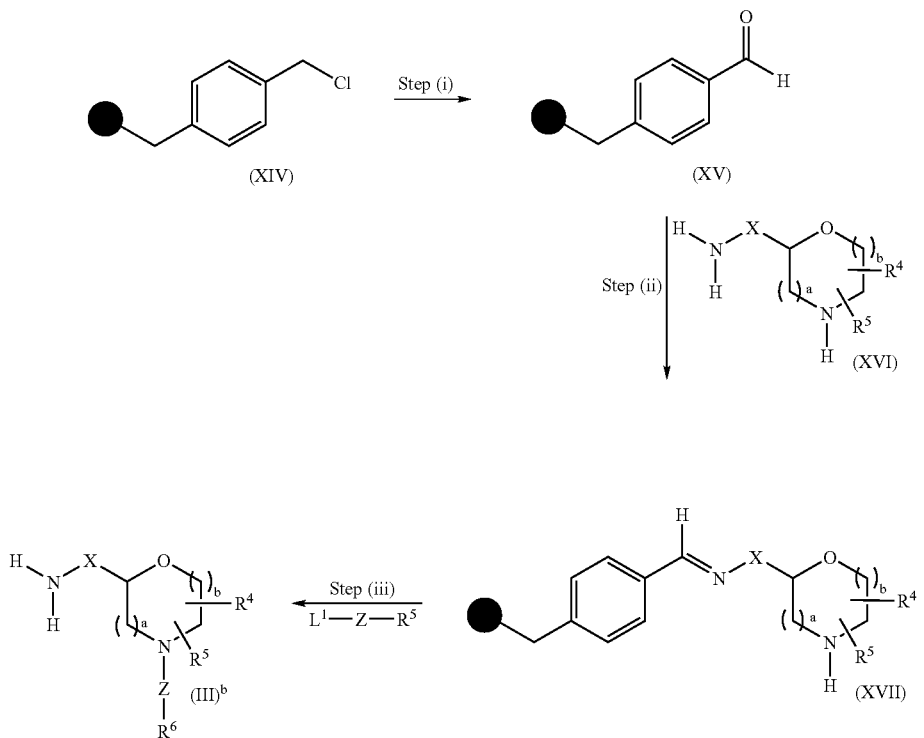

wherein $R^4$, $R^5$, $R^6$, X, a, b and Z are as defined above and $L^1$ represents a suitable leaving group eg. chlorine. Step (i) comprises heating a compound of formula (XIV; Merrifield Resin) with sodium carbonate in a suitable solvent eg. dimethylsulphoxide at a suitable temperature eg. 150° C. Step (ii) comprises reacting a compound of formula (XV) with a compound of formula (XVI) in the presence of a suitable solvent eg. tetrahydrofuran at a suitable temperature eg. room temperature. Step (iii) comprises the use of suitable solvent eg. N,N-dimethylformamide and a suitable base eg. N,N-diisopropylethylamine at a suitable temperature eg. 70° C., followed by deprotection under conventional conditions appropriate for the Merrifield resin protecting group eg. acid catalysed hydrolysis.

Compounds of formula (VII) may be prepared according to the following process:

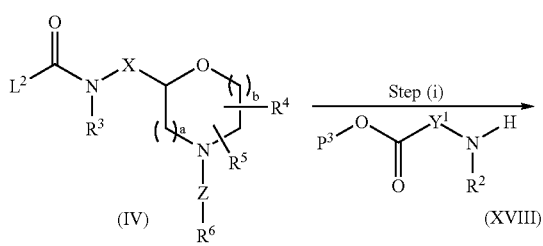

-continued

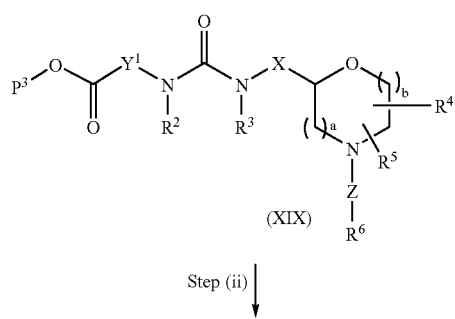

Step (ii) ↓

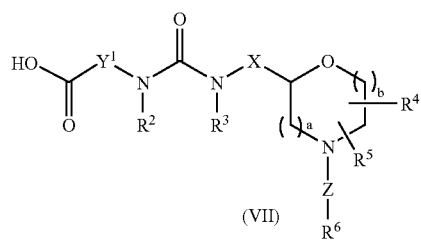

wherein $R^2$, $R^3$, $R^4$, $R^5$, $R^6$, $Y^1$, Z, X, a and b are as defined above, $L^2$ represents a suitable leaving group, eg. 4-nitrophenoxy and $P^3$ represents a suitable protecting group eg. $C_{1-6}$ alkyl, preferably t-butyl.

Step (i) typically comprises the use of a suitable base, eg. N,N-diisopropylethylamine and a suitable solvent, eg. dichloromethane at a suitable temperature, eg. room temperature.

Step (ii) typically comprises the use of a suitable acidic reagent, eg. 4M hydrogen chloride in dioxane at a suitable temperature, eg. room temperature.

Compounds of formula (V), (VI), (VIII), (X), (XI), (XII), (XIV), (XVI) and (XVIII) are either known or may be prepared in accordance with known procedures.

Compounds of formula $L^1$-Z-$R^6$, $R^1$N=C=O, $R^7$CO$(CH_2)_n R^6$, $C_{1-6}$ alkyl-NHR$^{18}$, and $J^2$-H are also either known or may be prepared in accordance with known procedures.

Compounds of formula (II) may be prepared in accordance with processes analogous to those described above for compounds of formula (I), employing standard protecting group chemistry. For example, employing suitable protection for the morpholine NH, such as t-butoxycarbonyl protection.

Compounds of formula (II), (III), (IV) and (VII) in protected and unprotected forms and salts and solvates thereof also form an aspect of the invention.

Compounds of the invention may be tested for in vitro and in vivo biological activity in accordance with the following assays:

(a) CCR-3 Binding Assay

A CCR-3 competition binding SPA (scintillation proximity assay) was used to assess the affinity of novel compounds for CCR-3. Membranes prepared from K562 cells stably expressing CCR-3 (2.5 μg/well) were mixed with 0.25 mg/well wheat-germ agglutinin SPA beads (Amersham) and incubated in binding buffer (HEPES 50 mM, $CaCl_2$ 1 mM, $MgCl_2$ 5 mM, 0.5% BSA) at 4° C. for 1.5 hr. Following incubation, 20 pM of [$^{125}$I] eotaxin (Amersham) and increasing concentrations of compound (1 pM to 30 μM) were added and incubated in a 96 well plate for 2 hr at 22° C. then counted on a Microbeta plate counter. The total assay volume was 100 μl. Competition binding data were analysed by fitting the data with a four parameter logistic equation. Data are presented as the mean $pIC_{50}$ values (negative logarithm of the concentration of compound which inhibits [$^{125}$I]eotaxin binding by 50%) from at least two experiments.

(b) Eosinophil Chemotaxis Assay.

Compounds were evaluated for their inhibitory effect on eosinophil chemotaxis. Eosinophils were purified from human peripheral blood by standard CD16 cell depletion using a Miltenyi cell separation column and a magnetic Super Macs magnet as previously described (Motegi & Kita, 1998; J. Immunology. 161:4340–6). Cells were re-suspended in RPMI 1640/10% FCS solution and incubated with calcein-AM (Molecular Probes) at 37° C. for 30 mins. Following incubation, the eosinophils were centrifuged at 400 g for 5 min and re-suspended in RPMI/FCS at 2.2 million/ml. Cells were then incubated in the presence of increasing concentration of compounds (1 pM to 30 μM) at 37° C. for 30 mins. For control responses cells were incubated with RPMI/FCS only. The agonist eotaxin (either a concentration response curve or for the functional inhibition curves an $EC_{80}$ concentration) was added to the lower chamber of a 96 well chemotaxis plate (5 μm filter: Receptor Technologies). Eosinophils (50 μl of 2 million/ml cells) were added to the top chamber of the filter plate and incubated at 37° C. for 45 mins. Cells remaining on top of the chemotaxis filter were removed and the number of eosinophils which had migrated were quantified by reading the plate on a fluorescent plate reader. Inhibition curves for the effect of compounds on eosinophil chemotaxis were analysed by fitting the data with a four parameter logistic equation. Functional $pK_i$ values ($fpK_i$) were generated using the equation below (Lazareno & Birdsall, 1995. Br. J. Pharmacol 109: 1110–9).

$$fpKi = \frac{IC_{50}}{1 + \left[\frac{[Agonist]}{EC_{50}}\right]}$$

(c) Guinea-pig Ovalbumin Model

Inhibition of Eosinophil Infiltration and Hyper-Reactivity in the Guinea Pig

In a method based on that described by Danahay et al., 1997, ovalbumin sensitised guinea pigs were dosed with mepyramine (30 mg kg$^{-1}$ ip) to protect against anaphylactic bronchospasm. Test compounds, dissolved in 10% DMSO and 90% PEG200, were given by the oral route, 30 minutes before ovalbumin challenge (10 minutes breathing of an aerosol generated from a 0.5% solution of ovalbumin). Hyper-reactivity of the airways to the thromboxane mimetic U46619, was measured 24 hours after ovalbumin challenge in unrestrained animals using a whole body plethysmograph (Buxco Ltd., USA). The guinea pigs were then sacrificed and the lungs lavaged. Total and differential leukocyte counts were then obtained for the bronchoalveolar lavage fluid and the percentage reduction in eosinophil accumulation determined (Sanjar et al., 1992). Data was presented as the inhibitory effect of the specified dose expressed as a percentage of the vehicle control response.

Examples of disease states in which the compounds of the invention have potentially beneficial anti-inflammatory effects include diseases of the respiratory tract such as bronchitis (including chronic bronchitis), asthma (including allergen-induced asthmatic reactions), chronic obstructive pulmonary disease (COPD) and rhinitis. Another disease of the respiratory tract in which the compounds of the invention have potentially beneficial effects is sinusitis. Other relevant disease states include diseases of the gastrointestinal tract such as intestinal inflammatory diseases including inflammatory bowel disease (e.g. Crohn's disease or ulcerative colitis) and intestinal inflammatory diseases secondary to radiation exposure or allergen exposure. Furthermore, compounds of the invention may be used to treat nephritis, skin diseases such as psoriasis, eczema, allergic dermatitis and hypersensitivity reactions and diseases of the central nervous system which have an inflammatory component eg. Alzheimer's disease, meningitis, multiple sclerosis and AIDS dementia. Compounds of the present invention may also be of use in the treatment of nasal polyposis, conjunctivitis or pruritis. Additionally, the compounds of the present invention may be of use in the treatment of viral diseases such as HIV.

Further examples of disease states in which compounds of the invention have potentially beneficial effects include cardiovascular conditions such as atherosclerosis, peripheral vascular disease and idiopathic hypereosinophilic syndrome. Other diseases for which the compounds of the present invention may be beneficial are other hypereosinophilic diseases such as Churg-strauss syndrome. Additionally, eosinophilia is commonly found in parasitic diseases, especially helminth infections, and thus the compounds of the present invention may be useful in treating inflammation arising from hyper-eosinophilic states of diseases such as hydatid cyst (*Echinococcus* sp.), tapeworm infections (*Tae-*

*nia* sp.), blood flukes (schistosomiasis), and nematode (round worms) infections such as: —Hookworm (*Ancylostoma* sp.), *Ascaris, Strongyloides, Trichinella*, and particularly lymphatic filariasis including *Onchocerca, Brugia, Wucheria* (Elephantiasis).

Compounds of the invention may be useful as immunosuppressive agents and so have use in the treatment of auto-immune diseases such as allograft tissue rejection after transplantation, rheumatoid arthritis and diabetes.

Compounds of the invention may also be useful in inhibiting metastasis.

Diseases of principal interest include asthma, COPD and inflammatory diseases of the upper respiratory tract involving seasonal and perennial rhinitis. Preferred diseases of principle interest include asthma and inflammatory diseases of the upper respiratory tract involving seasonal and perennial rhinitis. Further diseases also of principle interest include inflammatory diseases of the gastrointestinal tract such as inflammatory bowel disease.

It will be appreciated by those skilled in the art that reference herein to treatment extends to prophylaxis as well as the treatment of established conditions. As mentioned above, compounds of formula (I) are useful as pharmaceuticals, in particular as anti-inflammatory agents.

There is thus provided as a further aspect of the invention a compound of formula (I) or a physiologically acceptable salt or solvate thereof for use as pharmaceuticals, particularly in the treatment of patients with inflammatory conditions, eg. asthma or rhinitis.

According to another aspect of the invention, there is provided the use of a compound of formula (I) or a physiologically acceptable salt or solvate thereof for the manufacture of a medicament for the treatment of patients with inflammatory conditions, eg. asthma or rhinitis.

In a further or alternative aspect there is provided a method for the treatment of a human or animal subject with an inflammatory condition eg. asthma or rhinitis, which method comprises administering to said human or animal subject an effective amount of a compound of formula (I) or a physiologically acceptable salt or solvate thereof.

The compounds according to the invention may be formulated for administration in any convenient way, and the invention therefore also includes within its scope pharmaceutical compositions for use in anti-inflammatory therapy, comprising a compound of formula (I) or a physiologically acceptable salt or solvate thereof together, if desirable, with one or more physiologically acceptable diluents or carriers.

There is also provided a process for preparing such a pharmaceutical formulation which comprises mixing the ingredients.

The compounds according to the invention may, for example, be formulated for oral, inhaled, intranasal, buccal, parenteral or rectal administration, preferably for oral administration.

Tablets and capsules for oral administration may contain conventional excipients such as binding agents, for example syrup, acacia, gelatin, sorbitol, tragacanth, mucilage of starch, cellulose or polyvinyl pyrrolidone; fillers, for example, lactose, microcrystalline cellulose, sugar, maize-starch, calcium phosphate or sorbitol; lubricants, for example, magnesium stearate, stearic acid, talc, polyethylene glycol or silica; disintegrants, for example, potato starch, croscarmellose sodium or sodium starch glycollate; or wetting agents such as sodium lauryl sulphate. The tablets may be coated according to methods well known in the art. Oral liquid preparations may be in the form of, for example, aqueous or oily suspensions, solutions, emulsions, syrups or elixirs, or may be presented as a dry product for constitution with water or other suitable vehicle before use. Such liquid preparations may contain conventional additives such as suspending agents, for example, sorbitol syrup, methyl cellulose, glucose/sugar syrup, gelatin, hydroxymethyl cellulose, carboxymethyl cellulose, aluminium stearate gel or hydrogenated edible fats; emulsifying agents, for example, lecithin, sorbitan mono-oleate or acacia; non-aqueous vehicles (which may include edible oils), for example almond oil, fractionated coconut oil, oily esters, propylene glycol or ethyl alcohol; or preservatives, for example, methyl or propyl p-hydroxybenzoates or sorbic acid. The preparations may also contain buffer salts, flavouring, colouring and/or sweetening agents (e.g. mannitol) as appropriate.

For buccal administration the compositions may take the form of tablets or lozenges formulated in conventional manner.

The compounds may also be formulated as suppositories, e.g. containing conventional suppository bases such as cocoa butter or other glycerides.

The compounds according to the invention may also be formulated for parenteral administration by bolus injection or continuous infusion and may be presented in unit dose form, for instance as ampoules, vials, small volume infusions or pre-filled syringes, or in multi-dose containers with an added preservative. The compositions may take such forms as solutions, suspensions, or emulsions in aqueous or non-aqueous vehicles, and may contain formulatory agents such as anti-oxidants, buffers, antimicrobial agents and/or tonicity adjusting agents. Alternatively, the active ingredient may be in powder form for constitution with a suitable vehicle, e.g. sterile, pyrogen-free water, before use. The dry solid presentation may be prepared by filling a sterile powder aseptically into individual sterile containers or by filling a sterile solution aseptically into each container and freeze-drying.

The pharmaceutical compositions according to the invention may also be used in combination with other therapeutic agents, for example anti-inflammatory agents (such as corticosteroids (e.g. fluticasone propionate, beclomethasone dipropionate, mometasone furoate, triamcinolone acetonide or budesonide) or NSAIDs (eg. sodium cromoglycate, nedocromil sodium, PDE-4 inhibitors, leukotriene antagonists, iNOS inhibitors, tryptase and elastase inhibitors, beta-2 integrin antagonists and adenosine 2a agonists)) or beta adrenergic agents (such as salmeterol, salbutamol, formoterol, fenoterol or terbutaline and salts thereof), antihistamines (eg methapyrilene or loratadine) or antiinfective agents (eg. antibiotics, antivirals).

It will be appreciated that when the compounds of the present invention are administered in combination with other therapeutic agents normally administered by the inhaled or intranasal route, that the resultant pharmaceutical composition may be administered by the inhaled or intranasal route.

Compounds of the invention may conveniently be administered in amounts of, for example, 0.001 to 500 mg/kg body weight, preferably 0.01 to 500 mg/kg body weight, more preferably 0.01 to 100 mg/kg body weight, 1 to 4 times daily. The precise dose will of course depend on the age and condition of the patient and the particular route of administration chosen.

The compounds of the invention have the advantage that they may be more efficacious, show greater selectivity, have fewer side effects, have a longer duration of action, be more bioavailable when administered by the oral route, have more ready and economic synthesis, or have other more desirable properties than similar known compounds.

The invention may be illustrated by reference to the following examples:

EXAMPLES

General Experimental Details

Standard Automated Preparative HPLC Column, Conditions and Eluent

Automated preparative high performance liquid chromatography (autoprep. HPLC) was carried out using a Supelco+5 µm (100 mm×22 mm internal diameter) column eluted with a mixture of solvents consisting of (i) 0.1% trifluoroacetic acid in water and (ii) 0.1% trifluoroacetic acid in acetonitrile, the eluent being expressed as the percentage of (ii) in the solvent mixture, at a flow rate of 4 ml per minute.

Mass Directed Automated Preparative HPLC Column, Conditions and Eluent

Mass directed automated preparative high performance liquid chromatography was carried out using an LCABZ+5 µm (5 cm×10 mm internal diameter) column, employing gradient elution using two solvent systems, (A) 0.1% formic acid in water, and (B) 95% acetonitrile and 0.5% formic acid in water, at a flow rate of 8 ml min$^{-1}$. Mass spectrometry was carried out using a VG Platform Mass Spectrometer, with an HP1100 Diode Array Detector and Accurate Flow Splitter.

LC/MS System

Three alternative Liquid Chromatography Mass Spectroscopy (LC/MS) Systems were used:

System A

This system used an 3 µm ABZ+PLUS (3.3 cm×4.6 mm internal diameter) column, eluting with solvents:A–0.1% v/v formic acid+0.077% w/v ammonium acetate in water; and B–95:5 acetonitrile:water+0.05% v/v formic acid, at a flow rate of 3 ml per minute. The following gradient protocol was used: 100% A for 0.7 mins; A+B mixtures, gradient profile 0–100% B over 3.5 mins; hold at 100% B for 1.1 mins; return to 100% A over 0.2 mins.

System B

This system used an 3 µm ABZ+PLUS (3.3 cm×4.6 mm internal diameter) column, eluting with solvents:A–0.1% v/v formic acid+0.077% w/v ammonium acetate in water; and B–95:5 acetonitrile:water+0.05% v/v formic acid, at a flow rate of 1 ml per minute. The following gradient protocol was used: 100% A for 1.0 min; A+B mixtures, gradient profile 0–100% B over 9.0 mins; hold at 100% B for 3.0 mins; return to 100% A over 2.0 mins.

System C

This system used an 3 µm ABZ+PLUS (3.3 cm×4.6 mm internal diameter) column, eluting with solvents:A–0.1% v/v formic acid+0.077% w/v ammonium acetate in water; and B–95:5 acetonitrile:water+0.05% v/v formic acid, at a flow rate of 1 ml per minute. The following gradient protocol was used: 100% A for 2.0 mins; A+B mixtures, gradient profile 0–100% B over 20 mins; hold at 100% B for 5.0 mins; return to 100% A over 2.0 mins; hold at 100% A for 1.0 mins.

All LC/MS systems used a micromass spectrometer, with electrospray ionisation mode, positive and negative ion switching, mass range 80–1000 a.m.u.

Thermospray Mass Spectra

Thermospray Mass Spectra were determined on a HP 5989A engine mass spectrometer, +ve thermospray, source temperature 250° C., probe temperatures 120° C. (stem), 190° C. (tip), detection mass range 100–850 a.m.u. Compounds were injected in 10 µl of a mixture of solvents comprising 65% methanol and 35% 0.05M aqueous ammonium acetate, at a flow rate of 0.7 ml/min.

Normal Phase Automated Preparative HPLC Column—Conditions

Normal phase automated preparative high performance liquid chromatography (normal phase autoprep HPLC) was carried out using a Nucleosil silica 5 µm (100 mm×20 mm internal diameter) column eluted with an ethyl acetate: heptane two-step gradient (i) 0% to 25% ethyl acetate over 7 min followed by (ii) 25% to 100% ethyl acetate over 5.5 min; at a flow rate of 30 ml/min.

Normal Phase Analytical HPLC Method

Normal phase automated analytical high performance liquid chromatography (normal phase analytical HPLC) was carried out using a Nucleosil silica 3 µm (150 mm×4.6 mm internal diameter) column eluted with an ethyl acetate: heptane two-step gradient (i) 0% to 40% ethyl acetate over 7 min followed by (ii) 40% to 100% ethyl acetate over 2.5 min; at a flow rate of 2 ml/min.

Standard Chiral Analytical HPLC System

This system used a 250×4.6 mm Chiralpak AD 10 µm column, eluting with absolute ethanol:heptane mixtures at a flow rate of 1 ml per minute, with UV detection at 215 nm.

Standard Chiral Preparative HPLC System

This system used a Chiralpak AD column (2 cm×25 cm), eluting with absolute ethanol:heptane mixtures (15 ml/min over 25 mins, UV detection at 215 nm).

Solid Phase Extraction (Ion Exchange)

'SCX' refers to Isolute Flash SCX-2 sulphonic acid solid phase extraction cartridges.

Organic/Aqueous Phase Separation with Hydrophobic Frits

'Hydrophobic frit' refers to a Whatman polypropylene filter tube fitted with a PTFE frit, pore size 5.0 µm.

All temperatures are in ° C.

Intermediate

Intermediate 1: 2,2,2-Trifluoro-N-(morpholin-2-ylmethyl)acetamide

To a stirred solution of morpholin-2-ylmethylamine (3.1 g) in methanol (70 ml) under nitrogen was added an ethereal solution of ethyl-α,α,α-trifluoroacetate (5 ml in 20 ml ether) which had been washed with saturated aqueous sodium bicarbonate, water and brine, and dried. The mixture was stirred for 30 min at 22° C. before removal of all volatiles in vacuo. The residue was dissolved in methanol (10 ml) and the volatiles again removed in vacuo to give the title compound as a white crunchy foam (4.9 g).

Thermospray Mass Spectrum m/z 213 [MH$^+$].

Intermediate 2: N-{[4-(3,4-Dichlorobenzyl)morpholin-2-yl]methyl}-2,2,2-trifluoroacetamide To a stirred solution of Intermediate 1 (3.3 g) in N,N-dimethylformamide (50 ml) under nitrogen was added potassium carbonate (2.46 g) and sodium iodide (2.12 g). A solution of 3,4-dichlorobenzyl chloride (2 ml) in N,N-dimethylformamide (10 ml) was added dropwise to the mixture. The mixture was stirred at 22° C. for 18 h before the volatiles were removed in vacuo. The residue was partitioned between dichloromethane (100 ml) and saturated aqueous sodium carbonate solution (50 ml). The organic phase was subsequently washed with additional saturated aqueous sodium carbonate solution (2×50 ml) and water (50 ml) before drying over magnesium sulphate, filtering and evaporation of the solvent in vacuo to give a pale yellow oil. The oil was purified by Biotage flash chromatography on a 90 g silica cartridge eluting with 25% ethyl acetate in cyclohexane, to give the title compound as a colourless oil (2.97 g).

LC/MS (System A) $R_t$ 2.63 min, Mass Spectrum m/z 371 [MH$^+$].

Intermediate 3: [4-(3,4-Dichlorobenzyl)morpholin-2-yl]methylamine

To a stirred solution of Intermediate 2 (2.97 g) in methanol (15 ml) and water (5 ml) was added potassium carbonate (5.53 g). The mixture was stirred at 22° C. for 18 h before the methanol was removed in vacuo. Water (25 ml) was added and the mixture extracted with ethyl acetate (3×30 ml). The combined organic phases were washed with water (5 ml) and saturated aqueous sodium chloride solution (10 ml) before drying over sodium sulphate, filtering and evaporation of the solvent in vacuo to give a pale yellow oil. The oil was purified by Biotage flash chromatography on a 90 g silica cartridge eluting with 75:8:1 dichloromethane/ethanol/0.880 ammonia solution. The required fractions were combined and the solvent evaporated in vacuo to give the title compound as a colourless oil (1.85 g).

LC/MS (System A) $R_t$ 1.77 min, Mass Spectrum m/z 275 [MH$^+$].

Intermediate 3: [4-(3,4-Dichlorobenzyl)morpholin-2-yl]methylamine (Alternative Synthesis)

A mixture of 2-[(3,4-dichlorobenzyl)amino]ethanol (Chem Abs No. 40172-06-3, 0.980 g) and 2-(oxiran-2-ylmethyl)-1H-isoindole-1,3(2H)-dione (1.10 g) was heated at 80° C. under nitrogen for 3 h. The resulting solid mass was treated with concentrated sulphuric acid (1.5 ml) then stirred at 150° C. for 24 h. The mixture was treated with water (100 ml) then washed with ethyl acetate (2×100 ml). The dark aqueous phase was basified to ~pH 12 using 5M aqueous sodium hydroxide, then extracted with ethyl acetate (2×100 ml). The combined organic extracts were washed with water and brine, dried (Na$_2$SO$_4$) and concentrated under vacuum to give the title compound as a brown oil (1.02 g).

LC-MS (System A): Rt 1.6 min.

Intermediate 3A: [4-(3,4-Dichlorobenzyl)morpholin-2-yl]methylamine Salt with Para-toluenesulphonic Acid 1:1

A solution of 2-[(3,4-dichlorobenzyl)amino]ethanol (2.25 g) and 2-chloroacrylonitrile (1.0 ml) in tetrahydrofuran (3 ml) was heated at 40° C. for 66 h. The solvent was evaporated in vacuo to leave a gum. The residue was redissolved in tetrahydrofuran (20 ml) and cooled to 0–5° C. Potassium tert-butoxide (1.2 g) was added portionwise to this solution over 10 min and the mixture was stirred at 0–5° C. for a further 45 min. The mixture was diluted with water (20 ml) and ethyl acetate (20 ml), the phases were separated and the organic phase was washed with 20% w/w aqueous sodium chloride solution. The organic phase was dried over sodium sulfate and the solvent was evaporated in vacuo to leave a gum (2.75 g).

A portion of this gum (0.22 g) in tetrahydrofuran (1 ml) was treated dropwise with a 1M solution of borane.tetrahydrofuran complex in tetrahydrofuran (2.44 ml) at 15–25° C. The mixture was stirred at 15–25° C. for 16 h, and methanol (3 ml) was added dropwise. The mixture was stirred for a further 5 h and the solvent was evaporated in vacuo. The residue was redissolved in ethyl acetate (4 ml) and p-toluenesulfonic acid monohydrate (0.123 g) was added. The mixture was heated at 50° C. for 20 min, and the suspension was cooled to 15–25° C. and stirred for 15 min. The mixture was filtered, washed with ethyl acetate and dried to give the title compound (0.123 g) as a white solid.

LC/MS (System A) $R_t$ 1.75 min. Mass spectrum m/z 275/277 [MH$^+$]

Intermediate 4: Benzyl 2-{[(trifluoroacetyl)amino]methyl}morpholine-4-carboxylate To a stirred solution of Intermediate 1 (6.37 g) in methanol (250 ml) under nitrogen was added benzylchloroformate (4.7 ml) and triethylamine (6.3 ml). The mixture was stirred at 22° C. for 1 h before the volatiles were removed in vacuo. The residue was purified by Biotage flash chromatography on a 90 g silica cartridge eluting with 33% ethyl acetate in cyclohexane, to give the title compound as a white solid (4.4 g).

LC/MS (System A) $R_t$ 3.22 min, Mass Spectrum m/z 347 [MH$^+$].

Intermediate 5: Benzyl 2-(aminomethyl)morpholine-4-carboxylate

To a stirred solution of Intermediate 4 (4.4 g) in 1:1 methanol/water (300 ml) was added potassium carbonate (17.5 g). The mixture was stirred at 22° C. for 36 h before the volatiles were evaporated in vacuo. The residue was dissolved in water and the solution extracted with dichloromethane (×3). The combined organic extracts were washed with saturated aqueous sodium chloride solution, dried over magnesium sulphate and filtered before evaporation of the solvent in vacuo. The residue was dissolved in methanol and purified by solid phase extraction (Isolute SCX sulphonic acid column), initially washing the cartridge with methanol before eluting with 10% 0.880 ammonia solution in methanol to give the title compound as a colourless oil (2.27 g).

LC/MS (System A) $R_t$ 2.07 min, Mass Spectrum m/z 251 [MH$^+$].

Intermediate 6: Benzyl 2-[({[(4-chlorophenyl)amino]carbonyl}amino)methyl]morpholine-4-carboxylate To a stirred solution of Intermediate 5 (2.0 g) in dichloromethane (100 ml) was added 4-chlorophenylisocyanate (1.35 g). The mixture was stirred at 22° C. for 18 h before 10% 0.880 ammonia solution in methanol (10 ml) was added. Stirring was continued for a further 30 min before the solvent was removed in vacuo. The residue was purified by Biotage flash chromatography on silica gel, eluting with 33% ethyl acetate/cyclohexane; further purification by Biotage flash chromatography on silica gel, eluting with 500:8:1 dichloromethane/ethanol/0.880 ammonia solution gave the impure title compound as a buff solid (3.6 g).

LC/MS (System A) $R_t$ 3.41 min, Mass Spectrum m/z 404 [MH$^+$].

Intermediate 7: N-(Morpholin-2-ylmethyl)-N'-phenylurea

A suspension of 10% palladium on carbon (1.5 g) and Intermediate 6 (3.2 g) in ethyl acetate (250 ml) was stirred vigorously under hydrogen at 1 atmosphere and 22° C. for 20 h. The catalyst was filtered off and the volatiles were removed in vacuo. The procedure was repeated with a further portion of the catalyst (1 g) for a further 24 h before filtration and solvent evaporation in vacuo. Purification of the residue by Biotage flash chromatography on a 90 g silica cartridge, eluting with 100:8:1 dichloromethane/ethanol/

0.880 ammonia solution, gave the title compound as a colourless oil (1.6 g). LC/MS (System A) $R_t$ 1.39 min, Mass Spectrum m/z 236 [MH$^+$].

Intermediate 8: tert-Butyl 2-[({[(4-chlorophenyl)amino]carbonyl}amino)methyl]morpholine-4-carboxylate To a stirred solution of tert-butyl 2-(aminomethyl)morpholine-4-carboxylate (Prepared as described in EP 0 468231, 2.4 g) in dichloromethane (100 ml) was added 4-chlorophenylisocyanate (1.87 g). The mixture was stirred at 22° C. for 16 h before 10% 0.880 ammonia solution in methanol was added. Stirring was continued for a further 30 min before the solvent was removed in vacuo to give the title compound as a white foam (3.98 g).

LC/MS (System A) $R_t$ 3.19 min, Mass Spectrum m/z 370 [MH$^+$].

Intermediate 9: N-(4-Chlorophenyl)-N'-(morpholin-2-ylmethyl)urea

Intermediate 8 (1.9 g) was stirred in 4.0M hydrogen chloride in 1,4-dioxane (40 ml) at 22° C. for 30 min. The solvent was removed in vacuo and the residue was purified by solid phase extraction (Isolute SCX sulphonic acid column), eluting with methanol followed by 10% 0.880 NH$_3$ solution in methanol, to give the title compound as a cream foam (1.15 g). LC/MS (System A) $R_t$ 2.03 min, Mass Spectrum m/z 270 [MH$^+$].

Intermediate 10: 4-Nitrophenyl [4-(3,4-dichlorobenzyl)morpholin-2-yl]methylcarbamate Triethylamine (0.09 ml) was added to solution of Intermediate 3 (0.150 g, 0.545 mmol) in dichloromethane (3 ml) with stirring at 20° C. under nitrogen. The solution was cooled to 0° C. and a solution of 4-nitrophenyl chloroformate (0.121 g) in dichloromethane (1 ml) was added dropwise. The resultant mixture was stirred for 4 h at 0° C. The solution was allowed to warm to 20° C., washed with brine (4 ml), dried (MgSO$_4$), and concentrated in vacuo. Purification by Biotage flash chromatography on silica gel, eluting with 35% ethyl acetate in cyclohexane, gave the title compound as a pale yellow solid (0.119 g). LC/MS (system A) $R_t$ 3.01 min, Mass Spectrum m/z 441 [MH$^+$].

Intermediate 11: 1-[(2S)-4-(3,4-Dichlorobenzyl)morpholin-2-yl]methanamine

Intermediate 3 (racemic mixture, 8 g) was separated into its single enantiomers by preparative chiral-HPLC. The separation was carried out using a 2"×22 cm Chiralpak AD 20 μm column, Merck self pack DAC system, eluting with 95:5:0.1 (v/v) heptane: absolute ethanol: diethylamine (flow rate: 55 ml/min over 40 min, UV detection 225 nm); sample load preparation: 400 mg sample in 20 ml 3:2 (v/v) absolute ethanol: system eluent. The title compound (2.49 g) was obtained as follows: preparative HPLC retention time 23.0 min.

Intermediate 11A: 1-[(2S)-4-(3,4-Dichlorobenzyl)morpholin-2-yl]methanamine Salt with D-tartaric Acid 1:1

35% Hydrazine in water (1.8 ml) was added to a slurry of Intermediate 42 (5 g) in industrial methylated spirits (75 ml), and the mixture was heated to reflux. Chloroform (75 ml) was added and the mixture was heated under reflux for 65 h. The reaction mixture was cooled to 0–4° C. and allowed to stand for 15 min. The by-product phthalhydrazide was removed by vacuum filtration and washed with chloroform (50 ml). The filtrate was washed with water (50 ml, 25 ml), dried (MgSO$_4$), and the solvent evaporated in vacuo to give an oil. This was dissolved in methanol (20 ml), which was evaporated in vacuo to give an oil. The oil was dissolved in methanol (100 ml) and D-tartaric acid (1.05 g) was added. The mixture was heated to and maintained at reflux for 30 min. The solution was cooled to 45–50° C., then seeded. The slurry was held at this temperature for 30 min, then cooled to 0–4° C. and allowed to stand for 30 min. The product was isolated by filtration to give the title compound as a white solid (2.59 g).

A sample of the crude D-tartrate salt (500 mg) was dissolved in water (1.4 ml). Methanol (23 ml) was added to give a slurry which was heated to reflux to give a solution. The mixture was stirred at reflux for 30 min, then cooled slowly, seeding at 55° C. The resultant slurry was cooled to 0–4° C. and allowed to stand 30 min. The product was isolated by filtration to give the title compound as a white solid (0.355 g).

ee: 91.6% ee

LC/MS (System A) $R_t$ 1.75 min. Mass spectrum m/z 275/277 [MH$^+$]

Chiral analytical HPLC (Chiralpak AD column, 4.6×250 mm, eluent 50:50:0.1 MeOH:EtOH:Butylamine, flow rate 0.5 ml/min, UV detection at 220 nm), Rt 8.9 min.

Intermediate 11A (Alternative Procedure): 1-[(2S)-4-(3,4-Dichlorobenzyl)morpholin-2-yl]methanamine Salt with D-tartaric Acid 1:1

Intermediate 3 (0.613 g) was dissolved in methanol (12.3 ml). D-Tartaric acid (0.335 g) was added and the slurry was heated to reflux for 50 min. The mixture was allowed to cool to 0–5° C. and the precipitate isolated by filtration to give the title compound as a white solid (0.4 g).

ee: 76% ee

Chiral analytical HPLC (Chiralpak AD column, 4.6×250 mm, eluent 50:50:0.1 MeOH:EtOH:Butylamine, flow rate 0.5 ml/min, UV detection at 220 nm), Rt 8.9 min.

Intermediate 12: 1-[(2R)-4-(3,4-Dichlorobenzyl)morpholin-2-yl]methanamine

Intermediate 12 was prepared in an analogous manner to Intermediate 11 yielding the title compound (2.24 g) as follows: preparative HPLC retention time 27.8 min.

Intermediate 12A: 1-[(2R)$_4$-(3,4-Dichlorobenzyl)morpholin-2-yl]methanamine Salt with L-tartaric Acid 1:1

Intermediate 3 (0.500 g) was dissolved in methanol (5 ml). L-Tartaric acid (0.273 g) was added and the mixture was heated to ~65° C. to give a milky slurry, and maintained at this temperature for 1 h. Further methanol (5 ml) was added and the mixture left to cool slowly to 15–25° C., then cooled further to 0–4° C. The mixture was stirred for 30 min at this temperature and the product isolated by filtration to give the title compound as a white solid (0.38 g).

ee: 78%

LC/MS (System A) $R_t$ 1.75 min. Mass spectrum m/z 275/277 [MH$^+$]

Chiral analytical HPLC (Chiralpak AD column, 4.6×250 mm, eluent 50:50:0.1 MeOH:EtOH:Butylamine, flow rate 0.5 ml/min, UV detection at 220 nm), Rt 10.5 min.

Intermediate 13: 4-Nitrophenyl [(2S)-4-(3,4-dichlorobenzyl)morpholin-2-yl]methylcarbamate Intermediate 13 was prepared in an analogous manner to Intermediate 10 from Intermediate 11 (0.225 g) and 4-nitrophenylchloroformate (0.182 g) to yield the title compound (0.2 g).

LC-MS (System A) Rt 3.1 mins. Mass Spectrum m/z 441 [MH$^+$].

Intermediate 14: 4-Nitrophenyl [(2R)-4-(3,4-dichlorobenzyl)morpholin-2-yl]methylcarbamate Intermediate 14 was prepared in an analogous manner to Intermediate 10 from Intermediate 12 (0.21 g) and 4-nitrophenylchloroformate (0.17 g) to yield the title compound (0.23 g).

LC-MS (System A) Rt 3.09 mins. Mass Spectrum m/z 441 [MH$^+$].

Intermediate 15: tert-Butyl 4-{[({[4-(3,4-dichlorobenzyl)morpholin-2-yl]methyl}amino)carbonyl]amino}piperidine-1-carboxylate Intermediate 15 was prepared in an analogous manner to Example 43, using tetrahydrofuran as solvent, without base, to give the title compound as a white solid (0.157 g).

LC/MS (System A) Rt 2.92 min, Mass spectrum m/z 501 [MH$^+$].

Intermediate 16: N-{[4-(3,4-Dichlorobenzyl)morpholin-2-yl]methyl}-N'-piperidin-4-ylurea Hydrochloride Intermediate 15 (0.157 g) was stirred in dioxane (4 ml) containing 4.0M hydrogen chloride in dioxane (0.78 ml) for 16 h, at 23° C. under nitrogen. The solvent was removed in vacuo, azeotroped with dichloromethane (20 ml), triturated in ether and dried under vacuum to give the title compound as a pale yellow solid (0.12 g).

LC/MS (System A) Rt 2.02 min, Mass spectrum m/z 401 [MH$^+$].

Intermediate 17: tert-butyl 4-({[({[(2S)-4-(3,4-dichlorobenzyl)morpholin-2-yl]methyl}amino)carbonyl]amino}methyl)piperidine-1-carboxylate Intermediate 17 was made in an analogous manner to that of Example 57.

LC-MS (System A) Rt 2.72 mins Mass Spectrum m/z 515 [MH$^+$].

Intermediate 18: N-{[(2S)-4-(3,4-dichlorobenzyl)morpholin-2-yl]methyl}-N'-(piperidin-4-ylmethyl)urea Dihydrochloride Intermediate 17 (0.390 g) was stirred in 4.0M hydrogen chloride in dioxane (4 ml) for 2 h, at 23° C. under nitrogen. The solvent was removed in vacuo, azeotroped with dichloromethane (20 ml), and dried under vacuum to give the title compound as a pale yellow solid, (0.33 g).

LC/MS (System A) Rt 1.84 min, Mass spectrum m/z 415 [MH$^+$].

Intermediate 19: [(2S)-4-(3-chlorobenzyl)morpholin-2-yl]methylamine

Intermediate 19 was made in an analogous manner to that of Intermediate 11.

Preparative HPLC retention time 26.1 min

Intermediate 20: [(2S)-4-(2,3-dichlorobenzyl)morpholin-2-yl]methylamine

Intermediate 20 was made in an analogous manner to that of Intermediate 11.

Preparative HPLC retention time 25.3 min

Intermediate 21: [(2S)-4-(3,4-difluorobenzyl)morpholin-2-yl]methylamine

Intermediate 21 was made in an analogous manner to that of Intermediate 11.

Preparative HPLC retention time 28.3 min

Intermediate 22: 4-Nitrophenyl prop-2-ynylcarbamate

Propargylamine (0.017 ml) and triethylamine (0.38 ml) in dichloromethane (2 ml) were added dropwise to p-nitrophenylchloroformate (0.55 g) in dichloromethane (3 ml) at 0° C. The solution was stirred for 1 h at this temperature then at 23° C. for 5 h. The solvent was removed in vacuo and the residue purified by solid phase extraction (10 g silica gel cartridge, Varian Bond Elut), eluting with 20–60% ethyl acetate in cyclohexane, to give the title compound as a white solid (0.419 g).

LC/MS (system A) Rt 2.67 min Mass spectrum m/z 220 [MH$^+$].

Intermediate 23: {(2S)-4-[(5-chlorothien-2-yl)methyl]morpholin-2-yl}methylamine

Intermediate 23 was made in an analogous manner to that of Intermediate 11.

Chiral preparative HPLC retention time 25.2 min

Intermediate 24: [(2R,5R)-4-(3,4-dichlorobenzyl)-5-methylmorpholin-2-yl]methylamine (Mixture with Trans Isomer, cis:trans 60:40)

Intermediate 24 was made in an analogous manner to that of Intermediate 31 from (2R)-2-aminopropan-1-ol.

LC-MS (System A): Rt 1.9 mins Mass Spectrum m/z 289 [MH$^+$].

Intermediate 25: tert-Butyl 4-{[({[(2S)-4-(3,4-dichlorobenzyl)morpholin-2-yl]methyl}amino)carbonyl]amino}butanoate 4-Aminobutyric acid tert-butyl ester hydrochloride (0.235 g) was added to a stirred solution of Intermediate 13 (0.440 g) and N,N-diisopropylethylamine (0.42 ml) in dry dichloromethane (20 ml) under nitrogen, and the mixture was stirred at 22° C. for 18 h. The mixture was treated with saturated aqueous potassium carbonate (20 ml) and stirred for 5 min. The layers were separated and the organic layer applied to a silica gel cartridge (10 g Varian Bond Elut). Elution with dichloromethane, ether, ethyl acetate, and acetone gave the crude product (0.357 g). Further purification by chromatography on silica gel (10 g Varian Bond Elut cartridge), eluting with dichloromethane (1 column volume), ether (4 column volumes) and ethyl acetate (8 column volumes) gave the title compound as a gum (0.345 g).

LC-MS (System A) Rt 2.66 min Mass Spectrum m/z 460 [MH$^+$].

Intermediate 26: 4-{[({[(2S)-4-(3,4-Dichlorobenzyl)morpholin-2-yl]methyl}amino)carbonyl]amino}butanoic Acid Hydrochloride Intermediate 25 (0.345 g) was dissolved in 4M hydrogen chloride in dioxane (5 ml), and the mixture was allowed to stand at 22° C. for 19.5 h. The solvent was evaporated in vacuo to give the title compound as a white solid (0.330 g).

LC-MS (System A) Rt 2.16 min Mass Spectrum m/z 404 [MH$^+$].

Intermediate 27: 2-[3-(pyrrolidin-1-ylsulfonyl)propyl]-1H-isoindole-1,3(2H)-dione A solution of 3-(1,3-dioxo-1,3-dihydro-2H-isoindol-2-yl)propane-1-sulfonyl chloride (0.288 g) in dry tetrahydrofuran (5 ml) was treated with N,N-diisopropylethylamine (0.350 ml) and pyrrolidine (0.10 ml) at 22° C. under nitrogen, and the mixture was stirred at 22° C. for 1 h. After standing overnight at room temperature, the mixture was partitioned between saturated aqueous sodium bicarbonate (10 ml) and ethyl acetate (2×10 ml). The organic layers were washed with brine, dried (MgSO$_4$) and evaporated in vacuo to give a white solid (0.145 g).

LC-MS (System A) Rt 2.81 min. Mass Spectrum m/z 323 [MH$^+$].

Intermediate 28: 3-(Pyrrolidin-1-ylsulfonyl)propylamine

A solution of Intermediate 27 (0.139 g) in isopropanol (7.6 ml) and water (1.3 ml) was treated with sodium borohydride (0.081 g), and the mixture was stirred at room temperature under nitrogen for 19 h. Glacial acetic acid (0.45 ml) was added cautiously and the mixture heated at 80° C. for 2 h. The solvents were evaporated in vacuo to give a white solid, which was dissolved in methanol and applied to a sulphonic acid ion exchange cartridge (10 g Isolute SCX). Elution with methanol followed by 10% 0.880 ammonia in methanol, and evaporation of the ammonia/methanol fraction gave the title compound as a white solid (0.027 g).

TLC $SiO_2$ (dichloromethane:ethanol:0.880 ammonia 89:10:1) Rf 0.2

Intermediate 29: 4-Nitrophenyl [(2S)-4-(3,4-dichlorobenzyl)morpholin-2-yl]methylcarbamate Hydrochloride A mixture of triethylamine (0.101 ml) and Intermediate 11 (2.0 g) in dichloromethane (20 ml) was added dropwise to a solution of 4-nitrophenyl chloroformate (1.62 g) in dichloromethane (10 ml) with stirring at 0° C. under nitrogen. The solution was stirred for 3 h at 0° C., allowed to warm to 20° C., and stand for 18 h. The volatile components were evaporated in vacuo, and the residue was purified by Biotage flash chromatography on silica gel (90 g cartridge), eluting initially with 10% methanol in dichloromethane and subsequently with 20% methanol in dichloromethane, to give the title compound as a light brown solid (2.5 g).

LCMS (System A) $R_t$ 2.89 min Mass Spectrum m/z 441 [MH$^+$]

Intermediate 30: 1-(2-Methyl-2H-tetraazol-5-yl)methanamine Hydrochloride

To Intermediate 37 (0.47 g) was added 4.0M hydrogen chloride in 1,4-dioxane (5 ml). The mixture was stirred at 22° C. for 3 h, and the solvent removed in vacuo. The residue was again dissolved in 4.0M hydrogen chloride in 1,4-dioxane (5 ml), and left to stand at 22° C. for 18 h. Evaporation of the solvent in vacuo gave the title compound as a cream solid (0.319 g).

Thermospray Mass Spectrum m/z=114 [MH$^+$]

Intermediate 31: 1-[4-(3,4-Dichlorobenzyl)-5-methylmorpholin-2-yl]methanamine (Cis/Trans Ratio 2:1)

A mixture of Intermediate 43 (0.470 g) and 2-(oxiran-2-ylmethyl)-1H-isoindole-1,3(2H)-dione (0.410 g) was heated at 80° C. under nitrogen for 5 h. The mixture was treated with concentrated sulphuric acid (0.6 ml) then stirred at 150° C. for 42 h. The mixture was treated with water (50 ml) then washed with ethyl acetate (2×50 ml). The dark aqueous phase was basified to ~pH 11 using 5M aqueous sodium hydroxide then extracted with ethyl acetate (2×50 ml). The combined organic extracts were washed with water and brine, dried ($Na_2SO_4$) and concentrated under vacuum to give the title compound as a brown oil (0.42 g).

LC-MS (System A): Rt 1.74 min.

Intermediate 32: tert-Butyl {(2S)-4-[1-(3,4-dichlorophenyl)ethyl]morpholin-2-yl}methylcarbamate tert-Butyl (2R)-morpholin-2-ylmethylcarbamate (2.00 g) in N,N-dimethylformamide (16 ml) was treated with N,N-diisopropylethylamine (1.6 ml) followed by 4-(1-bromoethyl)-1,2-dichlorobenzene (2.58 g). After stirring for five days at room temperature, further portions of 4-(1-bromoethyl)-1,2-dichlorobenzene (2.58 g) and N,N-diisopropylethylamine (1.6 ml) were added and stirring continued for 24 h at room temperature. The solution was treated with dichloromethane (70 ml) and saturated aqueous sodium hydrogen carbonate (30 ml) and the mixture shaken vigorously. The organic phase was separated and applied equally onto sulphonic acid ion exchange cartridges (5×10 g Isolute SCX, pre-treated with methanol). The cartridges were each eluted with methanol (one column volume) followed by 10% 0.880 ammonia in methanol (one column volume); evaporation in vacuo of the combined basic fractions gave the title compound as a clear colourless gum (3.22 g)

LC-MS (System A) Rt 2.74 min, Mass Spectrum m/z 389 [MH$^+$].

Intermediate 33: 1-{(2S)-4-[1-(3,4-Dichlorophenyl)ethyl]morpholin-2-yl}methanamine Dihydrochloride Intermediate 32 was treated with 4M hydrogen chloride in dioxane (15 ml) and the solution stirred for 2 h at room temperature. The solution was treated with methanol (20 ml) and concentrated in vacuo to give the title compound as an off-white solid (1.53 g).

LC/MS (System A) Rt 1.86 min and 1.91 min, Mass spectrum m/z 289 [MH$^+$].

Intermediates 34 and 35: 4-Nitrophenyl {(2S)-4-[1-(3,4-dichlorophenyl)ethyl]morpholin-2-yl}methylcarbamate (Isomer I and II, Respectively)

Intermediate 33 (0.724 g) in dichloromethane (5 ml) was treated with triethylamine (1.14 ml), forming a slurry which was added portion-wise over 5 min to a solution of 4-nitrophenyl chloroformate (0.444 g) in anhydrous dichloromethane (5 ml) at 0° C. under nitrogen. The stirring solution was allowed to warm to room temperature over 2 h, then filtered; the filtrate was purified directly by chromatography on silica gel (Biotage 90 g column), eluting with 35–40% ethyl acetate in cyclohexane, and appropriate fractions evaporated in vacuo to give the title compound (Isomer I) as an opaque yellow film (0.202 g).

LC/MS (System A) Rt 2.90 min, Mass spectrum m/z 454 [MH$^+$].

Analytical Chiral HPLC $R_t$ 18.03 mins (eluent 25% EtOH/heptane).

Appropriate other fractions were combined and concentrated in vacuo to give the other title compound (Isomer II) (0.196 g) as an opaque yellow film.

LC/MS (System A) $R_t$ 2.88 min, Mass spectrum m/z 454 [MH$^+$].

Analytical Chiral HPLC $R_t$ 15.38 mins (eluent 25% EtOH/heptane).

Intermediate 36: tert-Butyl 1H-tetraazol-5-ylmethylcarbamate

To a stirred solution of 1-(1H-tetraazol-5-yl)methanamine (6.0 g) in water (120 ml) at 22° C. was added sodium hydroxide (4.8 g), followed by dropwise addition of a solution of di-tert-butyldicarbonate (13.48 g) in methanol (20 ml). Further methanol (40 ml) was added to the mixture and stirring continued for 4 h; the mixture was then allowed to stand for 60 h at 4° C. The methanol was evaporated in vacuo and the aqueous residue acidified to approximately pH 6 with 2M aqueous hydrochloric acid. The aqueous mixture was extracted with ethyl acetate (×3) and the combined organic extracts were washed with saturated aqueous sodium chloride, dried ($MgSO_4$) and the solvent evaporated in vacuo to give the title compound as a white solid (1.50 g).

Thermospray Mass Spectrum m/z 200 [MH$^+$], 217 [MNH$_4^+$]

Intermediate 37: tert-Butyl (2-methyl-2H-tetraazol-5-yl)methylcarbamate

To a stirred solution of Intermediate 36 (1.0 g) in dichloromethane (35 ml) and methanol (10 ml) at 22° C. under nitrogen was added dropwise 10% trimethylsilyldiazomethane in hexane (12.0 ml). The mixture was stirred for 2 h at 22° C. before acetic acid (2 ml) was added dropwise and the solvents were evaporated in vacuo. The crude residue was purified by Biotage flash column chromatography on silica gel (90 g cartridge), eluting with 10% cyclohexane in ether. The fractions for the first eluting isomer were combined and the solvents evaporated in vacuo to give the title compound as pale yellow crystals (0.487 g).

Thermospray Mass Spectrum m/z=214 [MH$^+$]

TLC (SiO$_2$), 10% cyclohexane/ether) R$_f$=0.35, visualised with KMnO$_4$

Intermediate 38: tert-Butyl 3-(ethylthio)propylcarbamate

A solution of tert-butyl 3-bromopropylcarbamate (0.30 g) in N,N-dimethylformamide (5 ml) was treated with ethanethiol (0.104 ml) and potassium carbonate (0.29 g), and the mixture stirred at room temperature overnight. The mixture was partitioned between water (20 ml) and dichloromethane (30 ml), and the organic layers evaporated in vacuo to give the title compound (0.236 g).

TLC SiO$_2$ (cyclohexane:ethyl acetate 4:1) Rf 0.5.

Intermediate 39: tert-Butyl 3-(ethylsulfonyl)propylcarbamate

3-Chloroperoxybenzoic acid (0.373 g) was added to a stirred solution of Intermediate 38 (0.236 g) in dry dichloromethane (6 ml) at 22° C. under nitrogen, and the mixture was stirred at 22° C. for 18 h. The mixture was treated with saturated aqueous sodium carbonate (10 ml), stirred for 3 min, and the separated organic layer evaporated in vacuo to give the title compound (0.275 g).

NMR (CDCl$_3$) 5.15δ(1H, br.t, NH), 3.25δ(2H, q, CH$_2$), 3.00δ(4H, t+q, 2×CH$_2$), 2.03δ(2H, m, CH$_2$), 1.50–1.30δ (12H, s+t, 4×CH$_3$)

Intermediate 40: 3-(Ethylsulfonyl)propan-1-amine Hydrochloride

Intermediate 39 (0.275 g) was dissolved in 4M hydrogen chloride in dioxane (3 ml), and the solution was allowed to stand at 22° C. for 2 h. The solvent was evaporated in vacuo to give the title compound as a white solid (186 mg).

NMR (D4 MeOH) 3.25δ(2H, t, CH$_2$), 3.15δ(4H, t+q, 2×CH$_2$), 2.18δ(2H, m, CH$_2$), 1.38δ(3H, t, CH$_3$).

Intermediate 41: [4-(3,4-Dichlorobenzyl)-1,4-oxazepan-2-yl]methylamine

Formyl polystyrene resin (1.6 g, loading=2.95 mmol/g) was washed five times with tetrahydrofuran in a glass sintered peptide vessel. A solution of 1-(1,4-oxazepan-2-yl)methanamine (0.619 g) in tetrahydrofuran (20 ml) was added and the mixture shaken at 22° C. for 18 h. The mixture was filtered and the resin washed with tetrahydrofuran (4×20 ml) and methanol (3×10 ml) and dried. A portion of the dried resin (1.2 g) was suspended in N,N-dimethylformamide (20 ml), N,N-diisopropylethylamine (2.04 ml) and 3,4-dichlorobenzylchloride were added. The mixture was stirred gently at 70° C. for 22 h. After cooling, the mixture was filtered and the resin washed with THF (5×10 ml) and dichloromethane (5×10 ml) and air-dried on the sinter. The resin was placed into a glass sintered peptide vessel and suspended in tetrahydrofuran (9 ml); conc. hydrochloric acid (3 ml) was added, and the vessel was shaken for 2 h. The resin was filtered off and washed with tetrahydrofuran (2×10 ml).

The combined filtrates were concentrated in vacuo to give a clear oil, which was applied to an ion exchange cartridge (10 g Isolute SCX, pre-conditioned with methanol). Elution with methanol (3 column volumes) followed 10% 0.880 ammonia in methanol (2 column volumes) and evaporation of the basic fractions in vacuo gave a residue. The ion exchange purification was repeated (as above) to give the title compound as a colourless gum (0.256 g).

$^1$H NMR (CDCl$_3$): 7.46δ(1H, d, Aromatic CH), 7.38δ(1H, d, Aromatic CH), 7.19δ(1H, dd, Aromatic CH), 3.94δ(1H, m, CH), 3.80δ(1H, m, CH), 3.59δ(2H, s, CH$_2$), 3.57δ(1H, m, CH), 2.82–2.53δ(5H, m, 5×CH), 2.38δ(1H, dd, CH), 1.98–1.78δ(2H, m, 2×CH), 1.49δ(2H+H$_2$O, br.s, NH$_2$).

Intermediate 42: 2-{[4-(3,4-dichlorobenzyl)morpholin-2-yl]methyl}-1H-isoindole-1,3(2H)-dione To a solution of 2-(oxiran-2-ylmethyl)-1H-isoindole-1,3 (2H)-dione (N-(2,3-epoxypropyl)phthalimide) (2 g) in tetrahydrofuran (4 ml) was added 2-[(3,4-dichlorobenzyl) amino]ethanol (2.16 g) with stirring, under a nitrogen atmosphere. The mixture was heated to 66° C. for 22 h, then cooled to 0° C. A further portion of tetrahydrofuran (10 ml) was added, followed by triphenylphosphine (2.88 g). Diisopropyl azodicarboxylate (2.2 g) was then added over 10 min. The mixture was stirred at 0° C. for a further 30 min, and at room temperature for 14 h. To the crude solution was added ethyl acetate (100 ml), then 2M aqueous hydrochloric acid (250 ml). The resulting white precipitate was isolated by filtration, and dried in vacuo to give the title compound as its white crystalline hydrochoride salt (2.01 g). This was partitioned between 8% aqueous sodium bicarbonate (200 ml) and ethyl acetate (50 ml). The organic phase was separated, dried over magnesium sulfate and the solvent evaporated in vacuo to give a solid. Dichloromethane (20 ml) was added to the residue and the solvent again evaporated in vacuo to give the title compound as a white solid (1.1 g).

LC/MS R$_f$ 2.91 min. Mass Spectrum m/z 405 [MH$^+$]

Intermediate 43: 2-[(3,4 Dichlorobenzyl)amino]propan-1-ol 3,4-Dichlorobenzyl chloride (0.988 g) was added to 2-amino-1-propanol (4.10 g) and the mixture was stirred at 50° C. under nitrogen for 2 h. The mixture was partitioned between saturated aqueous sodium bicarbonate (100 ml) and ethyl acetate (100 ml) and the phases were separated. The organic layer was washed with water (4×100 ml) and brine, dried (Na$_2$SO$_4$) then concentrated under vacuum to give the title compound as a white solid (0.935 g).

LC-MS (System A): Rt 2.13 min.

EXAMPLES

Example 1

N-Benzyl-N'-{[4-(3,4-dichlorobenzyl)morpholin-2-yl]methyl}urea

To a stirred solution of Intermediate 3 (0.025 g) in dichloromethane (1 ml) was added benzylisocyanate (16.8 pt). The mixture was stirred at 22° C. for 18 h before tris-(2-aminoethyl)amine polystyrene (Argonaut Technologies, 0.04 g @ 3.85 mmol/g) was added. Stirring was continued for a further 72 h before the mixture was poured onto a 1 g solid phase extraction (Isolute SCX sulphonic acid) cartridge. The cartridge was washed with methanol before eluting with 10% 0.880 ammonia solution in methanol. The basic fraction was evaporated in vacuo to give a pale yellow solid. The solid was purified by eluting through a 1 g silica solid phase extraction cartridge (Varian Bondelut) eluting sequentially with dichloromethane, ether, ethyl acetate, acetone, acetonitrile and methanol, to give the title compound as a white solid (0.031 g). LC/MS (System A) $R_t$ 2.22 min, Mass Spectrum m/z 408 [MH$^+$].

Example 2

N-{[4-(3,4-Dichlorobenzyl)morpholin-2-yl]methyl}-N'-(4-methoxybenzyl)urea

Example 2 was prepared in an analogous manner to Example 1 using a mixture of Intermediate 3 (0.025 g) and 1-(isocyanatomethyl)-4-methoxybenzene (19.5 μl) to give the title compound (0.0257 g). LC-MS (System A): Rt 2.23 mins, Mass Spectrum m/z 438 [MH$^+$].

Example 3

N-{[4-(3,4-Dichlorobenzyl)morpholin-2-yl]methyl}-N'-(4-methylbenzyl)urea

Example 3 was prepared in an analogous manner to Example 1 using a mixture of Intermediate 3 (0.025 g) and 1-(isocyanatomethyl)-4-methylbenzene (19.1 μl) to give the title compound (0.0318 g). LC-MS (System A): Rt 2.33 mins, Mass Spectrum m/z 422 [MH$^+$].

Example 4

N-{[4-(3,4-Dichlorobenzyl)morpholin-2-yl]methyl}-N'-(3-methylbenzyl)urea

Example 4 was prepared in an analogous manner to Example 1 using a mixture of Intermediate 3 (0.025 g) and 1-(isocyanatomethyl)-3-methylbenzene (19.1 μl) to give the title compound (0.0382 g). LC-MS (System A): Rt 2.32 mins, Mass Spectrum m/z 422 [MH$^+$].

Example 5

N-(3-Cyanophenyl)-N'-{[4-(3,4-dichlorobenzyl)morpholin-2-yl]methyl}urea

Example 5 was prepared in an analogous manner to Example 1 using a mixture of Intermediate 3 (0.025 g) and 3-isocyanatobenzonitrile (0.0196 g) to give the title compound (0.0257 g). LC-MS (System A): Rt 2.29 mins, Mass Spectrum m/z 419 [MH$^+$].

Example 6

N-{[4-(3,4-Dichlorobenzyl)morpholin-2-yl]methyl}-N'-(2-methylbenzyl)urea

Example 6 was prepared in an analogous manner to Example 1 using a mixture of Intermediate 3 (0.025 g) and 1-(isocyanatomethyl)-2-methylbenzene (0.0201 g) to give the title compound (0.0269 g). LC-MS (System A): Rt 2.31 mins, Mass Spectrum m/z 422 [MH$^+$].

Example 7

N-Cyclohexyl-N'-{[4-(3,4-dichlorobenzyl)morpholin-2-yl]methyl}urea

Example 7 was prepared in an analogous manner to Example 1 using a mixture of Intermediate 3 (0.025 g) and isocyanatocyclohexane (17.4 μl) to give the title compound (0.0298 g). LC-MS (System A): Rt 2.26 mins, Mass Spectrum m/z 400 [MH$^+$].

Example 8

N-{[4-(3,4-Dichlorobenzyl)morpholin-2-yl]methyl}-N'-(2-phenylethyl)urea

Example 8 was prepared in an analogous manner to Example 1 using a mixture of Intermediate 3 (0.025 g) and (2-isocyanatoethyl)benzene (18.9 μl) to give the title compound (0.0312 g). LC-MS (System A): Rt 2.29 mins, Mass Spectrum m/z 422 [MH$^+$].

Example 9

N-({4-[2-(2,3-Dihydro-1H-indol-1-yl)-2-oxoethyl]morpholin-2-yl}methyl)-N'-phenylurea To a stirred solution of Intermediate 7 (0.01 g) in N,N-dimethylformamide (0.5 ml) was added 1-(2-chloroacetyl)indoline (0.0092 g). The mixture was stirred at 22° C. for 17 h before tris-(2-aminoethyl)amine polystyrene (Argonaut Technologies, 0.01 g @ 4.46 mmol/g) and polystyrene methyl isocyanate (Argonaut Technologies, 0.033 g @ 1.39 mmol/g) was added. Stirring was continued for a further 30 min before the mixture was purified by solid phase extraction (1 g Isolute SCX sulphonic acid column), eluting with methanol followed by 10% 0.880 ammonia solution in methanol. The basic fraction was evaporated in vacuo to give the title compound as a white solid (0.012 g). LC/MS (System A) $R_t$ 2.69 min, Mass Spectrum m/z 394 [MH$^+$].

Example 10

N-Allyl-N'-{[4-(3,4-dichlorobenzyl)morpholin-2-yl]methyl}urea

Example 10 was prepared in an analogous manner to Example 1 using a mixture of Intermediate 3 (0.025 g) and 3-isocyanatoprop-1-ene (12.0 μl) to give the title compound (0.027 g). LC-MS (System A): Rt 1.93 mins, Mass Spectrum m/z 358 [MH$^+$].

Example 11

N-{[4-(3,4-Dichlorobenzyl)morpholin-2-yl]methyl}-N-(3-fluorophenyl)urea

Example 11 was prepared in an analogous manner to Example 1 using a mixture of Intermediate 3 (0.025 g) and 1-fluoro-3-isocyanatobenzene (15.6 μl) to give the title compound (0.019 g). LC-MS (System A): Rt 2.35 mins, Mass Spectrum m/z 412 [MH$^+$].

Example 12

N-(3-Bromophenyl)-N'-{[4-(3,4-dichlorobenzyl) morpholin-2-yl]methyl}urea

Example 12 was prepared in an analogous manner to Example 1 using a mixture of Intermediate 3 (0.025 g) and 1-bromo-3-isocyanatobenzene (17.0 µl) to give the title compound (0.03 g). LC-MS (System A): Rt 2.50 mins, Mass Spectrum m/z 472 [MH$^+$].

Example 13

N-(3-Chlorophenyl)-N'-{[4-(3,4-dichlorobenzyl) morpholin-2-yl]methyl}urea

Example 13 was prepared in an analogous manner to Example 1 using a mixture of Intermediate 3 (0.025 g) and 1-chloro-3-isocyanatobenzene (16.6 µl) to give the title compound (0.0247 g). LC-MS (System A): Rt 2.46 mins, Mass Spectrum m/z 428 [MH$^+$].

Example 14

N-(4-Chlorophenyl)-N'-{[4-(3,4-dichlorobenzyl) morpholin-2-yl]methyl}urea

Example 14 was prepared in an analogous manner to Example 1 using a mixture of Intermediate 3 (0.025 g) and 1-chloro-4-isocyanatobenzene (17.4 µl) to give the title compound (0.0275 g). LC-MS (System A): Rt 2.45 mins, Mass Spectrum m/z 428 [MH$^+$].

Example 15

Methyl 3-{[({[4-(3,4-dichlorobenzyl)morpholin-2-yl]methyl}amino)carbonyl]amino}benzoate Example 15 was prepared in an analogous manner to Example 1 using a mixture of Intermediate 3 (0.025 g) and methyl 3-isocyanatobenzoate (0.0241 g) to give the title compound (0.037 g). LC-MS (System A): Rt 2.32 mins, Mass Spectrum m/z 452 [MH$^+$].

Example 16

N-{[4-(3,4-Dichlorobenzyl)morpholin-2-yl]methyl}-N'-[4-(difluoromethoxy)phenyl]urea Example 16 was prepared in an analogous manner to Example 1 using a mixture of Intermediate 3 (0.025 g) and 1-(difluoromethoxy)-4-isocyanatobenzene (19.1 µl) to give the title compound (0.0252 g). LC-MS (System A): Rt 2.41 mins, Mass Spectrum m/z 460 [MH$^+$].

Example 17

N-{[4-(3,4-Dichlorobenzyl)morpholin-2-yl]methyl)-N'-(4-fluorophenyl)urea

Example 17 was prepared in an analogous manner to Example 1 using a mixture of Intermediate 3 (0.025 g) and 1-fluoro-4-isocyanatobenzene (15.5 µl) to give the title compound (0.031 µg). LC-MS (System A): Rt 2.30 mins, Mass Spectrum m/z 421 [MH$^+$].

Example 18

N-{[4-(3,4-Dichlorobenzyl)morpholin-2-yl]methyl}-N'-[3-(methylthio)phenyl]urea

Example 18 was prepared in an analogous manner to Example 1 using a mixture of Intermediate 3 (0.025 g) and 1-isocyanato-3-(methylthio)benzene (18.8 µl) to give the title compound (0.0352 g). LC-MS (System A): Rt 2.41 mins, Mass Spectrum m/z 440 [MH$^+$].

Example 19

N-(4-Chlorophenyl)-N'-{[4-(1 naphthylmethyl)morpholin-2-yl]methyl}urea

To a stirred solution of Intermediate 9 (0.01 g) in N,N-dimethylformamide (1 ml) was added 1-(chloromethyl) naphthalene (6.1 µl). The mixture was stirred at 22° C. for 24 h before tris-(2-aminoethyl)amine polystyrene (Argonaut Technologies, 0.01 g @ 4.46 mmol/g) and polystyrene methyl isocyanate (Argonaut Technologies, 0.033 g @ 1.39 mmol/g) was added. Stirring was continued for a further 2 h before the mixture was purified by solid phase extraction (Isolute SCX sulphonic acid column), eluting with methanol followed by 10% 0.880 ammonia solution in methanol. The basic fraction was evaporated in vacuo to give the title compound (0.003 g). LC/MS (System A) R$_t$ 2.82 min, Mass Spectrum m/z 4140 [MH$^+$].

Example 20

N-(4-Bromophenyl)-N'-{[4-(3,4-dichlorobenzyl) morpholin-2-yl]methyl}urea

Example 20 was prepared in an analogous manner to Example 1 using a mixture of Intermediate 3 (0.025 g) and 1-bromo-4-isocyanatobenzene (0.027 g) to give the title compound (0.033 g). LC-MS (System A): Rt 2.49 mins, Mass Spectrum m/z 472 [MH$^+$].

Example 21

N-(4-Chlorophenyl)-N'-[4-(3-iodobenzyl)morpholin-2-yl]methyl}urea

Example 21 was prepared in an analogous manner to Example 19 using a mixture of Intermediate 9 (0.01 g) and 1-(bromomethyl)-3-iodobenzene (0.0121 g) to give the title compound (0.0087 g). LC-MS (System A): Rt 2.83 mins, Mass Spectrum m/z 486 [MH$^+$].

Example 22

N-{[4-(3,4-Dichlorobenzyl)morpholin-2-yl]methyl}-N'-[3-(trifluoromethyl)phenyl]urea Example 22 was prepared in an analogous manner to Example 1 using a mixture of Intermediate 3 (0.025 g) and 1-isocyanato-3-(trifluoromethyl)benzene (18.8 µl) to give the title compound (0.0112 g). LC-MS (System A): Rt 2.56 mins, Mass Spectrum m/z 462 [MH$^+$].

Example 23

N-(4-Chlorophenyl)-N'-{[4-(2-naphthylmethyl)Morpholin-2-yl]methyl}urea

Example 23 was prepared in an analogous manner to Example 19 using a mixture of Intermediate 9 (0.01 g) and 2-(bromomethyl)naphthalene (0.009 g) to give the title compound (0.0052 g). LC-MS (System A): Rt 2.81 mins, Mass Spectrum m/z 410 [MH$^+$].

Example 24

N-{[4-(3,4-Dichlorobenzyl)morpholin-2-yl]methyl}N'-(2,6-dichloropyridin-4-yl)urea Example 24 was prepared in an analogous manner to Example 1 using a mixture of Intermediate 3 (0.025 g) and 2,6-dichloro-4-isocyanatopyridine (0.0258 g) to give the title compound (0.0165 g). LC-MS (System A): Rt 2.46 mins, Mass Spectrum m/z 463 [MH$^+$].

Example 25

N-(4-Cyanophenyl)-N'-{[4-(3,4-dichlorobenzyl)morpholin-2-yl]methyl}urea

Example 25 was prepared in an analogous manner to Example 1 using a mixture of Intermediate 3 (0.025 g) and 4-isocyanatobenzonitrile (0.0196 g) to give the title compound (0.0325 g). LC-MS (System A): Rt 2.29 mins, Mass Spectrum m/z 419 [MH$^+$].

Example 26

N-{[4-(3-Chlorobenzyl)morpholin-2-yl]methyl}-N'-(4-chlorophenyl)urea

Example 26 was prepared in an analogous manner to Example 19 using a mixture of Intermediate 9 (0.01 g) and 1-(bromomethyl)-3-chlorobenzene (5.4 µl) to give the title compound (0.0023 g). LC-MS (System A): Rt 2.72 mins, Mass Spectrum m/z 394 [MH$^+$].

Example 27

N-[(4-But-3-enylmorpholin-2-yl)methyl]-N'-(4-chlorophenyl)urea

Example 27 was prepared in an analogous manner to Example 19 using a mixture of Intermediate 9 (0.01 g) and 4-bromobut-1-ene (4.1 µl) to give the title compound (0.0027 g).
LC-MS (System A): Rt 2.34 mins, Mass Spectrum m/z 324 [MH$^+$].

Example 28

N-(4-Chlorophenyl)-N'-({4-[2-(phenylthio)ethyl]morpholin-2-ylmethyl)urea

Example 28 was prepared in an analogous manner to Example 19 using a mixture of Intermediate 9 (0.01 g) and [(2-bromoethyl)thio]benzene (0.0089 g) to give the title compound (0.0023 g). LC-MS (System A): Rt 2.77 mins, Mass Spectrum m/z 406 [MH$^+$].

Example 29

N-(4-Chlorophenyl)-N'-[4-(2-methoxyethyl)morpholin-2-yl]methyl}urea

Example 29 was prepared in an analogous manner to Example 19 using a mixture of Intermediate 9 (0.01 g) and 1-bromo-2-methoxyethane (3.8 µl) to give the title compound (0.0041 g). LC-MS (System A): Rt 2.22 mins, Mass Spectrum m/z 328 [MH$^+$].

Example 30

N{[4-(1,1'-Biphenyl-4-ylmethyl)morpholin-2-yl]methyl}N'-(4-chlorophenyl)urea

Example 30 was prepared in an analogous manner to Example 19 using a mixture of Intermediate 9 (0.01 g) and 4-(chloromethyl)-1,1'-biphenyl (0.0083 g) to give the title compound (0.0052 g). LC-MS (System A): Rt 2.95 mins, Mass Spectrum m/z 436 [MH$^+$].

Example 31

N-{[4-(3,4-Dichlorobenzyl)morpholin-2-yl]methyl}-N'-(1-naphthyl)urea

Example 31 was prepared in an analogous manner to Example 1 using a mixture of Intermediate 3 (0.025 g) and 1-isocyanatonaphthalene (19.6 µl) to give the title compound (0.0304 g). LC-MS (System A): Rt 2.43 mins, Mass Spectrum m/z 444 [MH$^+$].

Example 32

N-(1,1'-Biphenyl-4-yl)-N'-{[4-(3,4-dichlorobenzyl)morpholin-2-yl]methyl}urea

Example 32 was prepared in an analogous manner to Example 1 using a mixture of Intermediate 3 (0.025 g) and 4-isocyanato-1,1'-biphenyl (0.0266 g) to give the title compound (0.0314 g). LC-MS (System A): Rt 2.65 mins, Mass Spectrum m/z 470 [MH$^+$].

Example 33

N-{[4-(3,4-Dichlorobenzyl)morpholin-2-yl]methyl}-N'-(4-phenoxyphenyl)urea

Example 33 was prepared in an analogous manner to Example 1 using a mixture of Intermediate 3 (0.025 g) and 1-isocyanato-4-phenoxybenzene (24.6 µl) to give the title compound (0.0171 g). LC-MS (System A): Rt 2.62 mins, Mass Spectrum m/z 486 [MH$^+$].

Example 34

N-{[4-(3,4-Dichlorobenzyl)morpholin-2-yl]methyl}-N'-{4-[(trifluoromethyl)thio]phenyl}urea Example 34 was prepared in an analogous manner to Example 1 using a mixture of Intermediate 3 (0.025 g) and 1-isocyanato-4-[(trifluoromethyl)thio]benzene (21.9 µl) to give the title compound (0.0122 g). LC-MS (System A): Rt 2.70 mins, Mass Spectrum m/z 494 [MH$^+$].

Example 35

N-{[4-(3,4-Dichlorobenzyl)morpholin-2-yl]methyl}-N'-[4-(trifluoromethoxy)phenyl]urea Example 35 was prepared in an analogous manner to Example 1 using a mixture of Intermediate 3 (0.025 g) and 1-isocyanato-4-(trifluoromethoxy)benzene (20.6 µl) to give the title compound (0.0371 g). LC-MS (System A): Rt 2.57 mins, Mass Spectrum m/z 478 [MH$^+$].

Example 36

N-{[4-(3,4-Dichlorobenzyl)morpholin-2-yl]methyl}-N'-[4-(dimethylamino)phenyl]urea Example 36 was prepared in an analogous manner to Example 1 using a mixture of Intermediate 3 (0.025 g) and 4-isocyanato-N,N-dimethylaniline (0.0221 g) to give the title compound (0.031 g). LC-MS (System A): Rt 1.68 mins, Mass Spectrum m/z 437 [MH$^+$].

Example 37

N-(4-Chlorophenyl)-N'-({4-[(5-chlorothien-2-yl)methyl]morpholin-2-yl}methyl)urea Example 37 was prepared in an analogous manner to Example 19 using a mixture of Intermediate 9 (0.01 g) and 2-chloro-5-(chloromethyl)thiophene (0.0068 g) to give the title compound (0.0098 g). LC-MS (System A): Rt 2.84 mins, Mass Spectrum m/z 400 [MH$^+$].

Example 38

N-(4-Chlorophenyl)-N'-{[4-(4-vinylbenzyl)morpholin-2-yl]methyl}urea

Example 38 was prepared in an analogous manner to Example 19 using a mixture of Intermediate 9 (0.01 g) and 1-(chloromethyl)-4-vinylbenzene (0.0062 g) to give the title compound (0.0071 g). LC-MS (System A): Rt 2.72 mins, Mass Spectrum m/z 386 [MH$^+$].

Example 39

2-{2-[({[(4-Chlorophenyl)amino]carbonyl}amino)methyl]morpholin-4-yl}ethyl Benzoate Example 39 was prepared in an analogous manner to Example 19 using a mixture of Intermediate 9 (0.01 g) and 2-bromoethyl benzoate (6.5 µl) to give the title compound (0.007 g). LC-MS (System A): Rt 2.69 mins, Mass Spectrum m/z 418 [MH$^+$].

Example 40

N-(4-Chlorophenyl)-N'-({4-[2-(4-fluorophenoxy)ethyl]morpholin-2-yl}methyl)urea

Example 40 was prepared in an analogous manner to Example 19 using a mixture of Intermediate 9 (0.01 g) and 1-(2-bromoethoxy)-4-fluorobenzene (0.0089 g) to give the title compound (0.007 g). LC-MS (System A): Rt 2.69 mins, Mass Spectrum m/z 408 [MH$^+$].

Example 41

N-(4-Chlorophenyl)-N'-({4-[4-(4-chlorophenyl)-4-oxobutyl]morpholin-2-yl)methyl}urea Example 41 was prepared in an analogous manner to Example 19 using a mixture of Intermediate 9 (0.01 g) and 4-chloro-1-(4-chlorophenyl)butan-1-one (0.0089 g) to give the title compound (0.0043 g). LC-MS (System A): Rt 2.83 mins, Mass Spectrum m/z 450 [MH$^+$].

Example 42

N-(4-Chlorophenyl)-N'-{[4-(3,4-dichlorobenzoyl)morpholin-2-yl]methyl}urea

To a stirred solution of Intermediate 9 (0.05 g) was added a solution of 3,4-dichlorobenzoyl chloride (42.7 mg) in N,N-dimethylformamide (7 ml). The mixture was stirred at 22° C. for 15 h before the solvent was evaporated in vacuo. The residue was purified by eluting through a 1 g silica solid phase extraction cartridge (Varian Bondelut), eluting sequentially with dichloromethane, ether, ethyl acetate, acetone, acetonitrile and methanol, to give the title compound as a white solid (0.080 g). LC/MS (System A) R$_t$ 3.10 min, Mass Spectrum m/z 442 [MH$^+$].

Example 43

N'-{[4-(3,4-Dichlorobenzyl)morpholin-2-yl]methyl}-N-(4-fluorophenyl)-N-methylurea 4-Fluoro-N-methylaniline (0.007 ml) was added to a solution of Intermediate 10 (0.025 g) in anhydrous pyridine (1 ml). The mixture was heated at 110° C. in a thick walled glass vial (Reactivial) for 20 h. The mixture was evaporated to remove the pyridine, and partitioned between ethyl acetate (10 ml) and saturated aqueous sodium bicarbonate solution (10 ml). The organic layer was washed with further sodium bicarbonate (10 ml×5), brine (10 ml), dried (MgSO$_4$), concentrated in vacuo. The residue was purified by chromatography on silica gel (Trikonex flash tube 2002, 2 g), eluting with 70% ethyl acetate in cyclohexane to give the title compound as a pale yellow gum 0.014 g. LCMS (system A) R$_t$ 2.52 min, Mass Spectrum m/z 426 [MH$^+$].

Example 44

Ethyl {2-[({[(4-chlorophenyl)amino]carbonyl}amino)methyl]morpholin-4-yl}(phenyl)acetate Example 44 was prepared in an analogous manner to Example 19 using a mixture of Intermediate 9 (0.01 g) and ethyl bromo(phenyl)acetate (0.029 g) to give the title compound (0.0372 g). LC-MS (System A): Rt 3.43 mins, Mass Spectrum m/z 432 [MH$^+$].

Example 45

2-{2-[({[(4-Chlorophenyl)amino]carbonylamino)methyl]morpholin-4-yl}-2-phenylacetamide Example 45 was prepared in an analogous manner to Example 19 using a mixture of Intermediate 9 (0.01 g) and 2-bromo-2-phenylacetamide (0.028 g) to give the title compound (0.0296 g). LC-MS (System A): Rt 2.75 mins, Mass Spectrum m/z 401 [MH$^+$].

Example 46

N-(4-Chlorophenyl)-N'-{[4-(cyanomethyl)morpholin-2-yl]methyl}urea

Example 46 was prepared in an analogous manner to Example 19 using a mixture of Intermediate 9 (0.01 g) and bromoacetonitrile (2.8 µl) to give the title compound (0.0039 g).

LC-MS (System A): Rt 2.79 mins, Mass Spectrum m/z 309 [MH$^+$].

Example 47

N-(4-Chlorobenzyl)-N'-{[4-(3,4-dichlorobenzyl)morpholin-2-yl]methyl}urea

A suspension of 4-{[(polystyrene resin)methyl]thio}phenyl 4-nitrophenyl carbonate (Prepared as described in Tetrahedron Lett. (1998), 39(22), 3631–3634, 1.5 g @ 0.99 mmol/g) in N,N-dimethylformamide (15 ml) was shaken with Intermediate 3 (0.80 g) at 22° C. for 1 h. The resin was filtered, washed with N,N-dimethylformamide (×2), dichloromethane (×3) and N,N-dimethylformamide. The resin was again shaken with N,N-dimethylformamide (15 ml) and Intermediate 3 (0.80 g) at 22° C. for 1 h before being filtered, washed with N,N-dimethylformamide (×2), dichloromethane (×3) and ether (×2) and dried in vacuo to give the intermediate resin 4-{[(polystyrene resin)methyl]thio}phenyl [4-(3,4-dichlorobenzyl)morpholin-2-yl]methylcarbamate as orange beads. To a sample of this resin (50 mg) in a test tube was added 4-chlorobenzylamine (9.6 µl) and 1 drop of 1-methyl-2-pyrrolidinone, and the mixture was placed into a microwave oven and heated at full power (600W) for 5 min. Dichloromethane (2 ml) and formylpolystyrene resin were added, and the mixture was shaken at 22° C. for 18 h. The suspension was poured onto a 1 g solid phase extraction (Isolute SCX sulphonic acid) column which was then washed with methanol before eluting with 10% 0.880 ammonia solution in methanol. The basic fraction was evaporated in vacuo to give a cream solid which was further purified by eluting through a 1 g silica solid phase extraction cartridge (Varian Bondelut) eluting sequentially with dichloromethane, ether, ethyl acetate, acetone, acetonitrile and methanol, to give the title compound as a white solid (4.7 mg). LC/MS (System A) R$_t$ 2.70 min, Mass Spectrum m/z 442 [MH$^+$].

Example 48

N-(3-Chlorobenzyl)-N'-{[4-(3,4-dichlorobenzyl)morpholin-2-yl]methyl}urea

Example 48 was prepared in an analogous manner to Example 47 using a mixture of Intermediate 3 (0.025 g) and 1-(3-chlorophenyl)methanamine (9.6 µl) to give the title compound (0.0092 g). LC-MS (System A): Rt 2.73 mins, Mass Spectrum m/z 442 [MH$^+$].

Example 49

N-(2-Chlorobenzyl)-N'-{[4-(3,4-dichlorobenzyl)morpholin-2-yl]methyl}urea

Example 49 was prepared in an analogous manner to Example 47 using a mixture of Intermediate 3 (0.025 g) and 1-(2-chlorophenyl)methanamine (9.6 µl) to give the title compound (0.008 g). LC-MS (System A): Rt 2.74 mins, Mass Spectrum m/z 442 [MH$^+$].

Example 50

N-(4-Chlorophenyl)-N'-[4-(3,4-dichlorobenzyl)morpholin-2-yl]methyl}urea (ISOMER 1)

Chiral separation from the racemic mixture of Example 14:

Example 14 (racemic mixture, 0.040 g) was separated into its single enantiomers of unknown configuration with a chiral preparative HPLC system. The separation was carried out using a Chiralpak AD column (2 cm×25 cm), eluting with 60% ethanol in heptane (15 ml/min over 25 mins, UV detection λ=215 nm) to give the title compound as a white solid (0.012 g).

Preparative HPLC retention time 7.5 min.

Example 51

N-(4-Chlorophenyl)-N'-{[4-(3,4-dichlorobenzyl)morpholin-2-yl]methyl}urea (ISOMER 2)

Example 51 was prepared in an analogous manner to Example 50 yielding the title compound as a white solid (0.012 g). Preparative HPLC retention time 11 min.

Example 52

N-[3-({[({[4-(3,4-Dichlorobenzyl)morpholin-2-yl]methyl}amino)carbonyl]amino}methyl)phenyl]acetamide Formate Example 52 was prepared in an analogous manner to Example 43 from Intermediate 10 (0.04 g) and 3-acetamidobenzylamine (0.022 g), and purified by Mass Directed Automated Preparative HPLC to yield the title compound (0.008 g).

LC-MS (System A) Rt 2.47 mins. Mass Spectrum m/z 465 [MH$^+$].

Example 53

4-({[({[4-(3,4-Dichlorobenzyl)morpholin-2-yl]methyl}amino)carbonyl]amino}methyl)benzamide Example 53 was prepared in an analogous manner to Example 47 from Intermediate 3 (0.025 g) and 4-aminomethylbenzamide (0.016 g) to yield the title compound (0.0083 g).

LC-MS (System A) Rt 2.16 mins. Mass Spectrum m/z 451, 453 [MH$^+$].

Example 54

4-({[({[(2S)-4-(3,4-Dichlorobenzyl)morpholin-2-yl]methyl}amino)carbonyl]amino}methyl)benzamide Example 54 was prepared in an analogous manner to Example 43 from Intermediate 13 (0.079 g) and 4-aminomethylbenzamide (0.032 g) using N,N-dimethylformamide as solvent to yield the title compound (0.0837 g).

LC-MS (System A) Rt 2.27 mins. Mass Spectrum m/z 451, 453 [MH$^+$].

Chiral analytical HPLC, eluent 15% EtOH/n-heptane: Rt 41.8 min.

Example 55

4-({[({[(2R)-4-(3,4-Dichlorobenzyl)morpholin-2-yl]methyl}amino)carbonyl]amino}methyl)benzamide Example 55 was prepared in an analogous manner to Example 43 from Intermediate 14 (0.109 g) and 4-aminomethylbenzamide (0.045 g) using N,N-dimethylformamide as solvent to yield the title compound (0.0828 g).

LC-MS (System A) Rt 2.27 mins. Mass Spectrum m/z 451, 453 [MH$^+$].

Chiral analytical HPLC, eluent 15% EtOH/n-heptane: Rt 36.7 min.

Example 56

N-{[4-(3,4-Dichlorobenzyl)morpholin-2-yl]methyl}-N'-prop-2-ynylurea

Example 56 was prepared in an analogous manner to Example 43 from Intermediate 10 (0.040 g) and propargylamine (0.006 g) using dichloromethane and triethylamine at a temperature of 22° C. to yield the title compound (0.028 g).

LC-MS (system A) Rt 2.22 mins. Mass Spectrum m/z 356 [MH$^+$].

Chiral analytical HPLC, eluent 15% EtOH/n-heptane: Rt 12.25 min and 14.1 min.

Example 57

N-{[(2S)-4-(3,4-Dichlorobenzyl)morpholin-2-yl]methyl}-N'-prop-2-ynylurea

Example 57 was prepared in an analogous manner to Example 43 from Intermediate 13 (0.1 g) and propargylamine (0.014 g) using dichloromethane and triethylamine at a temperature of 22° C. to yield the title compound (0.064 g).

LC-MS (System A) Rt 2.40 mins. Mass Spectrum m/z 356 [MH$^+$].

Chiral analytical HPLC, eluent 15% EtOH/n-heptane: Rt 14.14 min.

Example 58

N-{[(2R)-4-(3,4-Dichlorobenzyl)morpholin-2-yl]methyl}-N'-prop-2-ynylurea

Example 58 was prepared in an analogous manner to Example 43 from Intermediate 14 (0.12 g) and propargylamine (0.014 g) using dichloromethane and triethylamine at a temperature of 22° C. to yield the title compound (0.057 g).

LC-MS (System A) Rt 2.37 mins. Mass Spectrum m/z 356 [MH$^+$].

Chiral analytical HPLC, eluent 15% EtOH/n-heptane: Rt 12.26 min.

Examples 59–122

|    | Name | Preparation analogous to | Characterising Data |
| --- | --- | --- | --- |
| 59 | N-benzyl-N'-{[(2R,5S)-4-(3,4-dichlorobenzyl)-5-methylmorpholin-2-yl]methyl}urea | Example 1 | LC-MS (System A): Rt 2.89 mins. Mass Spectrum m/z 422 [MH$^+$]. |
| 60 | N-benzyl-N'-{[(2S,5R)-4-(3,4-dichlorobenzyl)-5-methylmorpholin-2-yl]methyl}urea | Example 1 | LC-MS (System A): Rt 2.68 mins. Mass Spectrum m/z 422 [MH$^+$]. Normal phase Analytical HPLC Rt 14.2 mins. |
| 61 | 4-({[({[4-(3,4-dichlorobenzyl)morpholin-2-yl]methyl}amino)carbonyl]amino}methyl)benzenesulfonamide | Example 47 | LC-MS (System A): Rt 2.40 mins. Mass Spectrum m/z 487 [MH$^+$]. |
| 62 | N'-{[4-(3,4-dichlorobenzyl)morpholin-2-yl]methyl}-N-methyl-N-pyridin-4-ylurea | Example 43 | LC-MS (System A): Rt 2.06 mins. Mass Spectrum m/z 409 [MH$^+$]. |
| 63 | N-{[(2S)-4-(3,4-dichlorobenzyl)morpholin-2-yl]methyl}-N'-(4-methoxybenzyl)urea | Example 50 | LC-MS (System A): Rt 2.68 mins. Chiral preparative HPLC, eluent 20% ethanol/n-heptane, Rt 18.7 min. |
| 64 | N,N'-bis{[4-(3,4-dichlorobenzyl)morpholin-2-yl]methyl}urea | Example 43 | LC-MS (System A): Rt 2.79 mins. Mass Spectrum m/z 576 [MH$^+$]. |
| 65 | N-{[4-(3,4-dichlorobenzyl)morpholin-2-yl]methyl}-N'-(3,4-dimethoxybenzyl)urea | Example 47 | LC-MS (System A): Rt 2.42 mins. Mass Spectrum m/z 468, 470 [MH$^+$]. |
| 66 | N-(3-cyanobenzyl)-N'-{[4-(3,4-dichlorobenzyl)morpholin-2-yl]methyl}urea | Example 47 | LC-MS (System A): Rt 2.48 mins. Mass Spectrum m/z 433, 435 [MH$^+$]. |
| 67 | N-{[4-(3,4-dichlorobenzyl)morpholin-2- | Example 47 | LC-MS (System A): Rt 1.88 mins. |

-continued

| | Name | Preparation analogous to | Characterising Data |
|---|---|---|---|
| | yl]methyl}-N'-(pyridin-3-ylmethyl)urea | | Mass Spectrum m/z 409, 411 [MH+]. |
| 68 | N-{[4-(3,4-dichlorobenzyl)morpholin-2-yl]methyl}-N'-(3-methoxybenzyl)urea | Example 47 | LC-MS (System A): Rt 2.54 mins. Mass Spectrum m/z 438, 440 [MH+]. |
| 69 | N-{[4-(3,4-dichlorobenzyl)morpholin-2-yl]methyl}-N'-[3-(trifluoromethoxy)benzyl]urea | Example 47 | LC-MS (System A): Rt 2.88 mins. Mass Spectrum m/z 492, 494 [MH+]. |
| 70 | N-{[4-(3,4-dichlorobenzyl)morpholin-2-yl]methyl}-N'-[4-(trifluoromethyl)benzyl]urea | Example 47 | LC-MS (System A): Rt 2.83 mins. Mass Spectrum m/z 476, 478 [MH+]. |
| 71 | N-{[4-(3,4-dichlorobenzyl)morpholin-2-yl]methyl}-N'-(4-(1,2,3-thiadiazol-4-yl)benzyl]urea | Example 47 | LC-MS (System A): Rt 2.59 mins. Mass Spectrum m/z 492, 494 [MH+]. |
| 72 | N-{[4-(3,4-dichlorobenzyl)morpholin-2-yl]methyl}-N'-[4-(trifluoromethoxy)benzyl]urea | Example 47 | LC-MS (System A): Rt 2.88 mins. Mass Spectrum m/z 492, 494 [MH+]. |
| 73 | N-(3,5-dichlorobenzyl)-N'-{[4-(3,4-dichlorobenzyl)morpholin-2-yl]methyl}urea | Example 47 | LC-MS (System A): Rt 2.92 mins. Mass Spectrum m/z 476, 478, 480 [MH+]. |
| 74 | N-{[4-(3,4-dichlorobenzyl)morpholin-2-yl]methyl}-N'-[3-(trifluoromethyl)benzyl]urea | Example 47 | LC-MS (System A): Rt 2.82 mins. Mass Spectrum m/z 476, 478 [MH+]. |
| 75 | N-{[4-(3,4-dichlorobenzyl)morpholin-2-yl]methyl}-N'-(2,4-difluorobenzyl)urea | Example 136 | LC-MS (System A): Rt 2.88 mins. Mass Spectrum m/z 444, 446 [MH+]. |
| 76 | N-{[4-(3,4-dichlorobenzyl)morpholin-2-yl]methyl}-N'-(3,4-difluorobenzyl)urea | Example 47 | LC-MS (System A): Rt 2.65 mins. Mass Spectrum m/z 444, 446 [MH+]. |
| 77 | N-{[4-(3,4-dichlorobenzyl)morpholin-2-yl]methyl}-N'-(3-fluorobenzyl)urea | Example 47 | LC-MS (System A): Rt 2.58 mins. Mass Spectrum m/z 426, 428 [MH+]. |
| 78 | N-{[4-(3,4-dichlorobenzyl)morpholin-2-yl]methyl}-N'-(1H-indol-5-ylmethyl)urea | Example 47 | LC-MS (System A): Rt 2.51 mins. Mass Spectrum m/z 447, 449 [MH+]. |
| 79 | N-{[4-(3,4-dichlorobenzyl)morpholin-2-yl]methyl}-N'-(1H-indol-4-ylmethyl)urea | Example 47 | LC-MS (System A): Rt 2.50 mins. Mass Spectrum m/z 447, 449 [MH+]. |
| 80 | N-(3,4-dichlorobenzyl)-N'-{[4-(3,4-dichlorobenzyl)morpholin-2-yl]methyl}urea | Example 47 | LC-MS (System A): Rt 2.89 mins. Mass Spectrum m/z 476, 478, 480 [MH+]. |
| 81 | 3-({[({[4-(3,4-dichlorobenzyl)morpholin-2-yl]methyl}amino)carbonyl]amino}methyl)-N-methylbenzamide | Example 131 | LC-MS (System A): Rt 2.29 mins. Mass Spectrum m/z 465, 467 [MH+]. |
| 82 | N-{[4-(3,4-dichlorobenzyl)morpholin-2-yl]methyl}-N'-(2,3-dihydro-1-benzofuran-5-ylmethyl)urea | Example 136 | LC-MS (System A): Rt 2.77 mins. Mass Spectrum m/z 450, 452 [MH+]. |
| 83 | N-{[4-(3,4-dichlorobenzyl)morpholin-2-yl]methyl}-N'-[(5-methylisoxazol-3-yl)methyl]urea | Example 47 | LC-MS (System A): Rt 2.27 mins. Mass Spectrum m/z 413, 415 [MH+]. |
| 84 | N-{[4-(3,4-dichlorobenzyl)morpholin-2-yl]methyl}-N'-[2-(trifluoromethoxy)benzyl]urea | Example 47 | LC-MS (System A): Rt 2.82 mins. Mass Spectrum m/z 492, 494 [MH+]. |
| 85 | methyl 3-({[({[4-(3,4-dichlorobenzyl)morpholin-2-yl]methyl}amino)carbonyl]amino}methyl)benzoate | Example 47 | LC-MS (System A): Rt 2.55 mins. Mass Spectrum m/z 466, 468 [MH+]. |
| 86 | N-{[4-(3,4-dichlorobenzyl)morpholin-2- | Example 47 | LC-MS (System A): Rt 2.78 mins. Mass |

| | Name | Preparation analogous to | Characterising Data |
|---|---|---|---|
| | yl]methyl}-N'-[2-(trifluoromethyl)benzyl]urea | | Spectrum m/z 476, 478 [MH⁺]. |
| 87 | N-{[4-(3,4-dichlorobenzyl)morpholin-2-yl]methyl}-N'-(4-fluorobenzyl)urea | Example 47 | LC-MS (System A): Rt 2.58 mins. Mass Spectrum m/z 426, 428 [MH⁺]. |
| 88 | N-{[4-(3,4-dichlorobenzyl)morpholin-2-yl]methyl}-N'-(2-fluorobenzyl)urea | Example 47 | LC-MS (System A): Rt 2.55 mins. Mass Spectrum m/z 426, 428 [MH⁺]. |
| 89 | N-{[4-(3,4-dichlorobenzyl)morpholin-2-yl]methyl}-N'-(4-isopropoxybenzyl)urea | Example 47 | LC-MS (System A): Rt 2.73 mins. Mass Spectrum m/z 466, 468 [MH⁺]. |
| 90 | N-{[4-(3,4-dichlorobenzyl)morpholin-2-yl]methyl}-N'-(2,4-dimethoxybenzyl)urea | Example 47 | LC-MS (System A): Rt 2.59 mins. Mass Spectrum m/z 468, 470 [MH⁺]. |
| 91 | N-{[4-(3,4-dichlorobenzyl)morpholin-2-yl]methyl}-N'-[2-(4-methoxyphenyl)ethyl]urea | Example 47 | LC-MS (System A): Rt 2.60 mins. Mass Spectrum m/z 452, 454 [MH⁺]. |
| 92 | N-[2-(4-tert-butoxyphenyl)ethyl]-N'-{[4-(3,4-dichlorobenzyl)morpholin-2-yl]methyl}urea | Example 47 | LC-MS (System A): Rt 2.84 mins. Mass Spectrum m/z 494, 496 [MH⁺]. |
| 93 | N-{[4-(3,4-dichlorobenzyl)morpholin-2-yl]methyl}-N'-(thien-2-ylmethyl)urea | Example 43 | LC-MS (System A): Rt 2.58 mins. Mass Spectrum m/z 414 [MH⁺]. |
| 94 | N-{[4-(3,4-dichlorobenzyl)morpholin-2-yl]methyl}-N'-(2-thien-2-ylethyl)urea | Example 47 | LC-MS (System A): Rt 2.54 mins. Mass Spectrum m/z 428, 430 [MH⁺]. |
| 95 | N-{[4-(3,4-dichlorobenzyl)morpholin-2-yl]methyl}-N'-[3-(dimethylamino)benzyl]urea | Example 47 | LC-MS (System A): Rt 2.26 mins. Mass Spectrum m/z 451, 453 [MH⁺]. |
| 96 | N-{[4-(3,4-dichlorobenzyl)morpholin-2-yl]methyl}-N'-propylurea | Example 47 | LC-MS (System A): Rt 2.26 mins. Mass Spectrum m/z 360, 362 [MH⁺]. |
| 97 | N-{[4-(3,4-dichlorobenzyl)morpholin-2-yl]methyl}-N'-[2-(methylthio)benzyl]urea | Example 47 | LC-MS (System A): Rt 2.67 mins. Mass Spectrum m/z 454, 456 [MH⁺]. |
| 98 | N-(4-cyanobenzyl)-N'-{[4-(3,4-dichlorobenzyl)morpholin-2-yl]methyl}urea | Example 47 | LC-MS (System A): Rt 2.47 mins. Mass Spectrum m/z 433, 435 [MH⁺]. |
| 99 | 2-{[({[4-(3,4-dichlorobenzyl)morpholin-2-yl]methyl}amino)carbonyl]amino}-N-methylethanesulfonamide | Example 43 | LC-MS (System A): Rt 2.35 mins. Mass Spectrum m/z 438 [MH⁺]. |
| 100 | N-{[4-(3,4-dichlorobenzyl)morpholin-2-yl]methyl}-N'-(4-hydroxybut-2-ynyl)urea | Example 43 | LC-MS (System A): Rt 2.14 mins. Mass Spectrum m/z 386 [MH⁺]. |
| 101 | N-allyl-N'-{[(2S)-4-(3,4-dichlorobenzyl)morpholin-2-yl]methyl}urea | Example 50 | LC-MS (System A): Rt 2.40 mins. Chiral preparative HPLC, eluent 20% ethanol/n-heptane, Rt 9.3 min. |
| 102 | N-but-3-enyl-N'-{[4-(3,4-dichlorobenzyl)morpholin-2-yl]methyl}urea | Example 43 | LC-MS (System A): Rt 2.40 mins. Mass Spectrum m/z 372 [MH⁺]. |
| 103 | N-{[4-(3,4-dichlorobenzyl)morpholin-2-yl]methyl}-N'-[2-(pyrrolidin-1-ylsulfonyl)ethyl]urea | Example 43 | LC-MS (System A): Rt 2.19 mins. Mass Spectrum m/z 479 [MH⁺]. |
| 104 | N'-{[4-(3,4-dichlorobenzyl)morpholin-2-yl]methyl}-N-(4-methoxybenzyl)-N-methylurea | Example 43 | LC-MS (System A): Rt 2.81 mins. Mass Spectrum m/z 452 [MH⁺]. |
| 105 | methyl 4-({[({[4-(3,4-dichlorobenzyl)morpholin-2- | Example 136 | LC-MS (System A): Rt 2.65 mins. |

-continued

| | Name | Preparation analogous to | Characterising Data |
|---|---|---|---|
| | yl]methyl}amino)carbonyl]amino}methyl)benzoate | | Mass Spectrum m/z 466 [MH$^+$]. |
| 106 | 4-({[({[4-(3,4-dichlorobenzyl)morpholin-2-yl]methyl}amino)carbonyl]amino}methyl)-N-(1,3-thiazol-2-yl)benzenesulfonamide | Example 136 | LC-MS (System A): Rt 2.61 mins. Mass Spectrum m/z 570, 572 [MH$^+$]. |
| 107 | N-{[4-(3,4-dichlorobenzyl)morpholin-2-yl]methyl}-N'-({5-[(dimethylamino)methyl]-2-furyl}methyl)urea | Example 136 | LC-MS (System A): Rt 1.95 mins. Mass Spectrum m/z 455, 457 [MH$^+$]. |
| 108 | N-{[4-(3,4-dichlorobenzyl)morpholin-2-yl]methyl}-N'-[(3-methoxyisothiazol-5-yl)methyl]urea | Example 136 | LC-MS (System A): Rt 2.52 mins. Mass Spectrum m/z 445, 447 [MH$^+$]. |
| 109 | N-{[4-(3,4-dichlorobenzyl)morpholin-2-yl]methyl}-N'-[(4-methyl-1,3-thiazol-2-yl)methyl]urea | Example 136 | LC-MS (System A): Rt 2.35 mins. Mass Spectrum m/z 429, 431 [MH$^+$]. |
| 110 | N-{[4-(3,4-dichlorobenzyl)morpholin-2-yl]methyl}-N'-[(6-methoxypyridin-3-yl)methyl]urea | Example 136 | LC-MS (System A): Rt 2.40 mins. Mass Spectrum m/z 439, 441 [MH$^+$]. |
| 111 | 5-({[({[4-(3,4-dichlorobenzyl)morpholin-2-yl]methyl}amino)carbonyl]amino}methyl)nicotinamide | Example 136 | LC-MS (System A): Rt 2.10 mins. Mass Spectrum m/z 452, 454 [MH$^+$]. |
| 112 | N-{[4-(3,4-dichlorobenzyl)morpholin-2-yl]methyl}-N'-(pyrazin-2-ylmethyl)urea | Example 136 | LC-MS (System A): Rt 2.14 mins. Mass Spectrum m/z 410, 412 [MH$^+$]. |
| 113 | N-{[4-(3,4-dichlorobenzyl)morpholin-2-yl]methyl}-N'-(1,3-thiazol-2-ylmethyl)urea | Example 136 | LC-MS (System A): Rt 2.26 mins. Mass Spectrum m/z 415, 417 [MH$^+$]. |
| 114 | N-{[4-(3,4-dichlorobenzyl)morpholin-2-yl]methyl}-N'-[(2-methyl-1,3-thiazol-4-yl)methyl]urea | Example 136 | LC-MS (System A): Rt 2.34 mins. Mass Spectrum m/z 429, 431 [MH$^+$]. |
| 115 | methyl 2-({[({[4-(3,4-dichlorobenzyl)morpholin-2-yl]methyl}amino)carbonyl]amino}methyl)-4-methyl-1,3-thiazole-5-carboxylate | Example 136 | LC-MS (System A): Rt 2.49 mins. Mass Spectrum m/z 487, 489 [MH$^+$]. |
| 116 | N-[(5-amino-1-phenyl-1H-pyrazol-4-yl)methyl]-N'-{[4-(3,4-dichlorobenzyl)morpholin-2-yl]methyl}urea | Example 136 | LC-MS (System A): Rt 2.45 mins. Mass Spectrum m/z 489, 491 [MH$^+$]. |
| 117 | N-{[4-(3,4-dichlorobenzyl)morpholin-2-yl]methyl}-N'-(1H-pyrrolo[2,3-b]pyridin-3-ylmethyl)urea | Example 136 | LC-MS (System A): Rt 2.26 mins. Mass Spectrum m/z 448, 450 [MH$^+$]. |
| 118 | N-{[4-(3,4-dichlorobenzyl)morpholin-2-yl]methyl}-N'-({5-[(dimethylamino)methyl]thien-2-yl}methyl)urea | Example 136 | LC-MS (System A): Rt 1.98 mins. Mass Spectrum m/z 471, 473 [MH$^+$]. |
| 119 | N-{[4-(3,4-dichlorobenzyl)morpholin-2-yl]methyl}-N'-(2-furylmethyl)urea | Example 136 | LC-MS (System A): Rt 2.42 mins. Mass Spectrum m/z 398, 400 [MH$^+$]. |
| 120 | N-{[4-(3,4-dichlorobenzyl)morpholin-2-yl]methyl}-N'-[(2-methyl-2H-tetraazol-5-yl)methyl]urea | Example 136 | LC-MS (System A): Rt 2.21 mins. Mass Spectrum m/z 414, 416 [MH$^+$]. Chiral analytical HPLC, eluent 30% EtOH/n-heptane(0.1% TFA), Rt 9.99 min and 12.75 min. |
| 121 | N-but-3-ynyl-N'-{[4-(3,4-dichlorobenzyl)morpholin-2-yl]methyl}urea | Example 43 | LC-MS (System A): Rt 2.32 mins. Mass Spectrum m/z 370 [MH$^+$]. |

| | Name | Preparation analogous to | Characterising Data |
|---|---|---|---|
| 122 | N-{[4-(3,4-dichlorobenzyl)morpholin-2-yl]methyl}-N'-[3-(phenylsulfonyl)propyl]urea | Example 43 | LC-MS (System A): Rt 2.46 mins. Mass Spectrum m/z 500 [MH$^+$]. |

Example 123

4-({[({[4-(3,4-Dichlorobenzyl)morpholin-2-yl]methyl}amino)carbonyl]amino}methyl)benzoic Acid Compound with N,N,N-triethylamine (1:1)

Sodium hydroxide (0.09 g) was added to a stirred solution of Example 105 (0.522 g) in a mixture of water (5 ml) and methanol (5 ml) at 20° C., and stirring was continued at 20° C. for 18 h. The pH of the mixture was adjusted to approximately 6 by the addition of 2M aqueous sodium hydroxide and the mixture was applied in two equal portions to ion exchange cartridges (10 g Isolute SCX pre-conditioned with methanol). Elution with methanol (3 column volumes) followed 10% triethylamine in methanol (2 column volumes) and evaporation of the first basic fractions in vacuo gave the title compound as a tan solid (0.468 g).

LCMS (System A) R$_t$ 2.60 min Mass Spectrum m/z 452 [MH$^+$]

Example 124

4-({[({[(2S)-4-(3,4-Dichlorobenzyl)morpholin-2-yl]methyl}amino)carbonyl]amino}methyl)benzamide Hydrochloride 4.0M hydrogen chloride in 1,4-dioxane (2.0 ml) was added to a stirred solution of Example 54 (0.100 g) in methanol (10 ml), and stirring was continued at 22° C. for 1 h. The solvents were evaporated under a stream of nitrogen and the residue re-dissolved in methanol (4 ml). Toluene (4 ml) was added, and the solvents were again evaporated under a stream of nitrogen. The residue was re-dissolved in methanol (4 ml), toluene (4 ml) added, and the solvents again evaporated under a stream of nitrogen. The white residue was triturated in ether and the solvent evaporated under a stream of nitrogen before being dried in vacuo to give the title compound as a white solid (0.117 g).

LCMS (System A) R$_t$ 2.25 min Mass Spectrum m/z 451 [MH$^+$]

$^1$H NMR (D6 DMSO): 11.45δ(1H, br.s, NH$^+$), 7.97–7.92δ (2H, d+br.s, Aromatic CH+NH) 7.82δ(2H, ½AA'BB', 2×Aromatic CH), 7.75δ(1H, d, Aromatic CH), 7.59δ(1H, dd, Aromatic CH), 7.32δ(1H, br.s, NH), 7.28δ(2H, ½A'BB', 2×Aromatic CH), 6.62, 6.28δ(2H, 2×v.br.s, CONH$_2$), 4.35δ (2H, AB, CH$_2$), 4.25δ(2H, s, CH$_2$), 3.95δ(1H, dd, CH), 3.88–3.79δ(2H, m, 2×CH), 3.28δ(1H, br.d, CH), 3.25–3.18δ (2H, br.m, 2×CH), 3.09δ(1H, dd, CH), 3.00δ(1H, br.m, CH), 2.78δ(1H, m, CH)

Example 125

N-{[(2S)-4-(2,3-dichlorobenzyl)morpholin-2-yl]methyl}-N'-prop-2-ynylurea

A solution of Intermediate 22 (0.024 g) in dichloromethane (1 ml) was stirred with Intermediate 20 (0.033 g) and N,N-diisopropylethylamine (0.022 ml) for 3 h at 23° C. The solvent was removed in vacuo and the residue was purified by solid phase extraction (Isolute SCX sulphonic acid column) eluting with methanol followed by 10% 0.880 ammonia solution in methanol. The basic fraction was concentrated in vacuo, and the residue was dissolved in dichloromethane (5 ml), and the solution shaken with polystyrene methyl isocyanate resin (Argonaut technologies, 0.256 g, 1.43 mmol/g) for 16 h. The solution Was drained from the resin and the resin washed with dichloromethane (8 ml); the combined filtrate and washings were concentrated in vacuo to give the title compound as a pale yellow gum (0.02 g).

LC/MS (System A) Rt 2.17 min, Mass spectrum m/z 356 [MH$^+$].

Example 126

N-({(2S)-4-[(5-chlorothien-2-yl)methyl]morpholin-2-yl}methyl)-N'-prop-2-ynylurea Example 126 was prepared in an analogous manner to Example 125 from Intermediate 23, (0.030 g). Further purification using a silica gel solid phase extraction cartridge (1 g Varian Bond Elut), eluting with 0–5% methanol in ethyl acetate, gave the title compound as a clear gum (0.025 g).

LC/MS (System A) Rt 1.95 min Mass spectrum m/z 328 [MH$^+$].

Example 127

N-{[(2S)-4-(3-chlorobenzyl)morpholin-2-yl]methyl}-N'-prop-2-ynylurea

Example 127 was prepared in an analogous manner to Example 125 from Intermediate 19 (0.029 g). Further purification using a silica gel solid phase extraction cartridge (1 g Varian Bond Elut), eluting with 0–5% methanol in ethyl acetate, gave the title compound as a clear gum (0.021 g).

LC/MS (System A) Rt 1.93 min Mass spectrum m/z 322 [MH$^+$].

Examples 128–130

| | Name | Preparation analogous to | Characterising Data |
|---|---|---|---|
| 128 | 3-({[({[4-(3,4-dichlorobenzyl)morpholin-2-yl]methyl}amino)carbonyl]amino}methyl)-N,N-dimethylbenzamide | Example 131 | LC-MS (System A): Rt 2.32 mins. Mass Spectrum m/z 479, 481 [MH$^+$]. |
| 129 | 3-({[({[4-(3,4-dichlorobenzyl)morpholin-2-yl]methyl}amino)carbonyl]amino}methyl)-N-ethylbenzamide | Example 131 | LC-MS (System A): Rt 2.33 mins. Mass Spectrum m/z 479, 481 [MH$^+$]. |
| 130 | N-cyclopropyl-3-({[({[4-(3,4-dichlorobenzyl)morpholin-2-yl]methyl}amino)carbonyl]amino}methyl)benzamide | Example 131 | LC-MS (System A): Rt 2.34 mins. Mass Spectrum m/z 491, 493 [MH$^+$]. |

Chiral analytical HPLC, eluent 15% ethanol in n-heptane, Rt 24.0 min and 27.7 min.

Examples 132–135

| | Name | Preparation analogous to | Characterising Data |
|---|---|---|---|
| 132 | 4-({[({[4-(3,4-dichlorobenzyl)morpholin-2-yl]methyl}amino)carbonyl]amino}methyl)-N,N-dimethylbenzamide | Example 131 | LC-MS (System A): Rt 2.30 mins. Mass Spectrum m/z 479, 481 [MH$^+$]. |
| 133 | 4-({[({[4-(3,4-dichlorobenzyl)morpholin-2-yl]methyl}amino)carbonyl]amino}methyl)-N-ethylbenzamide | Example 131 | LC-MS (System A): Rt 2.28 mins. Mass Spectrum m/z 479, 481 [MH$^+$]. |
| 134 | N-cyclopropyl-4-({[({[4-(3,4-dichlorobenzyl)morpholin-2-yl]methyl}amino)carbonyl]amino}methyl)benzamide | Example 131 | LC-MS (System A): Rt 2.26 mins. Mass Spectrum m/z 491, 493 [MH$^+$]. |
| 135 | N-{[3-(4-chlorophenyl)isoxazol-5-yl]methyl}-N'-{[(2S)-4-(3,4-dichlorobenzyl)morpholin-2-yl]methyl}urea | Example 136 | LC-MS (System A): Rt 2.98 mins. Mass Spectrum m/z 509, 511 [MH$^+$]. |

Example 131

4-({[({[4-(3,4-Dichlorobenzyl)morpholin-2-yl]methyl}amino)carbonyl]amino}methyl)-N-methylbenzamide Example 123 (0.050 g), 1-hydroxybenzotriazole (0.066 g) and 1-(3-dimethylaminopropyl)-3-ethylcarbodiimide hydrochloride (0.116 g) were stirred in N,N-dimethylformamide (4.2 ml) and N,N-diisopropylethylamine (0.132 ml) was added to the mixture. Stirring was continued at 20° C. until a clear solution was obtained. 2.0M methylamine in tetrahydrofuran (0.379 ml) was added to a portion of the mixture (1.0 ml) and the mixture was stirred at 20° C. under nitrogen for 17 h. The mixture was applied in two equal portions to ion exchange cartridges (2×2 g Isolute SCX pre-conditioned with methanol). Elution with methanol (3 column volumes) followed by 10% 0.880 ammonia in methanol (2 column volumes) and evaporation of the basic fractions in vacuo gave the crude product. Purification by Biotage flash chromatography on a silica gel cartridge (8 g), eluting with 100:8:1 dichloromethane/ethanol/0.880 ammonia, gave the title compound as a white solid (0.0124 g).

LCMS (System A) R$_t$ 2.22 min, Mass Spectrum m/z 465 [MH$^+$].

Example 136

N-{[(2S)-4-(3,4-dichlorobenzyl)morpholin-2-yl]methyl}-N'-[(2-methyl-2H-tetraazol-5-yl)methyl]urea Intermediate 30 (0.041 g) was added to a stirred solution of Intermediate 29 (0.110 g) in N,N-dimethylformamide (2 ml) at 22° C., and N,N-diisopropylethylamine (0.052 ml) was added. After stirring for 20 h, the mixture was applied in two equal portions to ion exchange cartridges (10 g Isolute SCX pre conditioned with methanol). Elution with methanol (3 column volumes) followed by 10% 0.880 ammonia in methanol (2 column volumes) and evaporation of the first basic fractions in vacuo gave the crude product. Purification by Biotage flash chromatography on silica gel (8 g cartridge), eluting with 100:8:1 dichloromethane/ethanol/0.880 ammonia, gave the title compound as a white solid, (0.0828 g).

LC/MS (System A) Rt 2.19 min Mass Spectrum m/z 414 [MH$^+$].

Chiral analytical HPLC, eluent 30% ethanol/0.1% trifluoroacetic acid in n-heptane, Rt 10.1 min.

Examples 137–144

| | Name | Preparation analogous to | Characterising Data |
|---|---|---|---|
| 137 | 4-(2-{[({[(2S)-4-(3,4-dichlorobenzyl)morpholin-2-yl]methyl}amino)carbonyl]amino}ethyl)benzenesulfonamide | Example 136 | LC-MS (System A): Rt 2.38 mins. Mass Spectrum m/z 501, 503 [MH$^+$]. |
| 138 | 3-({[({[(2S)-4-(3,4-dichlorobenzyl)morpholin-2-yl]methyl}amino)carbonyl]amino}methyl)-N-methylbenzamide | Example 136 | LC-MS (System A): Rt 2.28 mins. Mass Spectrum m/z 465, 467 [MH$^+$]. |
| 139 | N-cyclopropyl-3-({[({[(2S)-4-(3,4-dichlorobenzyl)morpholin-2-yl]methyl}amino)carbonyl]amino}methyl)benzenesulfonamide | Example 136 | LC-MS (System A): Rt 2.57 mins. Mass Spectrum m/z 527, 529 [MH$^+$]. |
| 140 | N-{[(2S)-4-(3,4-dichlorobenzyl)morpholin-2-yl]methyl}-N'-[(4-methyl-1,3-thiazol-2-yl)methyl]urea | Example 136 | LC-MS (System A): Rt 2.33 mins. Mass Spectrum m/z 429, 431 [MH$^+$]. |
| 141 | N-{[(2S)-4-(3,4-dichlorobenzyl)morpholin-2-yl]methyl}-N'-(1,3-thiazol-2-ylmethyl)urea | Example 136 | LC-MS (System A): Rt 2.23 mins. Mass Spectrum m/z 415, 417 [MH$^+$]. |
| 142 | N-{[(2S)-4-(3,4-dichlorobenzyl)morpholin-2-yl]methyl}-N'-{[3-(4-methoxyphenyl)isoxazol-5-yl]methyl}urea | Example 136 | LC-MS (System A): Rt 2.73 mins. Mass Spectrum m/z 505, 507 [MH$^+$]. |
| 143 | tert-butyl 4-({[({[4-(3,4-dichlorobenzyl)morpholin-2-yl]methyl}amino)carbonyl]amino}methyl)piperidine-1-carboxylate | Example 43 | LC-MS (System A): Rt 2.69 mins. Mass Spectrum m/z 515 [MH$^+$]. |
| 144 | N-cyclopropyl-4-({[({[(2S)-4-(3,4-dichlorobenzyl)morpholin-2-yl]methyl}amino)carbonyl]amino}methyl)benzenesulfonamide | Example 136 | LC-MS (System A): Rt 2.54 mins. Mass Spectrum m/z 527, 529 [MH$^+$]. |

Example 145

N-{[(2S)-4-(3,4-Dichlorobenzyl)morpholin-2-yl]methyl}N'-[3-(ethylsulfonyl)propyl]urea Intermediate 40 (0.0225 g) and N,N-diisopropylethylamine (0.021 ml) were added to a solution of Intermediate 10 (0.044 g) in dichloromethane (3 ml), and the mixture was shaken at 22° C. for 19 h. Formyl polystyrene scavenging resin (2.95 mmol/g, 0.02 g) was added and the mixture shaken for 2 h. The mixture was filtered, the resin washed with dichloromethane, and the filtrate applied directly to a sulphonic acid ion exchange cartridge (2 g Isolute SCX). Elution with methanol followed by 10% 0.880 ammonia in methanol gave the crude product (0.04 g). Purification by chromatography on silica gel (Varian Bond Elut 1 g cartridge), eluting with dichloromethane, ether, ethyl acetate, and acetone, gave the title compound (0.029 mg).

LC-MS (System A) Rt 2.22 mins Mass Spectrum m/z 452 [MH$^+$].

Examples 146–159

| | Name | Preparation analogous to | Characterising Data |
|---|---|---|---|
| 146 | N-{[(2S)-4-(3,4-dichlorobenzyl)morpholin-2-yl]methyl}-N'-[3-(isopropylsulfonyl)propyl]urea | Example 145 | LC-MS (System A): Rt 2.30 mins. Mass Spectrum m/z 466 [MH$^+$]. |
| 147 | N-{[(2S)-4-(3,4-dichlorobenzyl)morpholin-2-yl]methyl}-N'-[3-(propylsulfonyl)propyl]urea | Example 145 | LC-MS (System A): Rt 2.34 mins. Mass Spectrum m/z 466 [MH$^+$]. |
| 148 | N-[3-(tert-butylsulfonyl)propyl]-N'-{[(2S)-4-(3,4-dichlorobenzyl)morpholin-2-yl]methyl}urea | Example 145 | LC-MS (System A): Rt 2.41 mins. Mass Spectrum m/z 480 [MH$^+$]. |
| 149 | 4-({[({[(2S)-4-(3,4-dichlorobenzyl)morpholin-2-yl]methyl}amino)carbonyl]amino}methyl)-N-methylbenzamide | Example 57 | LC-MS (System A): Rt 2.28 mins. Mass Spectrum m/z 465 [MH$^+$]. |

-continued

| | Name | Preparation analogous to | Characterising Data |
|---|---|---|---|
| 150 | N-cyclopropyl-4-({[({[(2S)-4-(3,4-dichlorobenzyl)morpholin-2-yl]methyl}amino)carbonyl]amino}methyl)benzamide | Example 57 | Chiral analytical HPLC, eluent 15% ethanol in n-heptane, detection at 230 nm, Rt 29.7 min. LC-MS (System A): Rt 2.38 mins. Mass Spectrum m/z 491 [MH+]. |
| 151 | ethyl 4-{[({[4-(3,4-dichlorobenzyl)morpholin-2-yl]methyl}amino)carbonyl]amino}piperidine-1-carboxylate | Example 47 | LC-MS (System A): Rt 2.61 mins. Mass Spectrum m/z 473 [MH+]. |
| 152 | N-{[4-(3,4-dichlorobenzyl)morpholin-2-yl]methyl}-N'-[2-(2-oxoimidazolidin-1-yl)ethyl]urea | Example 47 | LC-MS (System A): Rt 2.05 mins. Mass Spectrum m/z 430, 432 [MH+]. |
| 153 | N-{[4-(3,4-dichlorobenzyl)morpholin-2-yl]methyl}-N'-tetrahydro-2H-pyran-4-ylurea | Example 47 | LC-MS (System A): Rt 2.42 mins. Mass Spectrum m/z 358[MH+]. |
| 154 | N-{[4-(3,4-dichlorobenzyl)morpholin-2-yl]methyl}-N'-(2-morpholin-4-ylethyl)urea | Example 47 | LC-MS (System A): Rt 1.76 mins. Mass Spectrum m/z 431 [MH+]. |
| 155 | ethyl 4-[({[4-(3,4-dichlorobenzyl)morpholin-2-yl]methyl}amino)carbonyl]piperazine-1-carboxylate | Example 47 | LC-MS (System A): Rt 2.36 mins. Mass Spectrum m/z 459 [MH+]. |
| 156 | N-{[4-(3,4-dichlorobenzyl)morpholin-2-yl]methyl}morpholine-4-carboxamide | Example 47 | LC-MS (System A): Rt 2.12 mins. Mass Spectrum m/z 388 [MH+]. |
| 157 | N-{[4-(3,4-dichlorobenzyl)morpholin-2-yl]methyl}-4-(3-fluorophenyl)piperazine-1-carboxamide | Example 47 | LC-MS (System A): Rt 2.77 mins. Mass Spectrum m/z 481 [MH+]. |
| 158 | N-{[4-(3,4-dichlorobenzyl)morpholin-2-yl]methyl}-4-methylpiperidine-1-carboxamide | Example 47 | LC-MS (System A): Rt 2.56 mins. Mass Spectrum m/z 400 [MH+]. |
| 159 | N-{[(4-(3,4-dichlorobenzyl)morpholin-2-yl]methyl}-4-(2-furoyl)piperazine-1-carboxamide | Example 47 | LC-MS (System A): Rt 2.31 mins. Mass Spectrum m/z 481 [MH+]. |

Example 160

N-{[4-(3,4-dichlorobenzyl)morpholin-2-yl]methyl}-N'-[1-(methylsulfonyl)piperidin-4-yl]urea Methane sulphonyl chloride (0.009 ml) was added to a solution of Intermediate 16 (0.04 g) and N,N-diisopropyl-ethylamine (0.048 ml) in dichloromethane (3 ml). The solution was stirred for 5 h at 23° C. The solvent was removed in vacuo and the residue was purified by solid phase extraction (Isolute SCX sulphonic acid column) eluting with methanol followed by 10% 0.880 ammonia solution in methanol, to give the title compound as a pale yellow gum (0.034 g).

LC/MS (System A) Rt 2.5 min Mass spectrum m/z 479 [MH+].

Example 161

N-{[4-(3,4-dichlorobenzyl)morpholin-2-yl]methyl}-N'-{1-[(3,5-dimethylisoxazol-4-yl)sulfonyl]piperidin-4-yl}urea Example 161 was made in an analogous manner to that of Example 160

LC-MS (System A) Rt 2.86 mins. Mass Spectrum m/z 561 [MH+].

Example 162

N-(1-benzoylpiperidin-4-yl)-N'-{[4-(3,4-dichlorobenzyl)morpholin-2-yl]methyl}urea Benzoyl choride (0.014 ml) was added to a solution of Intermediate 16 (0.04 g) and N,N-diisopropylethylamine (0.048 ml) in dichloromethane (3 ml). The solution was stirred for 5 h at 23° C. The solvent was removed in vacuo and the residue purified by solid phase extraction (Isolute SCX sulphonic acid column) eluting with methanol followed by 10% 0.880 ammonia solution in methanol. The basic fraction was concentrated in vacuo and the residue was further purified using a silica gel solid phase extraction cartridge (1 g Varian Bond Elut), eluting sequentially with dichloromethane, ethyl acetate, acetone, acetonitrile, and methanol, to give the title compound as a clear gum (0.024 g).

LC/MS (System A) Rt 2.63 min, Mass spectrum m/z 506 [MH⁺].

Examples 163–168

| | Name | Preparation analogous to | Characterising Data |
|---|---|---|---|
| 163 | N-{[4-(3,4-dichlorobenzyl)morpholin-2-yl]methyl}-N'-[4-(methylsulfonyl)benzyl]urea | Example 47 | LC-MS (System A): Rt mins 2.61. Mass Spectrum m/z 486 [MH⁺]. |
| 164 | N'-{[4-(3,4-dichlorobenzyl)morpholin-2-yl]methyl}-N-(3-hydroxypropyl)-N-pyridin-2-ylurea | Example 43 | LC-MS (System A): Rt 2.19 mins. Mass Spectrum m/z 453 [MH⁺]. |
| 165 | N-(2-{[({[4-(3,4-dichlorobenzyl)morpholin-2-yl]methyl}amino)carbonyl]amino}ethyl)methanesulfonamide | Example 43 | LC-MS (System A): Rt 2.33 mins. Mass Spectrum m/z 439 [MH⁺]. |
| 166 | 4-{[({[4-(3,4-dichlorobenzyl)morpholin-2-yl]methyl}amino)carbonyl]amino}butanamide | Example 43 | LC-MS (System A): Rt 2.21 mins. Mass Spectrum m/z 403 [MH⁺]. |
| 167 | (2E)-4-{[({[4-(3,4-dichlorobenzyl)morpholin-2-yl]methyl}amino)carbonyl]amino}but-2-enoic acid compound with N,N,N-triethylamine (1:1) | Example 43 | LC-MS (System A): Rt 2.18 mins. Mass Spectrum m/z 402 [MH⁺]. |
| 168 | N-(2-{[({[4-(3,4-dichlorobenzyl)morpholin-2-yl]methyl}amino)carbonyl]amino}ethyl)acetamide | Example 43 | LC-MS (System A): Rt 2.06 mins. Mass Spectrum m/z 403 [MH⁺]. |

Example 169

N-{[4-(3,4-dichlorobenzyl)morpholin-2-yl]methyl}thiomorpholine-4-carboxamide 1,4-Thioxane (0.02 g) and N,N-diisopropylethylamine (0.04 ml) were added to a solution of Intermediate 10 (0.08 g) in dichloromethane (2 ml). The mixture was stirred at 23° C. for 16 h, and the solvent evaporated in vacuo. The residue was dissolved in dichloromethane (3 ml), and the solution shaken with polystyrene methyl isocyanate resin (Argonaut Technologies, 0.14 g, 1.45 mmol/g) for 2 h. The solution was drained from the resin, and the resin washed with dichloromethane (6 ml) and methanol (3 ml); the combined filtrate and washings were concentrated in vacuo. The residue was purified further by solid phase extraction (Isolute SCX sulphonic acid column), eluting with methanol followed by 10% 0.880 ammonia solution in methanol, to give the title compound as a pale yellow gum (0.065 g).

LCMS (system A) $R_t$ 2.55 min, Mass Spectrum m/z 404 [MH⁺].

Examples 170–174

| | Name | Preparation analogous to | Characterising Data |
|---|---|---|---|
| 170 | N-{[4-(3,4-dichlorobenzyl)morpholin-2-yl]methyl}-N'-(1,1-dioxidotetrahydrothien-3-yl)urea | Example 43 | LC-MS (System A): Rt 2.35 mins. Mass Spectrum m/z 436 [MH⁺]. |
| 171 | N-{[4-(3,4-dichlorobenzyl)morpholin-2-yl]methyl}-N'-tetrahydro-2H-thiopyran-4-ylurea | Example 43 | LC-MS (System A): Rt 2.65 mins. Mass Spectrum m/z 418 [MH⁺]. |
| 172 | N-{[4-(3,4-dichlorobenzyl)morpholin-2-yl]methyl}-N'-[1-(4-fluorophenyl)ethyl]urea | Example 136 | LC-MS (System A): Rt 2.89 mins. Mass Spectrum m/z 440, 442 [MH⁺]. |
| 173 | N-{[4-(3,4-dichlorobenzyl)morpholin-2-yl]methyl}-N'-(1-methyl-1-phenylethyl)urea | Example 136 | LC-MS (System A): Rt 2.96 mins. Mass Spectrum m/z 436, 438 [MH⁺]. |
| 174 | N-{[4-(3,4-dichlorobenzyl)morpholin-2- | Example 136 | LC-MS (System A): Rt 2.10 mins. |

-continued

| Name | Preparation analogous to | Characterising Data |
|---|---|---|
| yl]methyl}-N'-[2-thioxo-2,3-dihydro-1H-imidazol-4-yl)methyl]urea | | Mass Spectrum m/z 430, 432 [MH⁺]. |

Example 175

N{[4-(3,4-dichlorobenzyl)morpholin-2-yl]methyl}thiomorpholine-4-carboxamide 1,1-dioxide Oxone (0.135 g) was added to Example 169 (0.06 g) in methanol:water (10:1, 4 ml) at 23° C. under nitrogen, and the mixture was stirred for 18 h. The methanol was removed in vacuo, the aqueous layer was diluted with sodium sulphite solution (5%, 5 ml) and the product was extracted into dichloromethane (8 ml). The organic layer was washed with brine (5 ml), dried (MgSO$_4$) and concentrated in vacuo to give the title compound as a white solid (0.055 g).

LC/MS (System A) Rt 2.34 min Mass spectrum m/z 436 [MH⁺].

Examples 176–181

| | Name | Preparation analogous to | Characterising Data |
|---|---|---|---|
| 176 | N-{[4-(3,4-dichlorobenzyl)morpholin-2-yl]methyl}-4-(methylsulfonyl)piperazine-1-carboxamide | Example 43 | LC-MS (System A): Rt 2.24 mins. Mass Spectrum m/z 465 [MH⁺]. |
| 177 | N-{[4-(3,4-dichlorobenzyl)morpholin-2-yl]methyl}-2-(4-methylpyridin-2-yl)pyrrolidine-1-carboxamide | Example 136 | LC-MS (System A): Rt 2.19 mins. Mass Spectrum m/z 463, 465 [MH⁺]. |
| 178 | N-{[(2S)-4-(3,4-dichlorobenzyl)morpholin-2-yl]methyl}-N'-[2-(4-methoxyphenyl)-2-oxoethyl]urea | Example 136 | LC-MS (System A): Rt 2.55 mins. Mass Spectrum m/z 466, 468 [MH⁺]. |
| 179 | N-{[(2S)-4-(3,4-dichlorobenzyl)morpholin-2-yl]methyl}-1,3,4,5-tetrahydro-2H-2-benzazepine-2-carboxamide | Example 136 | LC-MS (System A): Rt 2.69 mins. Mass Spectrum m/z 448, 450 [MH⁺]. |
| 180 | N-{[(2S)-4-(3,4-dichlorobenzyl)morpholin-2-yl]methyl}-N'-phenoxyurea | Example 136 | LC-MS (System A): Rt 2.57 mins. Mass Spectrum m/z 410, 412 [MH⁺]. |
| 181 | N-{[(2S)-4-(3,4-dichlorobenzyl)morpholin-2-yl]methyl}-N'-(2-phenoxyethyl)urea | Example 136 | LC-MS (System A): Rt 2.64 mins. Mass Spectrum m/z 438, 440 [MH⁺]. |

Example 182

N-{[1-(Cyclopropylcarbonyl)piperidin-4-yl]methyl}-N'-{[(2S)-4-(3,4-dichlorobenzyl)morpholin-2-yl]methyl}urea Cyclopropanecarbonyl chloride (0.014 ml) was added to a solution of Intermediate 18 (0.54 g) and N,N-diisopropylethylamine (0.063 ml) in dichloromethane (2 ml). The solution was stirred for 3 h at 23° C. The solvent was removed in vacuo and the residue purified by solid phase extraction (Isolute SCX sulphonic acid column) eluting with methanol followed by 10% 0.880 ammonia solution in methanol. The basic fraction was concentrated in vacuo and the residue was further purified using a silica gel solid phase extraction cartridge (1 g Varian Bond Elut) eluting with 0–1% methanol in ethyl acetate, to give the title compound as a clear gum (0.023 g).

LC/MS (system A) Rt 2.35 min Mass spectrum m/z 483 [MH⁺].

Example 183

N-{[(2S)-4-(3,4-Dichlorobenzyl)morpholin-2-yl]methyl}-N'-{[1-(methylsulfonyl)piperidin-4-yl]methyl}urea Methane sulphonyl choride (0.013 ml) was added to a solution of Intermediate 18 (0.054 g) and N,N-diisopropylethylamine (0.063 ml) in dichloromethane (2 ml). The solution was stirred for 16 h at 23° C. The solvent was removed in vacuo and the residue purified by solid phase extraction (Isolute SCX sulphonic acid column) eluting with methanol followed by 10% 0.880 ammonia solution in methanol, to give the title compound as a clear gum (0.035 g).

LC/MS (system A) Rt 2.34 min Mass spectrum m/z 493 [MH⁺].

Example 184
4-({[({[4-(3,4-Dichlorobenzyl)-1,4-oxazepan-2-yl]methyl}amino)carbonyl]amino}methyl)benzamide To a solution of 1,1'-carbonyldiimidazole (0.041 g) in dichloromethane (2 ml) at 0° C. was added dropwise asolution of Intermediate 41 (0.079 g) in dichloromethane (2 ml). The mixture was stirred at 0° C. for 1 h and at 22° C. for 1 h, re-cooled to approximately 0° C. and a solution of 4-aminomethylbenzamide (0.041 g) in a 1:1 mixture of dichloromethane and N,N-dimethylformiamide (4 ml) was added dropwise. The mixture was stirred at 0° C. for 1 h and at 22° C. for 1 h, and applied in two equal portions to ion exchange cartridges (2 g Isolute SCX pre-conditioned with methanol). Elution with methanol (3 column volumes) followed 10% 0.880 ammonia in methanol (2 column volumes) and evaporation of the basic fractions in vacuo gave the crude product. Purification by Biotage flash chromatography on a silica gel cartridge (89), eluting with 150:8:1 dichloromethane/ethanol/0.880 ammonia, gave the title compound as a white solid (0.0186 g).

LCMS (system A) $R_t$ 2.22 min Mass Spectrum m/z 465 [MH$^+$]

Example 185
4-[({[({(2S)-4-[1-(3,4-Dichlorophenyl)ethyl]morpholin-2-yl}methyl)amino]carbonyl}amino)methyl]benzamide, Isomer II Intermediate 35 (0.045 g) in dichloromethane (1 ml) was treated with N,N-diisopropylethylamine (0.021 ml) in a 5 ml vial (Pierce Reacti-Vial™) followed by 4-aminomethylbenzamide (0.017 g). The mixture was sealed under nitrogen and stirred at room temperature for 18 h. The solution was then applied to a sulphonic acid ion exchange cartridge (2 g Isolute SCX) which had been pre-treated with methanol. The cartridge was eluted with methanol (7 column volumes) followed by 10% 0.880 ammonia in methanol (3 column volumes), and the basic fractions combined and concentrated in vacuo to give a yellow gum. Further purification by chromatography on silica gel (Varian Bond Elut 1 g cartridge), eluting with 10% methanol in ethyl acetate, gave the title compound as a yellow gum (0.036 g).

LC/MS (System A) $R_t$ 2.25 min Mass spectrum m/z 465 [MH$^+$]

Example 186
4-[({[({(2S)-4-[1-(3,4-Dichlorophenyl)ethyl]morpholin-2-yl}methyl)amino]carbonyl}amino)methyl]benzamide, Isomer I Intermediate 34 (0.045 g) in dichloromethane (1 ml) was treated with N,N-diisopropylethylamine (0.021 ml) in a 5 ml vial (Pierce Reacti-Vial™) followed by 4-aminomethylbenzamide (0.017 g). The mixture was sealed under nitrogen and stirred at room temperature for 18 h. The solution was then applied to a sulphonic acid ion exchange cartridge (2 g Isolute SCX) which had been pre-treated with methanol. The cartridge was eluted with methanol (7 column volumes) followed by 10% 0.880 ammonia in methanol (3 column volumes), and the basic fractions combined and concentrated in vacuo to give a yellow gum. Further purification by chromatography on silica gel (Varian Bond Elut 1 g cartridge), eluting with 10% methanol in ethyl acetate gave the title compound as a yellow gum (0.036 g).

LC/MS (System A) $R_t$ 2.27 min. Mass spectrum m/z 465 [MH$^+$].

Example 187
4-{[({[(2S)-4-(3,4-dichlorobenzyl)morpholin-2-yl]methyl}amino)carbonyl]amino}-N-methylbutanamide N,N'-carbonyldiimidazole (0.0132 g) was added to a stirred solution of Intermediate 26 (0.030 g) in N,N-dimethylformamide (2 ml), and the mixture stirred at 22° C. under nitrogen for 40 min. Methylamine (2.0M solution in tetrahydrofuran, 0.102 ml) was added, and stirring was continued at 22° C. for 17 h. The mixture was applied directly to a sulphonic acid ion exchange cartridge (2 g Isolute SCX), and eluted with methanol followed by 10% 0.880 ammonia in methanol to give a gum (0.042 g). Purification by chromatography on silica gel (1 g Varian Bond Elut cartridge), eluting with chloroform, ether, ethyl acetate, acetone, and methanol, gave a gum (0.025 g), which was further purified by mass directed preparative HPLC to give the title compound as a colourless gum (7.2 mg).

LC-MS (System A) Rt 2.11 min Mass Spectrum m/z 417 [MH$^+$].

Example 188
3-{[({[(2S)-4-(3,4-dichlorobenzyl)morpholin-2-yl]methyl}amino)carbonyl]amino}-N-methylpropane-1-sulfonamide Example 188 was prepared in an analogous manner to that of Example 189.

LC-MS (System A): Rt 2.20 mins Mass Spectrum m/z 453 [MH+].

Example 189
N-{[(2S)-4-(3,4-dichlorobenzyl)morpholin-2-yl]methyl}-N'-[3-(pyrrolidin-1-ylsulfonyl)propyl]urea A solution of Intermediate 28 (0.027 g) in N,N-dimethylformamide (1 ml) and dichloromethane (2 ml) containing N,N-diisopropylethylamine (0.041 ml) was added to a stirred solution of Intermediate 13 (0.051 g) in dry dichloromethane (2 ml) at room temperature under nitrogen, and the mixture was stirred at room temperature for 21 h. The mixture was applied directly to a sulphonic acid ion exchange cartridge (2 g Isolute SCX) and eluted with methanol (6 column volumes) followed by 10% 880 ammonia in methanol (3 column volumes); evaporation of the methanol/ammonia fractions gave the crude product (0.063 g). Purification by chromatography on silica gel (2 g Varian Bond Elut cartridge), eluting with chloroform, ether, ethyl acetate, acetone, and methanol, gave the title compound as a gum (0.036 g).

LC-MS (System A) Rt 2.41 min. Mass Spectrum m/z 493 [MH$^+$].

Biological Data

The compounds of the Examples were tested in the CCR-3 binding and/or eosinophil chemotaxis assays (assays (a) and (b)) and results were obtained as follows:

| Example | CCR-3 Binding Assay (pIC50) | CCR-3 Eosinophil Chemotaxis Assay (fpKi) |
| --- | --- | --- |
| 2 | | 7.31 |
| 3 | 7.16 | |
| 4 | | 7.35 |
| 5 | 6.93 | |
| 8 | | 6.94 |
| 13 | | 6.39 |
| 14 | 6.18 | |
| 16 | 6.13 | |
| 18 | | 5.84 |
| 19 | | 5.96 |
| 21 | 6.02 | |
| 22 | 6.02 | |
| 23 | 6.08 | |
| 25 | 6.00 | |
| 26 | | 5.85 |
| 34 | 5.70 | |
| 37 | 5.42 | |
| 38 | 5.72 | |
| 44 | 4.98 | |
| 47 | 7.18 | |
| 48 | | 7.41 |
| 52 | 8.75 | |
| 54 | 7.96 | 7.8 |
| 57 | | 8.01 |
| 136 | 7.8 | 8.3 |
| 149 | 7.8 | 7.8 |

Compounds of Examples 1, 6–7, 9–12, 15, 17, 20, 24, 27–33, 35–36, 39–43, 45–46, 49–51, 53, 55–56, 58–135, 137–148 and 150–189 were also tested in CCR-3 binding assay (assay (a)) and achieved a pIC50 value greater than 5.0.

Example 14 when tested in the ovalbumin sensitised guinea-pig in vivo model (assay (c); 0.2–20 mg/kg), showed inhibition of lung eosinophilia and bronchial hyperreactivity.

Throughout the specification and the claims which follow, unless the context requires otherwise, the word 'comprise', and variations such as 'comprises' and 'comprising', will be understood to imply the inclusion of a stated integer or step or group of integers but not to the exclusion of any other integer or step or group of integers or steps.

The invention claimed is:

1. 4-({[({[(2S)-4-(3,4-Dichlorobenzyl)morpholin-2-yl]methyl}amino)carbonyl]amino}methyl)benzamide or a physiologically acceptable salt or solvate thereof.

2. 4-({[({[(2S)-4-(3,4-dichlorobenzyl)morpholin-2-yl]methyl}amino)carbonyl]amino}methyl)N-methylbenzamide or a physiologically acceptable salt or solvate thereof.

3. A method of treatment of asthma in a human in need thereof which comprises administering to the human an effective amount of a compound of formula (I):

(I)

wherein:

$R^1$ is phenyl-$Y^1$ substituted with —$CONH_2$ or —$CONHCH_3$;

$Y^1$ is —$CH_2$—;

$R^2$ is hydrogen or $C_{1-6}$ alkyl optionally substituted by a hydroxy group;

$R^3$ is hydrogen or $C_{1-6}$ alkyl;

X is methylene;

$R^4$ and $R^5$ are each hydrogen;

Z is $CH_2$;

$R^6$ is phenyl optionally substituted with one or more halogens;

a and b are each 1;

or a physiologically acceptable salt or solvate thereof.

4. A method of treatment of asthma in a human in need thereof which comprises administering to the human an effective amount of 4-({[({[(2S)-4-(3,4-Dichlorobenzyl)morpholin-2-yl]methyl}amino)carbonyl]amino}methyl)benzamide or a physiologically acceptable salt or solvate thereof.

5. A method of treatment of nasal polyposis, conjunctivitis or pruritis in a human in need thereof which comprises administering to the human an effective amount of a compound of formula (I):

(I)

wherein:

$R^1$ is phenyl-$Y^1$ substituted with —$CONH_2$ or —$CONHCH_3$;

$Y^1$ is —$CH_2$—;

$R^2$ is hydrogen or $C_{1-6}$ alkyl optionally substituted by a hydroxy group;

$R^3$ is hydrogen or $C_{1-6}$ alkyl;

X is methylene;

$R^4$ and $R^5$ are each hydrogen;

Z is $CH_2$;

$R^6$ is phenyl optionally substituted with one or more halogens;

a and b are each 1;

or a physiologically acceptable salt or solvate thereof.

6. A method of treatment of nasal polyposis, conjunctivitis or pruritis in a human in need thereof which comprises administering to the human an effect amount of 4-({[({[(2S)-4-(3,4-Dichlorobenzyl)morpholin-2-yl]methyl}amino)carbonyl]amino}methyl)benzamide or a physiologically acceptable salt or solvate thereof.

* * * * *